United States Patent
Wu et al.

(10) Patent No.: US 10,189,881 B2
(45) Date of Patent: *Jan. 29, 2019

(54) MPS PEPTIDES AND USE THEREOF

(71) Applicant: The Regents of the University of California, Oakland, CA (US)

(72) Inventors: Reen Wu, Davis, CA (US); Ching-Hsien Chen, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/907,539

(22) PCT Filed: Jul. 25, 2014

(86) PCT No.: PCT/US2014/048285
§ 371 (c)(1),
(2) Date: Jan. 25, 2016

(87) PCT Pub. No.: WO2015/013669
PCT Pub. Date: Jan. 29, 2015

(65) Prior Publication Data
US 2016/0176936 A1    Jun. 23, 2016

Related U.S. Application Data

(60) Provisional application No. 61/976,443, filed on Apr. 7, 2014, provisional application No. 61/859,138, filed on Jul. 26, 2013.

(51) Int. Cl.
| | |
|---|---|
| A61K 38/00 | (2006.01) |
| C07K 14/47 | (2006.01) |
| C07K 16/30 | (2006.01) |
| A61K 31/517 | (2006.01) |
| A61K 31/5377 | (2006.01) |
| A61K 31/713 | (2006.01) |
| A61K 38/17 | (2006.01) |
| A61K 45/06 | (2006.01) |
| C07K 16/18 | (2006.01) |
| C12N 15/113 | (2010.01) |
| G01N 33/574 | (2006.01) |

(52) U.S. Cl.
CPC ........ *C07K 14/4738* (2013.01); *A61K 31/517* (2013.01); *A61K 31/5377* (2013.01); *A61K 31/713* (2013.01); *A61K 38/1709* (2013.01); *A61K 45/06* (2013.01); *C07K 16/18* (2013.01); *C07K 16/3023* (2013.01); *C12N 15/113* (2013.01); *G01N 33/57423* (2013.01); *G01N 33/57496* (2013.01); *A61K 38/00* (2013.01); *C07K 2317/34* (2013.01); *C12N 2310/14* (2013.01); *C12N 2310/531* (2013.01); *C12N 2320/31* (2013.01); *G01N 2333/4703* (2013.01); *G01N 2440/14* (2013.01)

(58) Field of Classification Search
None
See application file for complete search history.

(56) References Cited

U.S. PATENT DOCUMENTS

| | | | |
|---|---|---|---|
| 7,265,088 B1 * | 9/2007 | Li | A61K 38/10 514/21.2 |
| 2008/0020031 A1 | 1/2008 | Li et al. | |
| 2009/0169559 A1 | 7/2009 | Cohen-Vered et al. | |
| 2009/0203620 A1 | 8/2009 | Parikh | |
| 2009/0220581 A1 | 9/2009 | Li et al. | |
| 2010/0015117 A1 | 1/2010 | Verma et al. | |
| 2010/0310568 A1 | 12/2010 | Prat et al. | |
| 2012/0108445 A1 | 5/2012 | Lenz | |
| 2013/0196896 A1 | 8/2013 | Komatsu et al. | |
| 2016/0176936 A1 | 6/2016 | Wu et al. | |
| 2017/0028019 A1 | 2/2017 | Wu et al. | |

FOREIGN PATENT DOCUMENTS

| | | | |
|---|---|---|---|
| KR | 10-0832317 | * | 5/2008 |
| WO | WO-2012/006640 A2 | | 1/2012 |
| WO | 2013/033459 | * | 3/2013 |
| WO | WO-2015/013669 A1 | | 1/2015 |
| WO | WO-2016/011301 A1 | | 1/2016 |

OTHER PUBLICATIONS

Nelson et al., Ann. Intern Med. 2009; 151:727-737.*
Kataja et al., Ann Oncol 2009; 20(sup 4): iv10-14.*
Balmana et al. Ann Oncol 2009; 20(supp 4):iv19-20.*
Brand et al., Anticancer Res. 2006; 26:463-70.*
Translation of KR 10-0832317.*
Chen, C-H. et al. (2013) "Poster Presentations—Cell Migration and invasion 3; Abstract 4919: Myristoylated alanine-rich C kinase substrate (MARCKS) phosphorylation potentials human lung cancer cell malignancy," Cancer Research 73(8) Suppl. 1, abstract.
International Search Report and Written Opinion (ISA/US) for International Application No. PCT/US2014/048285, dated Nov. 24, 2014.
Arbuzova, A. et al. (2002) "Cross-talk unfolded: MARCKS proteins," Biochem J 362: 1-12.
Chen, C-H. et al. (2014) "A Novel Predictor of Cancer Malignancy: Up-Regulation of Myristoylated Alanine-Rich C Kinase Substrate Phosphorylation in Lung Cancer," American J of Resp and Crit Care Med 189(8): 1002-1004.
Chen, C-H. et al. (2014) "A peptide that inhibits function of Myristoylated Alanine-Rich C Kinase Substrate (MARCKS) reduces lung cancer metastasis," Oncogene 33(28) 3696-3706.

(Continued)

*Primary Examiner* — Sheela J. Huff
(74) *Attorney, Agent, or Firm* — Foley & Lardner LLP; Antoinette F. Konski

(57) ABSTRACT

This disclosure provides an isolated polypeptide comprising no more than 35 amino acids, wherein the amino acid sequence comprises, or alternatively consists essentially of, or alternatively consisting of XXXRYSYXXSYX (SEQ ID NO: 1) and equivalents thereof, wherein X is a basic amino acid and Y is a hydrophobic amino acid. Polynucleotides encoding the polypeptides and antibodies that bind to the polypeptides are also provided. Therapeutic and diagnostic uses are further provided.

24 Claims, 26 Drawing Sheets

Specification includes a Sequence Listing.

(56) References Cited

OTHER PUBLICATIONS

Eckert, R.E. et al. (2010) "Myristoylated Alanine-Rich C-Kinase Substrate (MARCKS) Protein Regulation of Human Neutrophil Migration," Am J Respir Cell Mol Biol 42: 586-94.

Ellena, J.F. et al. (2003) "Location of the myristoylated ananine-rich C-kinase substrate (MARCKS) effector domain in negatively charged phospholipid bicelles," Biophys J 35: 2442-28.

Elzagallaai, A. et al. (2000) "Platelet secretion induced by phorbol esters stimulation is mediated through phosphorylation of MARCKS: a MARCKS-derived peptide blocks MARCKS phosphorylation and serotonin release without affecting pleckstrin phosphorylation," Blood 95: 894-902.

Gay, E.A. (2008) "Inhibition of native and recombinant nicotinic acetylcholine receptors by the myristoylated alanine-rich C kinase substrate peptide," J Pharmacol Exp Ther 327: 884-90.

Glaser, M. et al. (1996) "Myristoylated alanine-rich C kinase substrate (MARCKS) produces reversible inhibition of phospholipase C by sequestering phosphatidylinositol 4,5-bisphosphate in lateral domains," J Biol Chem 271: 26187-93.

Graff, J.M. et al. (1991) "Protein kinase C substrate and inhibitor characteristics of peptides derived from the myristoylated alanine-rich C kinase substrate (MARCKS) protein phosphorylation site domain," J Biol Chem 266: 14390-98.

Green, T.D. et al. (2011) "Regulation of mucin secretion and inflammation in asthma; A role for MARCKS protein?" Biochim Biophys Acta 1810(11): 1110-1113.

Hinrichsen, R.D. et al. (1993) "Regulation of peptide-calmodulin complexes by protein kinase C in vivo," Proc Natl Acad Sci USA 90: 1585-89.

Kalwa, H. et al. (2011) "The MARCKS protein plays a critical role in phosphatidylinositol 4,5-bisphosphate metabolism and directed cell movement in vascular endothelial cells," J Biol Chem 286: 2320-30.

Li, Y. et al. (2001) "MARCKS Protein is a Key Molecule Regulating Mucin Secretion by Human Airway Epithelial Cells In Vitro," J Biol Chem 276(44): 40982-40990.

Morton, L.A. et al. (2013) "MARCKS-ED peptide as a curvature and lipid sensor," ACS Chem Biol, 8: 218-25.

Park, J-H. et al. (2007) "Protein Kinase C delta Regulates Airway Mucin Secretion via Phosphorylation of Marcks Protein," Am J Pathol 171(6): 1822-30.

Singer, M. (2004) "A MARCKS-related peptide blocks mucus hypersecretion in a mouse model of asthma," Nat Med 10(2): 193-196.

Theis, T. et al. (2013) "Functional role of the interaction between polysialic acid and myristoylated alanine-rich C kinase substrate at the plasma membrane," J Biol Chem 288: 6726-42.

Timofeeva, O.A. et al. (2010) "Hippocampal infusions of MARCKS peptides impair memory of rats on the radial-arm maze," Brain Res 1308: 147-52.

Agrawal, A. et al. (2007) "Inhibition of mucin secretion with MARCKS-related peptide improves airway obstruction in a mouse model of asthma," J Appl Physiol 102(1): 399-405.

U.S. Office Action dated Jun. 30, 2017 from U.S. Appl. No. 15/106,263.

WO 2012006640 Sequence Listing, published Jan. 12, 2012.

U.S. Office Action dated Nov. 21, 2017, from U.S. Appl. No. 15/106,263.

U.S. Office Action dated Apr. 10, 2018, from U.S. Appl. No. 15/106,263.

Final Office Action dated Nov. 21, 2018, from U.S. Appl. No. 15/106,263.

* cited by examiner

MPS peptide WT: KKKKKRFSFKKSFKLSGFSFKKNKK
MPS peptide Mut: KKKKKRFDFKKDFKLDGFDFKKNKK

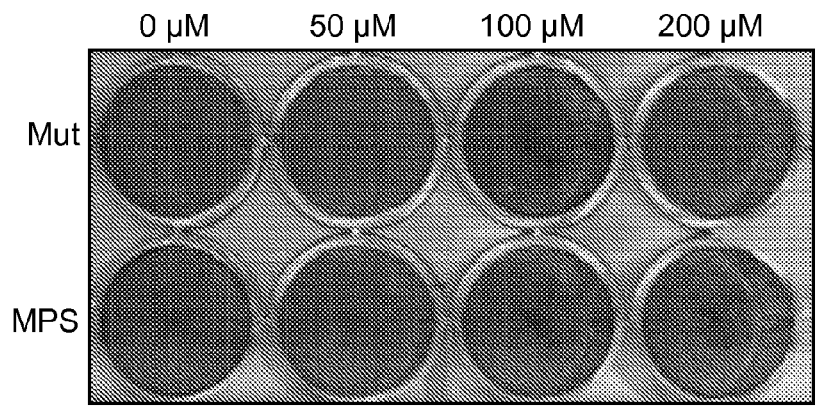
FIG. 20
| Cell lines | PI3K/PTEN status | Cancer type | Treatment status |
|---|---|---|---|
| PC9 | WT | Lung cancer | Sensitive to erlotinib |
| H1650 | PTEN null | Lung cancer | Resistant to erlotinib |
| H1975 | PIK3CA | Lung cancer | Resistant to erlotinib |
| A549 | WT | Lung cancer | Resistant to erlotinib |
| CL1-5 | PTEN mutation | Lung cancer | Resistant to erlotinib |
| HCT116 | PIK3CA mutation | Colon cancer | Resistant to erlotinib |
FIG. 21
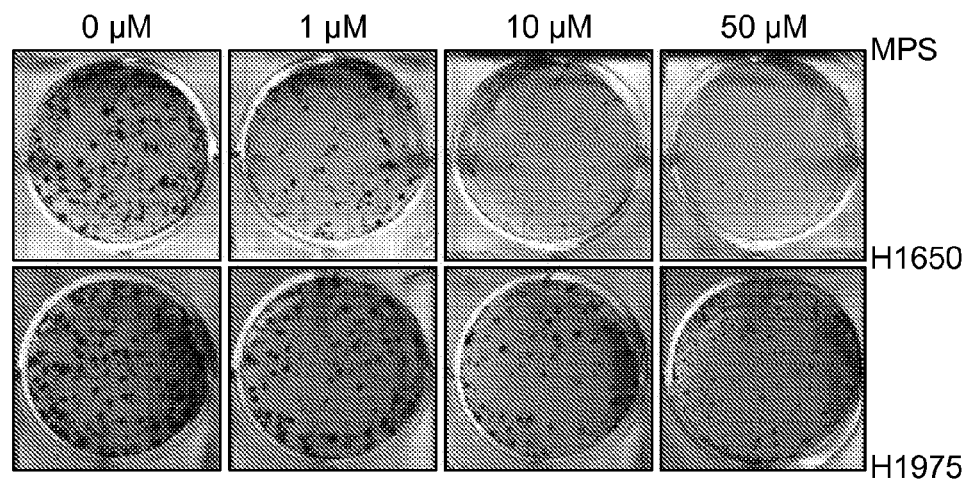
FIG. 22

A

| Cell lines | Mutation | CI Values at | | |
|---|---|---|---|---|
| | | ED50 | ED75 | ED90 |
| H1975 | EGFR L858R+T790M | 0.60 | 0.54 | 0.50 |
| H1650 | EGFR Exon 19del | 0.69 | 0.77 | 0.87 |
| H358 | K-Ras G12C | 0.55 | 0.67 | 0.88 |
| A549 | K-Ras G12S | 0.81 | 0.78 | 0.75 |

A

MPS peptide: KKKKKRFSFKKSFKLSGFSFKKNKK
D-Mut MPS peptide: KKKKKRFDFKKDFKLDGFDFKKNKK
A-Mut MPS peptide: KKKKKRFAFKKAFKLAGFAFKKNKK

B

C

SEQUENCE LISTING

```
<160> NUMBER OF SEQ ID NOS: 42

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any basic amino acid
<220> FEATURE:
<221> NAME/KEY: MOD_RES
<222> LOCATION: (5)..(5)
<223> OTHER INFORMATION: Any hydrophobic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (8)..(9)
<223> OTHER INFORMATION: Any basic amino acid
<220> FEATURE:
<221> NAME/KEY: MOD_RES
<222> LOCATION: (11)..(11)
<223> OTHER INFORMATION: Any hydrophobic amino acid
<220> FEATURE:
<221> NAME/KEY: MOD_RES
<222> LOCATION: (12)..(12)
<223> OTHER INFORMATION: Any basic amino acid

<400> SEQUENCE: 1

Xaa Xaa Xaa Arg Xaa Ser Xaa Xaa Xaa Ser Xaa Xaa
1               5                   10
```

```
<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Lys Lys Arg Phe Ser Phe Lys Lys Ser Phe Lys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Lys Lys Lys Arg Phe Ser Phe Lys Lys Ser Phe Lys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Ile, Leu, Val, Trp or Tyr
<220> FEATURE:
<221> NAME/KEY: MOD_RES
<222> LOCATION: (7)..(7)
<223> OTHER INFORMATION: Ala, Ile, Leu, Val, Trp or Tyr
<220> FEATURE:
<221> NAME/KEY: MOD_RES
<222> LOCATION: (11)..(11)
<223> OTHER INFORMATION: Ala, Ile, Leu, Val, Trp or Tyr

<400> SEQUENCE: 4

Lys Lys Lys Arg Xaa Ser Xaa Lys Lys Ser Xaa Lys
1               5                   10

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
```

```
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<221> NAME/KEY: MOD_RES
<222> LOCATION: (21)..(22)
<223> OTHER INFORMATION: Any basic amino acid
<220> FEATURE:
<221> NAME/KEY: MOD_RES
<222> LOCATION: (24)..(25)
<223> OTHER INFORMATION: Any basic amino acid

<400> SEQUENCE: 5

Xaa Xaa Xaa Xaa Xaa Arg Xaa Ser Xaa Xaa Xaa Ser Xaa Xaa Leu Ser
1               5                   10                  15

Gly Xaa Ser Xaa Xaa Xaa Asn Xaa Xaa
            20                  25

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: His or Arg
<220> FEATURE:
<221> NAME/KEY: MOD_RES
<222> LOCATION: (8)..(9)
<223> OTHER INFORMATION: His or Arg
<220> FEATURE:
<221> NAME/KEY: MOD_RES
<222> LOCATION: (12)..(12)
<223> OTHER INFORMATION: His or Arg

<400> SEQUENCE: 6

Xaa Xaa Xaa Arg Phe Ser Phe Xaa Xaa Ser Phe Xaa
1               5                   10

<210> SEQ ID NO 7
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ala, Ile, Leu, Val, Trp or Tyr
<220> FEATURE:
<221> NAME/KEY: MOD_RES
<222> LOCATION: (9)..(9)
<223> OTHER INFORMATION: Ala, Ile, Leu, Val, Trp or Tyr
<220> FEATURE:
<221> NAME/KEY: MOD_RES
<222> LOCATION: (13)..(13)
<223> OTHER INFORMATION: Ala, Ile, Leu, Val, Trp or Tyr
```

<400> SEQUENCE: 7

Lys Lys Lys Lys Lys Arg Xaa Ser Xaa Lys Lys Ser Xaa Lys Leu Ser
1               5                   10                  15

Gly Phe Ser Phe Lys Lys Asn Lys Lys
            20                  25

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: His or Arg
<220> FEATURE:
<221> NAME/KEY: MOD_RES
<222> LOCATION: (10)..(11)
<223> OTHER INFORMATION: His or Arg
<220> FEATURE:
<221> NAME/KEY: MOD_RES
<222> LOCATION: (14)..(14)
<223> OTHER INFORMATION: His or Arg
<220> FEATURE:
<221> NAME/KEY: MOD_RES
<222> LOCATION: (21)..(22)
<223> OTHER INFORMATION: His or Arg
<220> FEATURE:
<221> NAME/KEY: MOD_RES
<222> LOCATION: (24)..(25)
<223> OTHER INFORMATION: His or Arg

<400> SEQUENCE: 8

Xaa Xaa Xaa Xaa Xaa Arg Phe Ser Phe Xaa Xaa Ser Phe Xaa Leu Ser
1               5                   10                  15

Gly Phe Ser Phe Xaa Xaa Asn Xaa Xaa
            20                  25

<210> SEQ ID NO 9
<211> LENGTH: 25
<212> TYPE: PRT
<213> ORGANISM: Unknown
<220> FEATURE:
<223> OTHER INFORMATION: Description of Unknown: Wild-type MPS peptide

<400> SEQUENCE: 9

Lys Lys Lys Lys Lys Arg Phe Ser Phe Lys Lys Ser Phe Lys Leu Ser
1               5                   10                  15

Gly Phe Ser Phe Lys Lys Asn Lys Lys
            20                  25

<210> SEQ ID NO 10
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Lys Lys Lys Lys Arg Phe Ala Phe Lys Lys Ala Phe Lys Leu Ala
1               5                   10                  15

Gly Phe Ala Phe Lys Lys Asn Lys Lys
            20                  25

-continued

```
<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any basic amino acid
<220> FEATURE:
<221> NAME/KEY: MOD_RES
<222> LOCATION: (5)..(5)
<223> OTHER INFORMATION: Any hydrophobic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (8)..(9)
<223> OTHER INFORMATION: Any basic amino acid
<220> FEATURE:
<221> NAME/KEY: MOD_RES
<222> LOCATION: (11)..(11)
<223> OTHER INFORMATION: Any hydrophobic amino acid
<220> FEATURE:
<221> NAME/KEY: MOD_RES
<222> LOCATION: (12)..(12)
<223> OTHER INFORMATION: Any basic amino acid

<400> SEQUENCE: 11

Xaa Xaa Xaa Arg Xaa Ala Xaa Xaa Xaa Ala Xaa Xaa
1               5                   10

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<221> NAME/KEY: MOD_RES
```

```
<222> LOCATION: (21)..(22)
<223> OTHER INFORMATION: Any basic amino acid
<220> FEATURE:
<221> NAME/KEY: MOD_RES
<222> LOCATION: (24)..(25)
<223> OTHER INFORMATION: Any basic amino acid

<400> SEQUENCE: 12

Xaa Xaa Xaa Xaa Xaa Arg Xaa Ala Xaa Xaa Xaa Ala Xaa Xaa Leu Ala
1               5                   10                  15

Gly Xaa Ala Xaa Xaa Xaa Asn Xaa Xaa
            20                  25

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Lys Lys Arg Phe Ala Phe Lys Lys Ala Phe Lys
1               5                   10

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Lys Lys Lys Lys Arg Phe Asp Phe Lys Lys Asp Phe Lys Leu Asp
1               5                   10                  15

Gly Phe Asp Phe Lys Lys Asn Lys Lys
            20                  25

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gagaaggcgg tgaggctga                                               19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcagcctcac cgccttctc                                               19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 17
gaaggtaaac ggcgacgct                                                19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agcgtcgccg tttaccttc                                                19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gagcgcttct ccttcaagaa                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttcttgaagg agaagcgctc                                               20

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any basic amino acid
<220> FEATURE:
<221> NAME/KEY: MOD_RES
<222> LOCATION: (5)..(5)
<223> OTHER INFORMATION: Any hydrophobic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (8)..(9)
<223> OTHER INFORMATION: Any basic amino acid
<220> FEATURE:
<221> NAME/KEY: MOD_RES
<222> LOCATION: (11)..(11)
<223> OTHER INFORMATION: Any hydrophobic amino acid
<220> FEATURE:
<221> NAME/KEY: MOD_RES
<222> LOCATION: (12)..(12)
<223> OTHER INFORMATION: Any basic amino acid

<400> SEQUENCE: 21

```
Xaa Xaa Xaa Arg Xaa Ser Xaa Xaa Xaa Ser Xaa Xaa
1               5                   10
```

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any basic amino acid
<220> FEATURE:
<221> NAME/KEY: MOD_RES
<222> LOCATION: (6)..(6)
<223> OTHER INFORMATION: Any hydrophobic amino acid
<220> FEATURE:
<221> NAME/KEY: MOD_RES
<222> LOCATION: (8)..(8)
<223> OTHER INFORMATION: Any hydrophobic amino acid
<220> FEATURE:
<221> NAME/KEY: MOD_RES
<222> LOCATION: (9)..(10)
<223> OTHER INFORMATION: Any basic amino acid
<220> FEATURE:
<221> NAME/KEY: MOD_RES
<222> LOCATION: (12)..(12)
<223> OTHER INFORMATION: Any hydrophobic amino acid
<220> FEATURE:
<221> NAME/KEY: MOD_RES
<222> LOCATION: (13)..(13)
<223> OTHER INFORMATION: Any basic amino acid

<400> SEQUENCE: 22

```
Xaa Xaa Xaa Xaa Arg Xaa Ser Xaa Xaa Xaa Ser Xaa Xaa
1               5                   10
```

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid

<400> SEQUENCE: 23

```
Xaa Xaa Xaa Xaa Xaa Arg Xaa Ser Xaa Xaa Xaa Ser Xaa Xaa
1               5                   10
```

```
<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid

<400> SEQUENCE: 24

Xaa Xaa Xaa Xaa Xaa Arg Xaa Ser Xaa Xaa Xaa Ser Xaa Xaa Leu
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid

<400> SEQUENCE: 25

Xaa Xaa Xaa Xaa Xaa Arg Xaa Ser Xaa Xaa Xaa Ser Xaa Xaa Leu Ser
1               5                   10                  15

<210> SEQ ID NO 26
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid

<400> SEQUENCE: 26

Xaa Xaa Xaa Xaa Xaa Arg Xaa Ser Xaa Xaa Xaa Ser Xaa Xaa Leu Ser
1               5                   10                  15

Gly

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid

<400> SEQUENCE: 27

Xaa Xaa Xaa Xaa Xaa Arg Xaa Ser Xaa Xaa Xaa Ser Xaa Xaa Leu Ser
1               5                   10                  15
```

Gly Xaa

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid

<400> SEQUENCE: 28

Xaa Xaa Xaa Xaa Xaa Arg Xaa Ser Xaa Xaa Xaa Ser Xaa Xaa Leu Ser
1               5                   10                  15

Gly Xaa Ser

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid

```
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid

<400> SEQUENCE: 29

Xaa Xaa Xaa Xaa Xaa Arg Xaa Ser Xaa Xaa Xaa Ser Xaa Xaa Leu Ser
1               5                   10                  15

Gly Xaa Ser Xaa
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<221> NAME/KEY: MOD_RES
<222> LOCATION: (21)..(21)
<223> OTHER INFORMATION: Any basic amino acid

<400> SEQUENCE: 30

Xaa Xaa Xaa Xaa Xaa Arg Xaa Ser Xaa Xaa Xaa Ser Xaa Xaa Leu Ser
1               5                   10                  15

Gly Xaa Ser Xaa Xaa
            20

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<221> NAME/KEY: MOD_RES
<222> LOCATION: (21)..(22)
<223> OTHER INFORMATION: Any basic amino acid

<400> SEQUENCE: 31

Xaa Xaa Xaa Xaa Xaa Arg Xaa Ser Xaa Xaa Xaa Ser Xaa Xaa Leu Ser
1               5                   10                  15

Gly Xaa Ser Xaa Xaa Xaa
            20

<210> SEQ ID NO 32
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
```

<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<221> NAME/KEY: MOD_RES
<222> LOCATION: (21)..(22)
<223> OTHER INFORMATION: Any basic amino acid

<400> SEQUENCE: 32

Xaa Xaa Xaa Xaa Xaa Arg Xaa Ser Xaa Xaa Xaa Ser Xaa Xaa Leu Ser
1               5                   10                  15

Gly Xaa Ser Xaa Xaa Xaa Asn
            20

<210> SEQ ID NO 33
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<221> NAME/KEY: MOD_RES
<222> LOCATION: (21)..(22)
<223> OTHER INFORMATION: Any basic amino acid
<220> FEATURE:
<221> NAME/KEY: MOD_RES
<222> LOCATION: (24)..(24)
<223> OTHER INFORMATION: Any basic amino acid

<400> SEQUENCE: 33

Xaa Xaa Xaa Xaa Xaa Arg Xaa Ser Xaa Xaa Xaa Ser Xaa Xaa Leu Ser
1               5                   10                  15

Gly Xaa Ser Xaa Xaa Xaa Asn Xaa
            20

<210> SEQ ID NO 34
<211> LENGTH: 34
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 34
gatccatggg tgcccagttc tccaagaccg cagc                                    34

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tctagactct ctgccgcctc cgctgggggg gct                                     33

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gaagcgcttt gccttcaaga agtctttcaa gctga                                   35

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tcagcttgaa agacttcttg aagcaaagcg cttc                                    34

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gaagcctttt ccttcaagaa ggctttcaag ctga                                    34

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tcagcttgaa agccttcttg aaggaaaagc gcttc                                   35

<210> SEQ ID NO 40
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(7)
<223> OTHER INFORMATION: Any amino acid
<220> FEATURE:
<221> NAME/KEY: MOD_RES
<222> LOCATION: (10)..(11)
<223> OTHER INFORMATION: Any amino acid

<400> SEQUENCE: 40

Lys Lys Lys Xaa Xaa Xaa Xaa Lys Lys Xaa Xaa Lys
1               5                   10

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Ser Pro Ser Asn Glu Thr Pro Lys Lys Lys Lys Lys Arg Phe
1               5                   10                  15

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Gly Gln Glu Asn Gly His Val
1               5
```

MPS PEPTIDES AND USE THEREOF

CROSS-REFERENCE TO RELATED APPLICATIONS

This application is a national stage entry under 35 U.S.C. § 371 of International Application No. PCT/US2014/048285, filed Jul. 25, 2014, which in turn claims priority under 35 U.S.C. § 119(e) to U.S. Provisional Application Nos. 61/859,138 and 61/976,443, filed Jul. 26, 2013 and Apr. 7, 2014, respectively, the content of each of which is incorporated herein by reference in its entirety.

STATEMENT OF GOVERNMENT SUPPORT

This invention was made with government support under Grant Nos. 1 RO1 HL077902 and 1 RO1 HL096373 awarded by National Institutes of Health (NIH). The Government has certain rights in the invention.

BACKGROUND

The identification of MARCKS protein dates back to 1982 when it was found that an 87 kDa acidic protein in rat brain nerve endings could be regulated by calcium and calmodulin through the activation of PKC (Wu, W. C. et al. (1982) Proc. Natl. Acad. Sci. USA 79(17):5249-5253). Subsequently, the protein was officially named myristoylated alanine-rich C kinase substrate (MARCKS or MARKS) (Albert, K. A. et al. (1986) Proc. Natl. Acad. Sci. USA 83(9):2822-2826). MARCKS is ubiquitously expressed in various species and tissues (Albert, K. A. et al. (1987) Proc. Natl. Acad. Sci. USA 84(20):7046-7050; Stumpo, D. J. et al. (1989) Proc. Natl. Acad. Sci. USA 86(11):4012-4016), while the other MARCKS family member, MARCKS-related protein (MRP, also known as MacMARCKS, F52 or MLP), a 20 kDa protein is highly expressed in brain, reproductive tissues and macrophage (Aderem, A. (1992) Trend. Biochem. Sci. 17(10):438-443; Blacksher, P. J. (1993) J. Biol. Chem. 268:1501-1504). MRP, similar to MARCKS also contains the same three evolutionarily conserved domains; N-terminus myristoylation domain, multiple homology 2 (MH2) domain, and the effector domain (ED). The MH2 domain of unknown function resembles the cytoplasmic tail of the cation-independent mannose-6-phosphate receptor. Protein phosphorylation occurs at $Ser^{159/163}$ of ED domain. The corporation between the N-terminus (myristoylated) and the ED (phosphorylated or not phosphorylated) is essential for controlling the association of these molecules with membranes.

SUMMARY

This disclosure provides an isolated polypeptide comprising, or alternatively consisting essentially of, or yet further consisting of, no more than 51 amino acids, wherein the amino acid sequence comprises: XXXRYSYXXSYX (SEQ ID NO: 1) or XXXXXRYSYXXSYXLSGYSYXXNXX (SEQ ID NO: 5) and optionally a polynucleotide comprising any contiguous 12 amino acid fragment of SEQ ID NO: 5; and optionally wherein one or more serines (S) of SEQ ID NOs.: 1 or 5, is independently substituted by a neutral or positively charged amino acid, e.g., alanine (A), for example XXXRYAYXXAYX (SEQ ID NO: 11) or XXXXXRYAYXXAYXLAGYAYXXNXX (SEQ ID NO.: 12), and optionally a polynucleotide comprising any contiguous 12 amino acid fragment of SEQ ID NO: 12. In one aspect for the above polypeptides, each X is the same or different and is a basic amino acid and wherein each Y is the same or different and is a hydrophobic amino acid, or an isolated polypeptide comprising a biological equivalent of the sequences noted above and exemplified as SEQ ID NOs: 1, 5, 11 or 12 wherein a biological equivalent of SEQ ID NOs: 1, 5, 11 or 12 comprises a polypeptide that has at least 80% sequence identity to a polypeptide identified above, e.g., SEQ ID NOs: 1, 5, 11 or 12, or wherein a biological equivalent comprises an isolated polypeptide encoded by an an isolated polynucleotide that hybridizes under high stringency conditions to the compliment polynucleotide encoding a polypeptide identified above, or for example, SEQ ID NOs: 1, 5, 11 or 12, or the polynucleotide encoding a polypeptide identified above, e.g., SEQ ID NOs: 1, 5, 11 or 12, and wherein high stringency hybridization conditions is generally performed at about 60° C. in about 1×SSC. In one aspect, the basic amino acid is selected from the group of: lysine, histidine or arginine and the hydrophobic amino acid is selected from the group of alanine, isoleucine, leucine, valine, phenylalanine, tryptophan or tyrosine. In a further aspect, the isolated polypeptides comprise no more than 35 amino acids. The polypeptides and biological equivalents have the ability to: prevent, reduce, delay, inhibit or suppress solid tumor cell growth or metastasis; promote apoptosis; inhibit cancer stem cell growth; inhibit the PIP3 level in the cell; suppress tumor cell mobility; and/or restore sensitivity of a chemoresistant cancer cell to a chemotherapeutic. Without being bound by theory, Applicants believe that the polypeptides of this disclosure directly inhibit MARCKS phosphorylation but also they are believed to indirectly regulate MARCKS expression in cells that express MARCKS. Thus, the polypeptides and other appropriate agents as disclosed herein can be used diagnostically and therapeutically to inhibit MARCKS expression as well when administred in an effective amount for that purpose.

Also provided by this disclosure is an antibody or antibody fragment or derivative of each thereof, wherein the antibody, fragment or derivative binds an isolated polypeptide as described herein.

Further provided is an isolated DNA or RNA polynucleotide, wherein the isolated polynucleotide is selected from the group of an isolated polynucleotide encoding the isolated polypeptide, the antibody, the antibody fragment, the antibody derivative, as described above or its respective compliment, or an isolated polynucleotide that has at least 80% sequence identity to the isolated polynucleotide described herein or its complement, or one that hybridizes under conditions of high stringency to the isolated polynucleotide (or its compliment) as described herein, wherein high stringency hybridization conditions is generally performed at about 60° C. in about 1×SSC.

Also provided is an isolated polynucleotide that comprises, or alternatively consists essentially of, or yet further consists of, an anti-MPS siRNA that inhibits the expression of MARCKS, biological equivalents, as well as DNA that encodes the siRNA and the compliment DNA strand and other biological equivalents.

The polynucleotides can be contained with a vector that optionally comprises regulatory sequences operatively linked thereto for the expression and/or replication of the polynucleotides. The appropriate regulatory sequences, e.g., promoters, will vary with the sequence (DNA or RNA) and the use of the polynucleotide. Host cells, e.g., prokaryotic (*E. coli* or other bacteria), eukaryotic (animal or plant) can comprise the polynucleotides, with or without containment within a vector for expression or replication of the polynucleotides.

Compositions comprising a carrier and one or more of the polypeptides, antibodies, antibody fragments, antibody derivatives, polynucleotides, vectors or host cells are also provided herein. In one aspect, the composition further comprises, or alternatively consists essentially of, or yet further consists of, an agent or small molecule drug, e.g., a chemotherapeutic agent or drug such as a tyrosine kinase inhibitor (TKI), a platinum drug such as cisplatin or a drug or agent that targets EGFR.

The compositions as disclosed herein may be used in the diagnostic, therapeutic and screening methods as disclosed herein, or in the in the preparation of a medicament. Additionally, an additional agent or drug can be combined with the compositions within the same formulation or contained within a separate formulation but administered in combination to a subject in need thereof under appropriate conditions and in therapeutically effective amounts. The medicaments can be used to: prevent, reduce, delay, inhibit or suppress solid tumor cell growth or metastasis; promote apoptosis; inhibit cancer stem cell growth; inhibit the PIP3 level in the cell; restore sensitivity of a chemoresistant cancer cell to a chemotherapeutic; or suppress tumor cell mobility.

This disclosure also provides a method for one or more of: preventing, reducing, delaying, inhibiting or suppressing solid tumor growth or metastasis; promoting apoptosis; inhibiting cancer stem cell growth; inhibiting the level of PIP3 in the cell; or suppressing tumor cell mobility. The method comprises or alternatively consists essentially, or yet further consist of contacting the cell or tissue to be treated with an effective amount of an isolated polypeptide or polynucleotide as described herein or an anti-MPS siRNA that inhibits the expression of MARCKS. The polypeptides, polynucleotides or siRNA may be delivered in the form of a composition. Additionally, a chemotherapeutic agent or drug can be combined with the polypeptide, polynucleotide, and/or siRNA, e.g., a TKI, a platinum drug or a drug that targets EGFR. One of skill in the art can determine if the compositions have accomplished one or more of: preventing, reducing, delaying, inhibiting or suppressing solid tumor growth or metastasis; promoting apoptosis; inhibiting cancer stem cell growth; inhibiting the level of PIP3 in the cell; or suppressing tumor cell mobility, using methods known in the art and those as described herein.

The isolated polypeptides, polynucleotides and isolated siRNA can also be used in a method for restoring sensitivity of a chemoresistant cancer cell to a chemotherapeutic drug by contacting the cell with an effective amount of the isolated polypeptide, polynucleotide or siRNA. In one aspect, the chemotherapeutic drug or agent is selected from a TKI, a platinum drug, or a drug that targets EGFR, cisplatin, paclitaxel, erlotinib or dasatinib; and the chemoresistant cancer cell is a TKI resistant cell. One of skill in the art can determine if sensitivity has been restored using methods known in the art, one of which is described herein.

Further provided are method for providing in a subject, one or more of: preventing, reducing, delaying, inhibiting or suppressing solid tumor growth or metastasis; promoting apoptosis; inhibiting cancer stem cell growth; suppressing tumor cell mobility; inhibiting the level of PIP3 in a cell in a subject in need thereof, the method comprising, or alternatively consisting essentially of, or yet further consisting of, administering to the subject an effective amount of the isolated polypeptide, isolated polynucleotide, and/or an anti-MPS siRNA that inhibits the expression of MARCKS, or an equivalent of each thereof, or a composition containing the same. One of skill in the art can determine if the compositions have accomplished one or more of: preventing, reducing, delaying, inhibiting or suppressing solid tumor growth or metastasis; promoting apoptosis; inhibiting cancer stem cell growth; inhibiting the level of PIP3 in the cell; or suppressing tumor cell mobility, using methods known in the art and those as described herein. The method can further comprise, or alternatively consist essentially of, or yet further consist of, administration of an effective amount of a chemotherapeutic drug, e.g., a TKI, a platinum drug or a drug that targets EGFR. In one aspect, the chemotherapeutic drug or agent is selected from cisplatin, paclitaxel, erlotinib or dasatinib.

Further provided is a method for restoring sensitivity of a chemoresistant tumor cell to a chemotherapeutic drug in subject in need thereof, comprising, or alternatively consisting essentially of, or yet further consisting of, administering to the subject in need thereof an effective amount of an isolated polypeptide, isolated polynucleotide, and/or siRNA as described above.

Kits are also provided. The kits can comprise one or more of the isolated polypeptides, and/or antibody, antibody fragment, or antibody derivative, the isolated polynucleotide, the vector, or the composition as described above and optionally, instructions for use.

Yet further provided is a method to identify a patient suffering from, is more likely to suffer from, a more aggressive cancer stage (Stage II to IV) or a metastatic cancer, the method comprising, or alternatively consisting essentially of, or yet further consisting or, determining the level of phosphorylated MARCKS levels (p-MARCKS level) in a sample of a tumor cell isolated from the patient, wherein a high expression level as compared to a control or predetermined value indicates that the patient is more likely to suffer from a more aggressive cancer stage or metastatic cancer, and a low expression level as compared to a suitable control or predetermined value indicates that the patient is less likely to experience a less aggressive cancer stage or metastasis. The method can further comprise administering to a patient identified as having cancer or metastasis an effective amount of an appropriate therapy.

Diagnostic procedures can also be performed in situ directly upon tissue sections (fixed and/or frozen) of primary tissue such as biopsies obtained from biopsies or resections. The data establishing the noted association is appended to this disclosure and incorporated by reference herein.

In one aspect, the sample is a tumor sample isolated from the patient and the method of determining p-MARCKS level is by contacting the sample with a suitable antibody (e.g., a p-MARCKS monoclonal antibody (anti-p-SER 159/163) that specifically recognizes and binds p-MARCKS, and quantitating the p-MARCKS level by immunohistochemical analysis (IHC). The cancer is any one or more of lung cancer (e.g., NSCLC), colon cancer, colorectal cancer, breast cancer or pancreatic cancer.

In one aspect, the patient is a mammal such as an equine, murine, feline, canine, or human patient. In another aspect, the patient is a human patient. In a further aspect, the suitable control is the p-MARCKS level in a patient sample that does not exhibit one or more of a more aggressive cancer stage or metastasis.

With this knowledge, a physician can determine the most appropriate therapy for the patient. This disclosure further provides administering an effective amount of a more aggressive therapy (e.g., chemotherapeutic agents such as TKIs, a platinum drug or EGFR inhibitors or an agent that targets EGFR) to the patient.

BRIEF DESCRIPTION OF THE FIGURES

FIG. 20 shows normal human bronchial epithelial cells were exposed to the indicated concentrations of either MPS or mutant (Mut) peptide. After 72 hours of peptide treatment, the number of viable cells was visualized by using crystal violet staining. A representative of three independent experiments.

FIG. 21 shows cell lines and their properties that were used in a study for peptide treatment (Buck, E. et al. (2006) Mol Cancer Ther. 2006; 5:2676-2684; Sos, M. L. et al. (2009) Cancer Res. 69:3256-3261; Hong, T. M. et al. (2000) Am. J. Respir. Cell Mol. Biol. 23:355-363; Garon, E. B. et al. (2010) Mol. Cancer Ther. 9:1985-1994).

FIG. 22 shows H1975 and H1650 cells were treated with the indicated concentrations of MPS peptide and colonies were counted after 10 days of treatment using crystal violet staining. Data are representative of three independent experiments.

(2003) Biophys. J. 85:2442-2448; McLaughlin, S. et al. (2005) Nature 438:605-611). Figure discloses "MH" domain as SEQ ID NO: 42. (B) MPS and the alanines-substituted (A-Mut) peptide have greater peptide-cell interaction, as compared to the aspartates-substituted (D-Mut) peptide. MPS peptide, D-Mut, and A-Mut MPS peptide were labeled with NBD (4-Chloro-7-Nitrobenz-2-Oxa-1,3-Diazole) dye. After purification of peptides, CL1-0 cells were treated with various NBD-labeled peptides and then subjected to DAPI staining. The NBD-labeled peptide (green) and nucleus counter-stain (blue) were visualized via confocal laser-scanning microscopy. Purified reagent with no peptide (Con) used as a negative control. (C) Determination of MARCKS phosphorylation levels after MPS peptide treatment. Lysates from various WS-related peptide-treated H1975 cells were subjected to Western blot analysis. Con, untreated cells.

Figure 29:
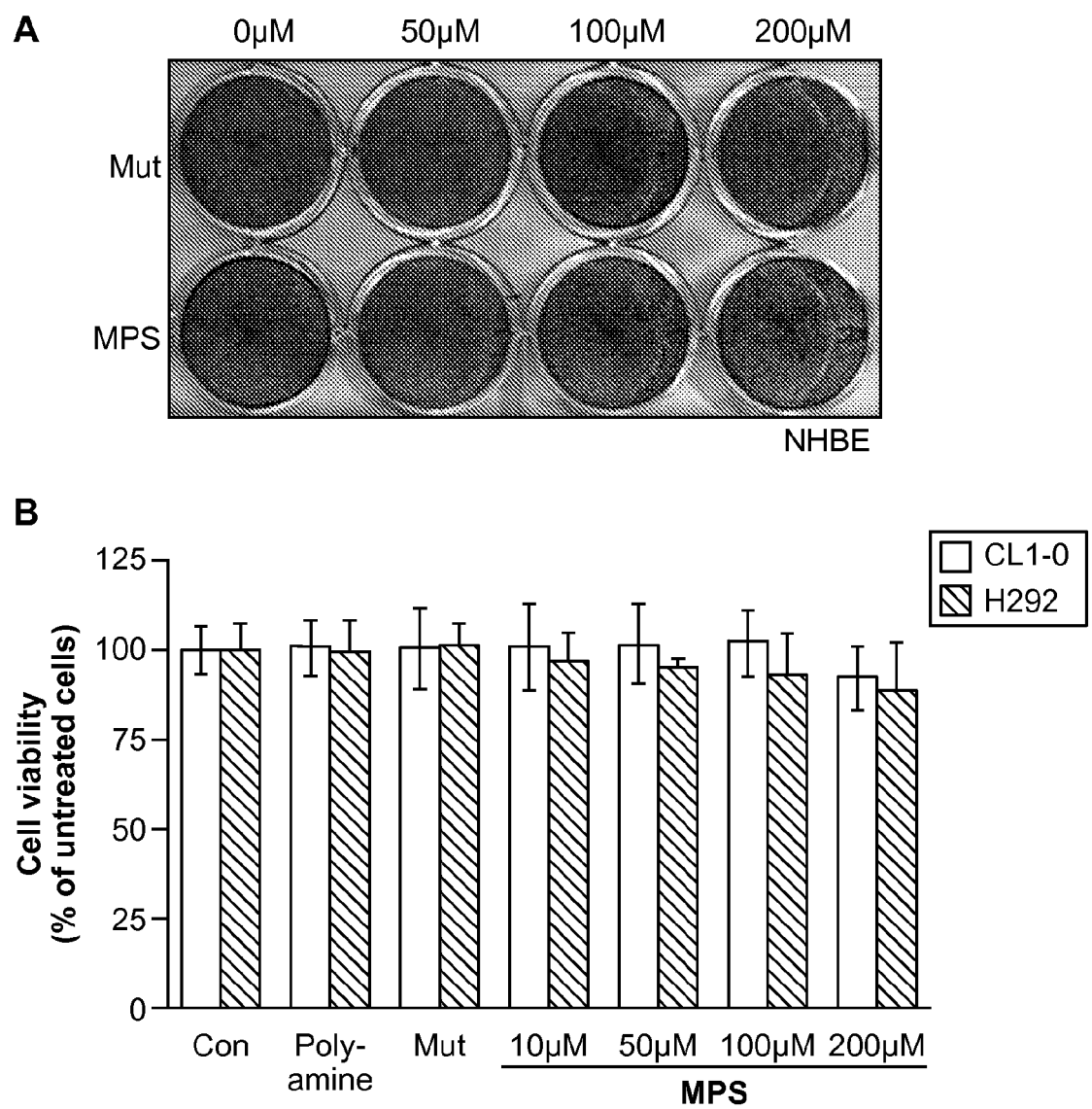

FIG. 29A shows normal human bronchial epithelial cells were exposed to the indicated concentrations of either MPS or aspartates-substituted mutant (Mut) peptide. After 72 hours of peptide treatment, the number of viable cells was visualized by using crystal violet staining. A representative example of three independent experiments is shown. FIG. 29B shows cell viability analysis of two lung cancer cell lines with low phospho-MARCKS levels upon MPS treatment. Cells were incubated with various concentrations of MPS peptide for 72 hours and then subjected to MTS assays. 200 µM polyamine and aspartates-substituted mutant (Mut) peptide served as peptide controls (n=3).

Figure 30:
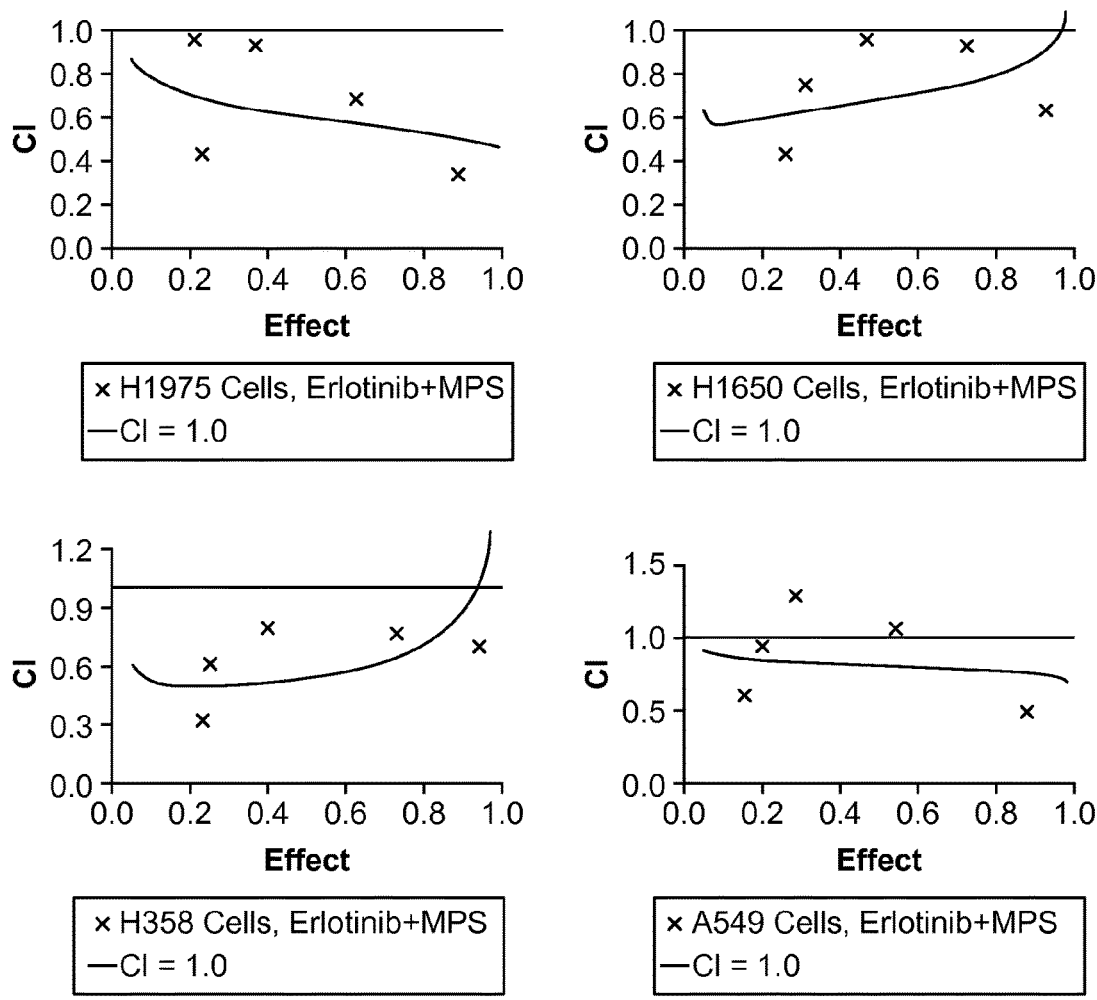

FIG. 30 shows combination effect of EGFR inhibitor erlotinib and MPS peptide on H1975, H1650, H358 and A549 cells. Four cell lines were treated with various doses of erlotinib (0.625-10 µM) and/or MPS peptide (12.5-200 µM) for 72 hours, respectively. After single or combined treatment, cell viability was determined by MTS assays. The Chou and Talalay CI (combination index) method was used to evaluate the therapeutic interactions between erlotinib and MPS peptide. The Fa-CI plots were constructed using the Calcusyn software. Fa-CI plot represents the CI values and the Fa at different concentrations of erlotinib (from 0.625 µM to 10 µM) in cells combined treatment with MPS peptide (from 12.5 µM to 200 µM). Dashed line, additive effect of the combination of MPS peptide and the drug is represented at CI=1. A CI of <1 denotes a synergistic interaction, a CI of ~1 denotes an additive interaction, and a CI of >1 indicates an antagonistic interaction. The experimental values of the fixed dose ratios of erlotinib/MPS combinations (cross symbol) were most below the respective additive points.

Figure 31:
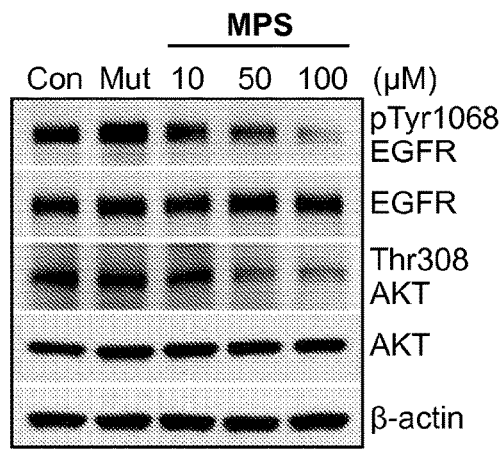

FIG. 31 shows determination of EGFR and AKT phosphorylation levels after 48 hours of MPS peptide treatment. Lysates from 10-100 µM MPS peptide-treated H1975 cells were subjected to Western blot analysis.

DETAILED DESCRIPTION

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; and Mayer and Walker eds. (1987) Immunochemical Methods in Cell and Molecular Biology (Academic Press, London).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

Definitions

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to nucleic acids, such as DNA or RNA, refers to molecules separated from other DNAs or RNAs, respectively that are present in the natural source of the macromolecule. The term "isolated peptide fragment" is meant to include peptide fragments which are not naturally occurring as fragments and would not be found in the natural state. The term "isolated" is also used herein to refer to polypeptides and proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

The term "binding" or "binds" as used herein are meant to include interactions between molecules that may be detected using, for example, a hybridization assay. The terms are also meant to include "binding" interactions between molecules. Interactions may be, for example, protein-protein, antibody-protein, protein-nucleic acid, protein-small molecule or small molecule-nucleic acid in nature. This binding can result in the formation of a "complex" comprising the interacting molecules. A "complex" refers to the binding of two or more molecules held together by covalent or non-covalent bonds, interactions or forces.

The term "MPS" intends a polypeptide of no more than 51 amino acids, comprising, or alternatively consisting essentially of, or yet consisting of, an isolated polypeptide comprising, or alternatively consisting essentially of, or yet further consisting of, no more than 51 amino acids, wherein the amino acid sequence comprises the amino acid sequence: XXXRYSYXXSYX (SEQ ID NO: 1) or XXXXXRYSYXXSYXLSGYSYXXNXX (SEQ ID NO: 5), and optionally a polynucleotide comprising any contiguous 12 amino acid fragment of SEQ ID NO:5 and biological equivalents of each thereof; and wherein in one aspect, one or more of the serines (S) are substituted with one or more neutral or positively charged amino acids, that may be the same or different, e.g., alanines (A) or a biological equivalent of each thereof, wherein a biological equivalent of comprises a polypeptide that has at least 80% sequence identity to the above polypeptides or amino acid sequences, or wherein a biological equivalent comprises an isolated polypeptide encoded by an isolated polynucleotide that hybridizes under high stringency conditions to the compliment polynucleotide encoding these polypeptide(s) or the polynucleotide encoding these polypeptides, and wherein high stringency hybridization conditions is generally performed at about 60° C. in about 1×SSC. In one aspect, term also includes the polypeptides having the amino acid sequences XXXRYAYXXAYX (SEQ ID NO: 11) or XXXXXRYAYXXAYXLAGYAYXXNXX (SEQ ID NO.: 12), and optionally a polynucleotide comprising any contiguous 12 amino acid fragment of SEQ ID NO: 12 and biological equivalents thereof; and further optionally wherein one or more serine (S) is substituted with one or more neutral or positively charged amino acids, that may be the same or different, e.g., one or more serines are substituted with one or more alanines (A), and wherein each X is the same or different and is a basic amino acid and wherein each Y is the same or different and is a hydrophobic amino acid. Non-limiting examples of MPS polypeptides include an isolated polypeptide comprising a biological equivalent of SEQ ID NOs: 1, 5, 11 or 12 and in one aspect, wherein one or more serine (S) is substituted with one or more neutral or positively charged amino acids, that may be the same or different, e.g., one or more serines are substituted with one or more alanines (A), and wherein a biological equivalent of SEQ ID NOs: 1, 5, 11 or 12 and optionally wherein one or more serine (S) is substituted with one or more neutral or positively charged amino acids, that may be the same or different, e.g., one or more serines are substituted with one or more alanines (A), and comprises a polypeptide that has at least 80% sequence identity to SEQ ID NOs: 1, 5, 11 or 12, and optionally wherein one or more serine (S) is substituted with one or more neutral or positively charged amino acids, that may be the same or different, e.g., one or more serines are substituted with one or more alanines (A), and or wherein a biological equivalent comprises an isolated polypeptide encoded by an an isolated polynucleotide that hybridizes under high stringency conditions to the compliment polynucleotide encoding SEQ ID NOs: 1, 5, 11 or 12, and optionally wherein one or more serine (S) is substituted with one or more neutral or positively charged amino acids, that may be the same or different, e.g., one or more serines are substituted with one or more alanines (A), and or the polynucleotide encoding SEQ ID NOs: 1, 5, 11 or 12, and optionally wherein one or more serine (S) is substituted with one or more neutral or positively charged amino acids, that may be the same or different, e.g., one or more serines are substituted with one or more alanines (A), and wherein high stringency hybridization conditions is generally performed at about 60° C. in about 1×SSC. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, the polypeptides as described above are no more than 45 amino acids, or alternatively 40 amino acids, or alternatively 35 amino acids, or alternatively 30 amino acids, or alternatively no more than 25 amino acids, or alternatively no more than 20 amino acids, or alternatively no more than 15 amino acids or alternatively, the polypeptides of SEQ ID NO: 1, 5 11 or 12, and optionally wherein one or more serine (S) is substituted with one or more neutral or positively charged amino acids, that may be the same or different, e.g., one or more serines are substituted with one or more alanines (A), and wherein biological equivalents of each thereof. In one aspect, the MPS peptide comprises, or consists essentially of, an amino acid sequence selected from KKKRFSFKKSFK (SEQ ID NO: 2).
KKKKRFSFKKSFK (SEQ ID NO: 3),
KKKR(A/I/L/V/W/Y)S(A/I/L/V/W/Y)KKS(A/I/L/V/W/Y)K (SEQ ID NO: 4);
$(H/R)_3RFSF(H/R)_2SF(H/R)$ (SEQ ID NO: 6);
KKKKKR(A/I/L/V/W/Y)S(A/I/L/V/W/Y)KKS(A/I/L/V/W/Y)KLSGFSFKKNKK (SEQ ID NO: 7);
$(H/R)_5RFSF(H/R)_2SF(H/R)LSGFSF(H/R)_2N(H/R)_2$ (SEQ IN NO: 8);
KKKKKRFSFKKSFKLSGFSFKKNKK (SEQ ID NO: 9); and optionally a polynucleotide comprising any contiguous 12 amino acid fragment of SEQ ID NO: 9 and biological equivalents thereof; and further optionally wherein one or more serine (S) is substituted with one or more neutral or positively charged amino acids, that may be the same or different, e.g., one or more serines are substituted with one or more alanines (A), for example, KKKKKRFAFKKAFKLAGFAFKKNKK (SEQ ID NO: 10) and optionally any contiguous 12 amino acid fragment of SEQ ID NO: 10 and biological equivalents thereof; and;
XXXRYAYXXAYX (SEQ ID NO: 11);
XXXXXRYAYXXAYXLAGYAYXXNXX (SEQ ID NO: 12) and optionally a polynucleotide comprising any contiguous 12 amino acid fragment of SEQ ID NO: 12 and biological equivalents thereof;
KKKRFAFKKAFK (SEQ ID NO: 13),
and biological equivalents of each thereof, wherein a biological equivalent of SEQ ID NOs: 1 to 13 (and optionally, wherein one or more serine (S) is substituted with one or more neutral or positively charged amino acids, that may be the same or different, e.g., one or more serines are substituted with one or more alanines (A)), and comprises a polypeptide that has at least 80% sequence identity to SEQ ID NOs: 1 to 13 and optionally, wherein one or more serine (S) is substituted with one or more neutral or positively charged amino acids, that may be the same or different, e.g., one or more serines are substituted with one or more alanines (A), and, or wherein a biological equivalent of SEQ ID NOs: 1 to 13 comprises an isolated polypeptide encoded by an isolated polynucleotide that hybridizes under conditions of high stringency to a polynucleotide encoding SEQ ID NOs: 1 to 13, and optionally wherein one or more serine (S) is substituted with one or more neutral or positively charged amino acids, that may be the same or different, e.g., one or more serines are substituted with one or more alanines (A), respectively or the complement of these polynucleotides encoding the polypeptides, wherein high stringency hybridization conditions is generally performed at about 60° C. in about 1×SSC. A biological equivalent also includes a polypeptide having at least 80% amino acid sequence identity to a polypeptide having an amino acid sequence of SEQ ID NOs: 1 to 13 and optionally wherein one or more serine (S) is substituted with one or more neutral or positively charged amino acids, that may be the same or different, e.g., one or more serines are substituted with one or more alanines (A).

In a further aspect, an MPS polypeptide comprises an amino acid sequence selected from
XXXRYSYXXSYX (SEQ ID NO: 21);
XXXXRYSYXXSYX (SEQ ID NO: 22);
XXXXXRYSYXXSYX (SEQ ID NO: 23);
XXXXXRYSYXXSYXL (SEQ ID NO: 24);
XXXXXRYSYXXSYXLS (SEQ ID NO: 25);
XXXXXRYSYXXSYXLSG (SEQ ID NO: 26);
XXXXXRYSYXXSYXLSGY (SEQ ID NO: 27);
XXXXXRYSYXXSYXLSGYS (SEQ ID NO: 28);
XXXXXRYSYXXSYXLSGYSY (SEQ ID NO: 29);
XXXXXRYSYXXSYXLSGYSYX (SEQ ID NO: 30);
XXXXXRYSYXXSYXLSGYSYXX (SEQ ID NO: 31);
XXXXXRYSYXXSYXLSGYSYXXN (SEQ ID NO: 32);
XXXXXRYSYXXSYXLSGYSYXXNX (SEQ ID NO: 33),
and wherein one or more serine (S) is substituted with one or more neutral or positively charged amino acids, that may be the same or different, wherein in one aspect for each of SEQ ID NOs: 21 to 33, one or more serines is substituted with an alanine, and wherein X and Y are as defined above, as well as biological equivalents of each thereof, wherein a wherein a biological equivalent of comprises a polypeptide that has at least 80% sequence identity to the above noted polypeptide amino acid sequences (as well as those noted to be substited with one or more alanines), or wherein a biological equivalent comprises an isolated polypeptide encoded by an isolated polynucleotide that hybridizes under high stringency conditions to the compliment polynucleotide encoding these polypeptides (as well as those noted to be substited with one or more alanines), or the polynucleotide encoding these polypeptides (as well as those noted to be substited with one or more neutral or positively charged amino acids, e.g, alanines), and wherein high stringency hybridization conditions is generally performed at about 60° C. in about 1×SSC.

The MPS polypeptides and biological equivalents have the ability to: prevent, reduce, delay, inhibit or suppress solid tumor cell growth or metastasis; promote apoptosis; inhibit cancer stem cell growth; inhibit the PIP3 level in the cell; suppress tumor cell mobility; and/or restore sensitivity of a chemoresistant cancer cell to a chemotherapeutic. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, the polypeptide is no more than 45 amino acids, or alternatively 40 amino acids, or alternatively 35 amino acids, or alternatively 30 amino acids, or alternatively no more than 25 amino acids, or alternatively no more than 20 amino acids, or alternatively no more than 15 amino acids or alternatively.

In one aspect, the polypeptides of SEQ ID NOs: 10 and 11, as compared to SEQ ID NOs: 2 and 9, are MPS polypeptides wherein the 4 serine residues of wild-type MPS peptide are replaced by alanine residues, e.g., (KKKK-KRFAFKKAFKLAGFAFKKNKK (SEQ ID NO: 10), that increases membrane affinity. The polypeptides of SEQ ID NO: 9-13 are highly positive charged and interact electrostatically with PIP2 on the phospholipid membrane. Similar to SEQ ID NO: 9, the polypepeptide of SEQ ID NO: 10 is to get into cancer cells and reduce phospho-MARCKS levels. The MPS polypeptide of SEQ ID NO: 10 is shown to have greater peptide-cell interaction and better anti-cancer activity, as compared to the MPS peptide of SEQ ID NO: 9.

The term "polypeptide" is used interchangeably with the term "protein" and "peptide" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. In one aspect, the polypeptides contain unnatural or synthetic amino acids, including glycine and both the D and L optical isomers of naturally occurring amin acids, amino acid analogs and peptidomimetics. A peptide of three or more amino acids is commonly called an oligopeptide if the peptide chain is short. If the peptide chain is long, the peptide is commonly called a polypeptide or a protein. The term "peptide fragment," as used herein, also refers to a peptide chain.

The phrase "biologically equivalent polypeptide" or "biologically equivalent peptide fragment" refers to protein, polynucleotide, or peptide fragment encoded by a polynucleotide that hybridizes to a polynucleotide encoding the exemplified polypeptide or its complement of the polynucleotide encoding the exemplified polypeptide, under high stringency and which exhibit similar biological activity in vivo, e.g., approximately 100%, or alternatively, over 90% or alternatively over 85% or alternatively over 70%, as compared to the standard or control biological activity. Additional embodiments within the scope of this invention are identified by having more than 60%, or alternatively, more than 65%, or alternatively, more than 70%, or alternatively, more than 75%, or alternatively, more than 80%, or alternatively, more than 85%, or alternatively, more than 90%, or alternatively, more than 95%, or alternatively more than 97%, or alternatively, more than 98% or 99% sequence homology. Percentage homology can be determined by sequence comparison using programs such as BLAST run under appropriate conditions. In one aspect, the program is run under default parameters.

The term "polynucleotide" refers to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, or EST), exons, introns, messenger RNA (mRNA), transfer RNA, ribosomal RNA, ribozymes, cDNA, RNAi, siRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" are synonymously and refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code =standard; filter =none; strand =both; cutoff =60; expect =10; Matrix =BLOSUM62; Descriptions =50 sequences; sort by =HIGH SCORE; Databases =non-redundant, GenBank +EMBL +DDBJ +PDB +GenBank CDS translations +SwissProtein +SPupdate +PIR. Details of these programs can be found at the following Internet address: ncbi.nlm.nih.gov, last accessed on Nov. 26, 2007. Biologically equivalent polynucleotides are those having the specified percent homology and encoding a polypeptide having the same or similar biological activity.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product such as RNA or a polypeptide or protein.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

A "gene product" or alternatively a "gene expression product" refers to the RNA when a gene is transcribed or amino acid (e.g., peptide or polypeptide) generated when a gene is transcribed and translated.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

Applicants have provided herein the polypeptide and/or polynucleotide sequences for use in gene and protein transfer and expression techniques described below. It should be understood, although not always explicitly stated that the sequences provided herein can be used to provide the expression product as well as substantially identical sequences that produce a protein that has the same biological properties. These "biologically equivalent" or "biologically active" polypeptides are encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical primary amino acid sequence to the reference polypeptide when compared using sequence identity methods run under default conditions. Specific polypeptide sequences are provided as examples of particular embodiments. Modifications to the sequences to amino acids with alternate amino acids that have similar charge.

A "gene delivery vehicle" is defined as any molecule that can carry inserted polynucleotides into a host cell. Examples of gene delivery vehicles are liposomes, micelles, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide of this invention can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Publication No. WO 95/27071. Ads do not require integration into the host cell genome. Recombinant Ad derived vectors, particularly those that reduce the potential for recombination and generation of wild-type virus, have also been constructed. See, International PCT Publication Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this invention are other non-limiting techniques.

The terms "culture" or "culturing" refer to the in vitro propagation of cells or organisms on or in media of various kinds. It is understood that the descendants of a cell grown in culture may not be completely identical (i.e., morphologically, genetically, or phenotypically) to the parent cell.

The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. As used herein the terms "antibodies" and "immunoglobulin" include antibodies or immunoglobulins of any isotype, fragments of antibodies which retain specific binding to antigen, including, but not limited to, Fab, Fab', F(ab)$_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated CDRs or a functional paratope; chimeric antibodies, humanized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

Monoclonal antibodies may be generated using hybridoma techniques or recombinant DNA methods known in the art. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods to making these antibodies are described herein.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

As used herein, chimeric antibodies are antibodies whose light and heavy chain genes have been constructed, typically by genetic engineering, from antibody variable and constant region genes belonging to different species.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin. a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include:glycine-alanine, valine-leucine-isoleucine, phenylalanine-tyrosine, lysine-arginine, alanine-valine, serine-threonine and asparagine-glutamine.

As used herein, the term "antibody derivative", comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof.

A "composition" is intended to mean a combination of active polypeptide, polynucleotide or antibody and another compound or composition, inert (e.g. a detectable label) or active (e.g. a gene delivery vehicle) alone or in combination with a carrier which can in one embodiment be a simple carrier like saline or pharmaceutically acceptable or a solid support as defined below.

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

The phrase "solid support" refers to non-aqueous surfaces such as "culture plates" "gene chips" or "microarrays." Such gene chips or microarrays can be used for diagnostic and therapeutic purposes by a number of techniques known to one of skill in the art. In one technique, oligonucleotides are arrayed on a gene chip for determining the DNA sequence by the hybridization approach, such as that outlined in U.S. Pat. Nos. 6,025,136 and 6,018,041. The polynucleotides of this invention can be modified to probes, which in turn can be used for detection of a genetic sequence. Such techniques have been described, for example, in U.S. Pat. Nos. 5,968, 740 and 5,858,659. A probe also can be affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Various "gene chips" or "microarrays" and similar technologies are known in the art. Examples of such include, but are not limited to, LabCard (ACLARA Bio Sciences Inc.); GeneChip (Affymetric, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.); a thermal jet spotting system (Hewlett Packard Company); Hyseq HyChip (Hyseq, Inc.); BeadArray (Illumina, Inc.); GEM (Incyte Microarray Systems); a high-throughput microarrying system that can dispense from 12 to 64 spots onto multiple glass slides (Intelligent Bio-Instruments); Molecular Biology Workstation and Nano-Chip (Nanogen, Inc.); a microfluidic glass chip (Orchid biosciences, Inc.); BioChip Arrayer with four PiezoTip piezoelectric drop-on-demand tips (Packard Instruments, Inc.); FlexJet (Rosetta Inpharmatic, Inc.); MALDI-TOF mass spectrometer (Sequnome); ChipMaker 2 and ChipMaker 3 (TeleChem International, Inc.); and GenoSensor (Vysis, Inc.) as identified and described in Heller (2002) Annu Rev. Biomed. Eng. 4:129-153. Examples of "gene chips" or a "microarrays" are also described in U.S. Patent Publication Nos.: 2007/0111322, 2007/0099198, 2007/0084997, 2007/0059769 and 2007/0059765 and U.S. Pat. Nos. 7,138,506, 7,070,740, and 6,989,267.

In one aspect, "gene chips" or "microarrays" containing probes or primers homologous to a polynucleotide, polypeptide or antibody described herein are prepared. A suitable sample is obtained from the patient, extraction of genomic DNA, RNA, protein or any combination thereof is conducted and amplified if necessary. The sample is contacted to the gene chip or microarray panel under conditions suitable for hybridization of the gene(s) or gene product(s) of interest to the probe(s) or primer(s) contained on the gene chip or microarray. The probes or primers may be detectably labeled thereby identifying the gene(s) of interest. Alternatively, a chemical or biological reaction may be used to identify the probes or primers which hybridized with the DNA or RNA of the gene(s) of interest. The genotypes or phenotype of the patient is then determined with the aid of the aforementioned apparatus and methods.

Other non-limiting examples of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding protein, peptide, antibody or antigen, or will be able to ascertain the same by use of routine experimentation.

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

"Cell," "host cell" or "recombinant host cell" are terms used interchangeably herein. It is understood that such terms refer not only to the particular subject cell but to the progeny or potential progeny of such a cell. The cells can be of any one or more of the type murine, rat, rabbit, simian, bovine, ovine, porcine, canine, feline, equine, and primate, particularly human. Because certain modifications may occur in succeeding generations due to either mutation or environmental influences, such progeny may not, in fact, be identical to the parent cell, but are still included within the scope of the term as used herein.

The terms "disease" and "disorder" are used inclusively and refer to any condition associated with cancer. As used herein, "cancer" may refer both to precancerous cells as well as cancerous cells of a tumor such as a solid tumor.

"Treating," "treatment," or "ameliorating" of a disease includes: (1) preventing the disease, i.e., causing the clinical symptoms of the disease not to develop in a patient that may be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The term "suffering" as it related to the term "treatment" refers to a patient or individual who has been diagnosed with or is predisposed to a disease. A patient may also be referred to being "at risk of suffering" from a disease. This patient has not yet developed characteristic disease pathology, however are known to be predisposed to the disease due to family history, being genetically predispose to developing the disease, or diagnosed with a disease or disorder that predisposes them to developing the disease to be treated.

"High level" or "low level" refers to increased or decreased p-MARCKS level in a test sample as compared to the p-MARCKS level in the control sample. In one aspect, the test sample is a tumor sample, and the control sample is a normal cell. In yet another aspect, the test sample is a sample from a patient, and the control sample is a similar sample a patient that experience a more favorable outcome.

A "predetermined value" for p-MARCKS level is so chosen that a patient with a p-MARCKS level higher than the predetermined value is likely to experience a less desirable clinical outcome than patients with p-MARCKS levels lower than the predetermined value, or vice-versa. p-MARCKS levels are determined by the Applicants to be associated with clinical outcomes. One of skill in the art can determine a predetermined value for a gene or its expression product by comparing expression levels of a p-MARCKS level in patients with more desirable clinical outcomes to those with less desirable clinical outcomes. In one aspect, a predetermined value is a p-MARCKS level that best separates patients into a group with more desirable clinical outcomes and a group with less desirable clinical outcomes. Such an expression value can be mathematically or statistically determined with methods well known in the art.

"An effective amount" intends to indicate the amount of a compound or agent administered or delivered to the patient which is most likely to result in the desired response to treatment. The amount is empirically determined by the patient's clinical parameters including, but not limited to the stage of disease, age, gender, histology, sensitivity, toxicity and likelihood for tumor recurrence.

As used herein, the terms "Stage I cancer," "Stage II cancer," "Stage III cancer," and "Stage IV" refer to the TNM staging classification for cancer. Stage I cancer typically identifies that the primary tumor is limited to the organ of origin. Stage II intends that the primary tumor has spread into surrounding tissue and lymph nodes immediately draining the area of the tumor. Stage III intends that the primary tumor is large, with fixation to deeper structures. Stage IV intends that the primary tumor is large, with fixation to deeper structures. See pages 20 and 21, CANCER BIOLOGY, $2^{nd}$ Ed., Oxford University Press (1987).

"Having the same cancer" is used when comparing one patient to another or alternatively, one patient population to another patient population. For example, the two patients or patient populations will each have or be suffering from colon cancer.

A "tumor" is an abnormal growth of tissue resulting from uncontrolled, progressive multiplication of cells and serving no physiological function. A "tumor" is also known as a neoplasm.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, the disease being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, inhalation, injection, and topical application.

An agent of the present invention can be administered for therapy by any suitable route of administration. It will also be appreciated that the preferred route will vary with the condition and age of the recipient, and the disease being treated.

A tyrosine kinase inhibitor ("TKI") is an agent (small molecule or biologic) that inhibits the action of tyrosine kinase in a cell. Tyrosine kinases are enzymes that are responsible for the activation of many proteins by signal transduction cascades. TKIs are typically used as anti-cancer drugs. Examples of tyrosine kinase inhibitors include, but are not limited to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib); FLT3 (Lestaurtinib); PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib). Small molecule TKIs are known in the art and listed at the web address comprising oncolink.org/treatment/article.cfm?id=452 (last accessed on Jul. 17, 2014).

PTK/ZK is a "small" molecule tyrosine kinase inhibitor with broad specificity that targets all VEGF receptors (VEGFR), the platelet-derived growth factor (PDGF) receptor, c-KIT and c-Fms. Drevs (2003) Idrugs 6(8):787-794. PTK/ZK is a targeted drug that blocks angiogenesis and lymphangiogenesis by inhibiting the activity of all known receptors that bind VEGF including VEGFR-1 (Flt-1), VEGFR-2 (KDR/Flk-1) and VEGFR-3 (Flt-4). The chemical names of PTK/ZK are 1-[4-Chloroanilino]-4-[4-pyridylmethyl]phthalazine Succinate or 1-Phthalazinamine, N-(4-chlorophenyl)-4-(4-pyridinylmethyl)-, butanedioate (1:1). Synonyms and analogs of PTK/ZK are known as Vatalanib, CGP79787D, PTK787/ZK 222584, CGP-79787, DE-00268, PTK-787, PTK-787A, VEGFR-TK inhibitor, ZK 222584 and ZK.

As used herein, the term "platinum drug" intends an anticancer drug that is a platinum based compound which is a subclass of DNA alkylating agents. Such agents are well known in the art and are used to treat a variety of cancers, such as, lung cancers, head and neck cancers, ovarian cancers, colorectal cancer and prostate cancer. Non-limiting examples of such agents include carboplatin, cisplatin, nedaplatin, oxaliplatin, triplatin tetranitrate, Satraplatin, Aroplatin, Lobaplatin, and JM-216. (see McKeage et al. (1997) J. Clin. Oncol. 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

"Oxaliplatin" (Eloxatin®) is a platinum-based chemotherapy drug in the same family as cisplatin and carboplatin. It is typically administered in combination with fluorouracil and leucovorin in a combination known as FOLFOX for the treatment of colorectal cancer. Compared to cisplatin the two amine groups are replaced by cyclohexyldiamine for improved antitumour activity. The chlorine ligands are replaced by the oxalato bidentate derived from oxalic acid in order to improve water solubility. Equivalents to Oxaliplatin are known in the art and include without limitation cisplatin, carboplatin, aroplatin, lobaplatin, nedaplatin, and JM-216 (see McKeage et al. (1997) J. Clin. Oncol. 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

Descriptive Embodiments
Isolated Polypeptides and Compositions

This disclosure provides an isolated MPS polypeptide, wherein the MPS polypeptide comprises no more than 51 amino acids and wherein the amino acid comprises the amino acid sequences: XXXRYSYXXSYX (SEQ ID NO: 1) or XXXXXRYSYXXSYXLSGYSYXXNXX (SEQ ID NO: 5), and optionally wherein one or more serine (S) is substituted with one or more neutral or positively charged amino acids, that may be the same or different, e.g., one or more serines are substituted with one or more alanines (A), and isolated polypeptides wherein the polypeptides have one or more serines substituted with one or more alanines, and biological equivalents of each thereof (as described herein) or XXXRYAYXXAYX (SEQ ID NO: 11) or XXXXXRYAYXXAYXLAGYAYXXNXX (SEQ ID NO.: 12), and optionally wherein one or more serine (S) is substituted with one or more neutral or positively charged amino acids, that may be the same or different, e.g., one or more serines are substituted with one or more alanines (A), wherein each X is the same or different and is a basic amino acid and wherein each Y is the same or different and is a hydrophobic amino acid, or an isolated polypeptide comprising a biological equivalent of SEQ ID NOs: 1, 5, 11 or 12, and optionally wherein one or more serine (S) is substituted with one or more neutral or positively charged amino acids, that may be the same or different, e.g., one or more serines are substituted with one or more alanines (A), wherein a biological equivalent of SEQ ID NOs: 1, 5, 11 or 12, and optionally wherein one or more serine (S) is substituted with one or more neutral or positively charged amino acids, that may be the same or different, e.g., one or more serines are substituted with one or more alanines (A), comprises a polypeptide that has at least 80% sequence identity to SEQ ID NOs: 1, 5, 11 or 12, and optionally wherein one or more serine (S) is substituted with one or more neutral or positively charged amino acids, that may be the same or different, e.g., one or more serines are substituted with one or more alanines (A), wherein a biological equivalent comprises an isolated polypeptide encoded by an isolated polynucleotide that hybridizes under high stringency conditions to the compliment polynucleotide encoding these polypeptides, or the polynucleotide encoding these polypeptides and wherein high stringency hybridization conditions is generally performed at about 60° C. in about 1×SSC. In another aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, the polypeptide is no more than 45 amino acids, or alternatively 40 amino acids, or alternatively 35 amino acids, or alternatively 30 amino acids, or alternatively no more than 25 amino acids, or alternatively no more than 20 amino acids, or alternatively no more than 15 amino acids or alternatively, of these polypeptides or biological equivalents of each thereof. In one aspect, one or more serine residues of these polypeptides are substituted with one or more alanines, and biological equivalents of such, wherein a biological equivalent of comprises a polypeptide that has at least 80% sequence identity to these polypeptides, or wherein a biological equivalent comprises an isolated polypeptide encoded by an an isolated polynucleotide that hybridizes under high stringency conditions to the compliment polynucleotide or the polynucleotide encoding these polypeptides.

In one aspect, the MPS peptide comprises, or consists essentially of, an amino acid sequence selected from:

```
                                              (SEQ ID NO: 2)
KKKRFSFKKSFK.
                                              (SEQ ID NO: 3)
KKKKRFSFKKSFK,
                                              (SEQ ID NO: 4)
KKKR(A/I/L/V/W/Y)S(A/I/L/V/W/Y)KKS(A/I/L/V/W/Y)K;
                                              (SEQ ID NO: 5)
XXXXXRYSYXXSYXLSGYSYXXNXX,
                                              (SEQ ID NO: 6)
(H/R)3RFSF(H/R)2SF(H/R);
                                              (SEQ ID NO: 7)
KKKKKR(A/I/L/V/W/Y)S(A/I/L/V/W/Y)KKS(A/I/L/V/W/Y)
KLSGFSFKKNKK;
                                              (SEQ IN NO: 8)
(H/R)5RFSF(H/R)2SF(H/R)LSGFSF(H/R)2N(H/R)2;
                                              (SEQ ID NO: 9)
KKKKKRFSFKKSFKLSGFSFKKNKK;
                                              (SEQ ID NO: 10)
KKKKKRFAFKKAFKLAGFAFKKNKK;
                                              (SEQ ID NO: 11)
XXXRYAYXXAYX;
                                              (SEQ ID NO: 12)
XXXXXRYAYXXAYXLAGYAYXXNXX;
                                              (SEQ ID NO: 13)
(KKKRFAFKKAFK);
                                              (SEQ ID NO: 21)
XXXRYSYXXSYX;
                                              (SEQ ID NO: 22)
XXXXRYSYXXSYX;
                                              (SEQ ID NO: 23)
XXXXXRYSYXXSYX;
                                              (SEQ ID NO: 24)
XXXXXRYSYXXSYXL;
                                              (SEQ ID NO: 25)
XXXXXRYSYXXSYXLS;
                                              (SEQ ID NO: 26)
XXXXXRYSYXXSYXLSG;
                                              (SEQ ID NO: 27)
XXXXXRYSYXXSYXLSGY;
                                              (SEQ ID NO: 28)
XXXXXRYSYXXSYXLSGYS;
                                              (SEQ ID NO: 29)
XXXXXRYSYXXSYXLSGYSY;
```

```
XXXXXRYSYXXSYXLSGYSYX;                      (SEQ ID NO: 30)

XXXXXRYSYXXSYXLSGYSYXX;                     (SEQ ID NO: 31)

XXXXXRYSYXXSYXLSGYSYXXN;                    (SEQ ID NO: 32)

XXXXXRYSYXXSYXLSGYSYXXNX;                   (SEQ ID NO: 33)
``` and optionally wherein one or more serine (S) is substituted with one or more neutral or positively charged amino acids, that may be the same or different, e.g., one or more serines are substituted with one or more alanines (A);
wherein in one aspect where appropriate, one or more or all serines (S) of the polypeptides are replaced with one or more an alanine amino acid (A); and biological equivalents thereof, wherein a biological equivalent of SEQ ID NOs: 1 to 13 or 21 to 33 (and optionally wherein one or more serine (S) is substituted with one or more neutral or positively charged amino acids, that may be the same or different, e.g., one or more serines are substituted with one or more alanines (A)), comprises a polypeptide that has at least 80% sequence identity to these polypeptides, or wherein a biological equivalent comprises an isolated polypeptide encoded by an isolated polynucleotide that hybridizes under conditions of high stringency to a polynucleotide encoding a polypeptide, respectively or the complement of the polynucleotide encoding the polypeptides, wherein high stringency hybridization conditions is generally performed at about 60° C. in about 1×SSC. A biological equivalent also includes a polypeptide having at least 80% amino acid sequence identity to a polypeptide having an amino acid sequence as described above. The polypeptides and biological equivalents have the ability to: prevent, reduce, delay, inhibit or suppress solid tumor cell growth or metastasis; promote apoptosis; inhibit cancer stem cell growth; inhibit the PIP3 level in the cell; suppress tumor cell mobility; and/or restore sensitivity of a chemoresistant cancer cell to a chemotherapeutic. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, the polypeptide is no more than 45 amino acids, or alternatively 40 amino acids, or alternatively 35 amino acids, or alternatively 30 amino acids, or alternatively no more than 25 amino acids, or alternatively no more than 20 amino acids, or alternatively no more than 15 amino acids or alternatively, the polypeptides of SEQ ID NO: 1 or 11, and optionally wherein one or more serine (S) is substituted with one or more neutral or positively charged amino acids, that may be the same or different, e.g., one or more serines are substituted with one or more alanines (A), or biological equivalents of each thereof. SEQ ID NOs: 10 and 11, as compared to SEQ ID NOs: 2 and 9, are MPS polypeptides wherein the 4 serine residues of wild-type MPS peptide (SEQ ID NO: 9) are replaced by alanine residues, e.g., (KKKKKRFAFK-KAFKLAGFAFKKNKK (SEQ ID NO: 10), that increases membrane affinity. The polypeptides of SEQ ID NO: 9 to 11 are highly positive charged and interact electrostatically with PIP2 on the phospholipid membrane. Similar to SEQ ID NO: 9, the polypepeptides of SEQ ID NOs: 10 and 11 are able to get into cancer cells and reduce phospho-MARCKS levels. The MPS polypeptide of SEQ ID NO: 10 is shown to have greater peptide-cell interaction and better anti-cancer activity, as compared to MPS peptide. In one aspect, the polypeptide "D-Mut MPS polypeptide" (KKKKKRFDFK-KDFKLDGFDFKKNKK)(SEQ ID NO: 14) and those of SEQ ID NOs: 1 to 13 or 21 to 33, having all Ds substited for all serines (S) are specifically excluded from a biological equivalents of MPS polypeptides.

In one aspect, the isolated polypeptide has at least one amino acid that is a modified, non-naturally occurring amino acid such as D-lysine. In a further aspect, further provided is an isolated MPS polypeptide and one or more of: an amino acid sequence to facilitate entry of the isolated polypeptide into the cell; a targeting polypeptide or a polypeptide that confers stability to the polypeptide.

In a further aspect, the polypeptide is no more than 45, or alternatively, 40, or alternatively 35, or alternatively 30 amino acids, or alternatively 25 amino acids, or alternatively 20 amino acids, or alternatively 15 amino acids or alternatively, comprising, or alternatively consisting essentially of, or yet further consisting of the sequence (KK-KRFSFKKSFK) (SEQ ID NO: 2) and optionally wherein one or more serine (S) is substituted with one or more neutral or positively charged amino acids, that may be the same or different, e.g., one or more serines are substituted with one or more alanines (A).

Also provided is an isolated polypeptide comprising no more than 51 amino acids, wherein the amino acid sequence comprises, or alternatively consists essentially of, or alternatively consisting of a polypeptide that targets the polypeptide to a specific cell type or stabilizes the polypeptide or yet further comprises a transduction domain for facilitated cell entry or tumor targeting domain and an MPS polypeptide as described herein.

In one aspect, the polypeptides include substantially homologous and biologically equivalent polypeptides. Substantially homologous and biologically equivalent polypeptides fragments intend those having at least 80% homology, or alternatively at least 85% homology, or alternatively at least 90% homology, or alternatively, at least 95% homology or alternatively, at least 98% homology to those described above, each as determined using methods known to those skilled in the art and identified herein, when run under default parameters.

The polypeptides are useful therapeutically to inhibit or suppress solid tumor growth such as cancer cell invasion, metastasis, migration and viability of cancer cells in vitro or in vivo. They also promote apoptosis and inhibit the growth of cancer stem cells (such as those expressing CD133+), malignant tumors and cancer cells, increase or induce cancer cell death.

Yet further provided is an isolated polypeptide as described above, having additional amino acids added onto the carboxyl-terminal end or amino-terminal end of the MPS and biological equivalents of each thereof, such that the length of the polypeptide comprises an additional at least 10 amino acids, or alternatively at least 15 amino acids, or alternatively at least 20 amino acids, or alternatively at least 25 amino acids, or alternatively at least 30 amino acids, or alternatively at least 35 amino acids or the addition of amino acids up to a total of 51 amino acids.

It is known to those skilled in the art that modifications can be made to any peptide to provide it with altered properties. Peptide fragments of the invention can be modified to include unnatural amino acids. Thus, the peptides may comprise D-amino acids, a combination of D- and L-amino acids, and various "designer" amino acids (e.g., β-methyl amino acids, C-α-methyl amino acids, and N-α-methyl amino acids, etc.) to convey special properties to peptides. Additionally, by assigning specific amino acids at specific coupling steps, peptides with α-helices, β turns, β sheets, α-turns, and cyclic peptides can be generated. Generally, it is believed that α-helical secondary structure or random secondary structure is preferred. The disclosed polypeptides, in one aspect, contain unnatural amino acids.

It is known to those skilled in the art that modifications can be made to any peptide by substituting one or more amino acids with one or more functionally equivalent amino acids that does not alter the biological function of the peptide. In one aspect, the amino acid that is substituted by an amino acid that possesses similar intrinsic properties including, but not limited to, hydrophobic, size, or charge. Methods used to determine the appropriate amino acid to be substituted and for which amino acid are known to one of skill in the art. Non-limiting examples include empirical substitution models as described by Layoff et al. (1978) In Atlas of Protein Sequence and Structure Vol. 5 suppl. 2 (ed. MR. Day off), pp. 345-352. National Biomedical Research Foundation, Washington D.C.; PAM matrices including Day off matrices (Layoff et al. (1978), supra, or JET matrices as described by Jones et al. (1992) Compute. Appl. Basic. 8:275-282 and Gannet et al. (1992) Science 256:1443-1145; the empirical model described by Adak and Hasegawa (1996) J. Mol. Evil. 42:459-468; the block substitution matrices (BLOSSOM) as described by Henrico and Henrico (1992) Proc. Natl. Acad. Sci. USA 89:10915-10919; Poisson models as described by Neil (1987) Molecular Evolutionary Genetics. Columbia University Press, New York.; and the Maximum Likelihood (ML) Method as described by Muller et al. (2002) Mol. Biol. Evil. 19:8-13.

Accordingly, in yet another aspect the isolated peptide fragment may comprise, or alternatively consisting essentially of, or yet further consisting of, a "biologically equivalent" or "biologically active" polypeptide encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical primary amino acid sequence to the reference polypeptide when compared using sequence identity methods run under default conditions.

Polypeptides comprising, or alternatively consisting essentially of, or yet further consisting of, the amino acid sequences of the invention can be prepared by expressing polynucleotides encoding the polypeptide sequences of this invention in an appropriate host cell. This can be accomplished by methods of recombinant DNA technology known to those skilled in the art. Accordingly, this invention also provides methods for recombinantly producing the polypeptides of this invention in a eukaryotic or prokaryotic host cell, which in one aspect is further isolated from the host cell. The proteins and peptide fragments of this invention also can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence.

The protein and peptide fragments may be operatively linked to a transduction domain for facilitated cell entry. Protein transduction offers an alternative to gene therapy for the delivery of therapeutic proteins into target cells, and methods involving protein transduction are within the scope of the invention. Protein transduction is the internalization of proteins into a host cell from the external environment. The internalization process relies on a protein or peptide which is able to penetrate the cell membrane. To confer this ability on a normally non-transducing protein, the non-transducing protein can be fused to a transduction-mediating protein such as the antennapedia peptide, the HIV TAT protein transduction domain, or the herpes simplex virus VP22 protein. See Ford et al. (2001) Gene Ther. 8:1-4. As such the polypeptides of the invention can, for example, include modifications that can increase such attributes as stability, half-life, ability to enter cells and aid in administration, e.g., in vivo administration of the polypeptides of the invention. For example, polypeptides of the invention can comprise, or alternatively consisting essentially of, or yet further consisting of, a protein transduction domain of the HIV TAT protein as described in Schwarze et al. (1999) Science 285:1569-1572. In addition or alternatively, the polypeptides include amino acid sequences that target the polypeptide to the cell or tissue to be treated and/or stabilizes the polypeptide.

In a further aspect, any of the proteins or peptides of this invention can be combined with a detectable label such as a dye for ease of detection. Non-limiting examples of such include radioisotopes, fluorochromes, chemiluminescent compounds, dyes, and proteins, including enzymes.

The polypeptides can be combined with another drug or agent (such as a protein, polypeptide, antibody, antibody fragment that may or may not be an anticancer drug or agent), such as an anticancer drug or agent such as a TKI, a platinum drug or a drug or agent that targets EGFR. In another aspect, the compositions are combined with a MARCKS protein, polypeptide or fragment thereof, wherein the MARCKS fragment comprises a polypeptide fragment that does not overlap in amino acid sequence with a polypeptide of the present disclosure. These compositions can be combined with a carrier, such as a pharmaceutically acceptable carrier for use in the diagnostic, screening and therapeutic methods as disclosed herein.

This invention also provides pharmaceutical composition for in vitro and in vivo use comprising, or alternatively consisting essentially of, or yet further consisting of a therapeutically effective amount of the MPS polypeptide or polynucleotide encoding the MPS polypeptide, that causes at least about 75%, or alternatively at least about 80%, or alternatively at least about 85%, or alternatively at least about 90%, or alternatively at least about 95%, or alternatively at least about 99% effectiveness in the methods provided herein when applied in a molar concentration of less than about 10 micromolar, or alternatively less than about 9 micromolar, or alternatively less than about 8 micromolar, or alternatively less than about 7 micromolar, or alternatively less than about 6 micromolar, or alternatively less than about 5 micromolar, or alternatively less than about 4 micromolar, or alternatively less than about 3 micromolar, or alternatively less than about 2 micromolar, or alternatively less than about 1 micromolar, or alternatively less than about 0.5 micromolar, or alternatively less than about 0.25 micromolar concentration, as compared to a control that does not receive the composition. Comparative effectiveness can be determined by suitable in vitro or in vivo methods as known in the art.

This invention also provides compositions for in vitro and in vivo use comprising, or alternatively consisting essentially of, or yet further consisting of one or more of the isolated polypeptides or polynucleotides described herein and a pharmaceutically acceptable carrier. In one aspect, the compositions are pharmaceutical formulations for use in the therapeutic methods of this invention. In a further aspect, the invention provides a pharmaceutical composition comprising, or alternatively consisting essentially of, or yet further consisting of, the isolated polypeptide or polynucleotide in a concentration such that a therapeutically effective amount of the polypeptide or a pharmacological dose of the composition causes at least a 75%, or alternatively at least a 80%, or alternatively at least a 85%, or alternatively at least a 90%, or alternatively at least a 95% or alternatively at least a 97% reduction in cell growth for example, when applied in a molar concentration of less than 1 micromolar, to a culture of responsive cancer cells as compared to a control that does not receive the composition.

Isolated Polynucleotides and Compositions

This invention also provides isolated polynucleotides encoding the polypeptides described above and an isolated anti-MPS shRNA. Non-limiting examples of the polypeptides of this disclosure include SEQ ID NOs: 1-14 and 21-33, and biological equivalents thereof, as well as polypeptides wherein one or more serine (S) is substituted with one or more neutral or positively charged amino acids, that may be the same or different, e.g., one or more serines are substituted with one or more alanines (A), and biological equivalents thereof. Additional examples of polynucleotides include SEQ ID NOs: 15-20, and biological equivalents thereof. In one aspect the polynucleotides encode MPS biological equivalents. In another aspect, the polynucleotides or their biological equivalents are labeled with a detectable marker or label, such as a dye or radioisotope, for ease of detection. The polynucleotides that encode MPS polypeptide can be inserted into expression vectors and delivered into target cells, e.g., cancer cells, for the diagnostic and t therapeutic methods as disclosed herein.

This invention also provides the complementary polynucleotides to the sequences identified above, their biological equivalents or their complements. Complementarity can be determined using traditional hybridization under conditions of moderate or high stringency. As used herein, the term polynucleotide intends DNA and RNA as well as modified nucleotides. For example, this invention also provides the anti-sense polynucleotide strand, e.g. antisense RNA or siRNA (shRNA) to these sequences or their complements, non-limiting examples of which are provided as SEQ ID NOs: 15-20. One can obtain an antisense RNA using the sequences that encode MPS polypeptide, SEQ ID NOs: 1 to 13 or equivalents of each thereof, using a methodology known to one of ordinary skill in the art wherein the degeneracy of the genetic code provides several polynucleotide sequences that encode the same polypeptide or the methodology described in Van der Krol et al. (1988) BioTechniques 6:958. In another aspect, the polynucleotides or their biological equivalents are labeled with a detectable marker or label, such as a dye or radioisotope, for ease of detection. In one aspect, the polypeptide encoding SEQ ID NO: 14 is excluded from biologically equivalent polypeptides of this disclosure.

Also provided are polynucleotides encoding substantially homologous and biologically equivalent polypeptides or peptide fragments to the inventive peptide fragments. Substantially homologous and biologically equivalent intends those having varying degrees of homology, such as at least 65%, or alternatively, at least 70%, or alternatively, at least 75%, or alternatively at least 80%, or alternatively, at least 85%, or alternatively at least 90%, or alternatively, at least 95%, or alternatively at least 97% homologous as defined above and which encode polypeptides having the biological activity as described herein. It should be understood although not always explicitly stated that embodiments to substantially homologous peptides and polynucleotides are intended for each aspect of this invention, e.g., peptides, polynucleotides and antibodies. In one aspect, the polynucleotide encoding SEQ ID NO: 14 is excluded from biologically equivalent polynucleotides of this disclosure.

Alternatively, a biological equivalent is a polypeptide encoded by a nucleic acid that hybridizes under stringent conditions to a nucleic acid or complement that encodes the polypeptide or when a polynucleotide, a polynucleotide that hybridizes to the reference polynucleotide or its complement under conditions of high stringency. Biologically equivalent polynucleotides hybridize under conditions of high stringency to a polynucleotide encoding the polypeptide of this disclosure or its biological equivalent, or the complement of each. Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell. An equivalent polynucleotide is one that hybridizes under stringent conditions to the reference polynucleotide or the complement of the reference polynucleotide, an in one aspect, having similar biological activity as the reference polynucleotide.

The polynucleotides of this invention can be replicated using conventional recombinant techniques. Alternatively, the polynucleotides can be replicated using PCR technology. PCR is the subject matter of U.S. Pat. Nos. 4,683,195; 4,800,159; 4,754,065; and 4,683,202 and described in PCR: The Polymerase Chain Reaction (Mullis et al. eds, Birkhauser Press, Boston (1994)) and references cited therein. Yet further, one of skill in the art can use the sequences provided herein and a commercial DNA synthesizer to replicate the DNA. Accordingly, this invention also provides a process for obtaining the peptide fragments of this invention by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can operatively link the polynucleotides to regulatory sequences for their expression in a host cell. The polynucleotides and regulatory sequences are inserted into the host cell (prokaryotic or eukaryotic) for replication and amplification. The DNA so amplified can be isolated from the cell by methods well known to those of skill in the art. A process for obtaining polynucleotides by this method is further provided herein as well as the polynucleotides so obtained.

In one aspect, the polynucleotide is an RNA molecule that is short interfering RNA, also known as siRNA, e.g., SEQ ID NOs: 15-20 and biological equivalents thereof. Methods to prepare and screen interfering RNA and select for the ability to block polynucleotide expression are known in the art and non-limiting examples of which are shown below. These interfering RNA are provided by this invention alone or in combination with a suitable vector or within a host cell. Compositions containing the RNAi are further provided. RNAi is useful to knock-out or knock-down select functions in a cell or tissue as known in the art and described herein.

siRNA sequences can be designed by obtaining the target mRNA sequence and determining an appropriate siRNA complementary sequence. siRNAs of the invention are designed to interact with a target sequence, meaning they complement a target sequence sufficiently to hybridize to that sequence. An siRNA can be 100% identical to the target sequence. However, homology of the siRNA sequence to the target sequence can be less than 100% as long as the siRNA can hybridize to the target sequence. Thus, for example, the siRNA molecule can be at least 70%, 75%, 80%, 85%, 90%, 95%, 96%, 97%, 98%, 99% or 100% identical to the target sequence or the complement of the target sequence. Therefore, siRNA molecules with insertions, deletions or single point mutations relative to a target may also be used. The generation of several different siRNA sequences per target mRNA is recommended to allow screening for the optimal target sequence. A homology search, such as a BLAST search, should be performed to ensure that the siRNA sequence does not contain homology to any known mammalian gene.

In general, it is preferable that the target sequence be located at least 100-200 nucleotides from the AUG initiation codon and at least 50-100 nucleotides away from the termination codon of the target mRNA (Duxbury (2004) J. Surgical Res. 117:339-344).

Researchers have determined that certain characteristics are common in siRNA molecules that effectively silence their target gene (Duxbury (2004) J. Surgical Res. 117:339-344; Ui-Tei et al. (2004) Nucl. Acids Res. 32:936-48). As a general guide, siRNAs that include one or more of the following conditions are particularly useful in gene silencing in mammalian cells: GC ratio of between 45-55%, no runs of more than 9 G/C residues, G/C at the 5' end of the sense strand; A/U at the 5' end of the antisense strand; and at least 5 A/U residues in the first 7 bases of the 5' terminal of the antisense strand.

siRNA are, in general, from about 10 to about 30 nucleotides in length. For example, the siRNA can be 10-30 nucleotides long, 12-28 nucleotides long, 15-25 nucleotides long, 19-23 nucleotides long, or 21-23 nucleotides long. When an siRNA contains two strands of different lengths, the longer of the strands designates the length of the siRNA. In this situation, the unpaired nucleotides of the longer strand would form an overhang.

The term siRNA includes short hairpin RNAs (shRNAs). shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides long. For example, the stem can be 10-30 nucleotides long, 12-28 nucleotides long, 15-25 nucleotides long, 19-23 nucleotides long, or 21-23 nucleotides long.

Tools to assist siRNA design are readily available to the public. For example, a computer-based siRNA design tool is available on the internet at www.dharmacon.com, last accessed on Nov. 26, 2007.

This invention also provides compositions for in vitro and in vivo use comprising, or alternatively consisting essentially of, or yet further consisting of one or more of the isolated polynucleotide as described herein and a pharmaceutically acceptable carrier. In one aspect, the compositions are pharmaceutical formulations for use in the therapeutic methods of this invention. In a further aspect, the invention provides a pharmaceutical composition comprising, or alternatively consisting essentially of, or yet further consisting of, the isolated polynucleotide in a concentration such that a therapeutically effective amount of the or pharmacological dose of the composition causes at least a 75%, or alternatively at least a 80%, or alternatively at least a 85%, or alternatively at least a 90%, or alternatively at least a 95% or alternatively at least a 97% reduction in cancer cell growth, viability or migration, as compared to a control that does not receive the composition. Comparative effectiveness can be determined by suitable in vitro or in vivo methods as known in the art and described herein.

Synthesis of dsRNA and siRNA dsRNA and siRNA can be synthesized chemically or enzymatically in vitro as described in Micura (2002) Agnes Chem. Int. Ed. Emgl. 41:2265-2269; Betz (2003) Promega Notes 85:15-18; and Paddison and Hannon (2002) Cancer Cell. 2:17-23. Chemical synthesis can be performed via manual or automated methods, both of which are well known in the art as described in Micura (2002), supra. siRNA can also be endogenously expressed inside the cells in the form of shRNAs as described in Yu et al. (2002) Proc. Natl. Acad. Sci. USA 99:6047-6052; and McManus et al. (2002) RNA 8:842-850. Endogenous expression has been achieved using plasmid-based expression systems using small nuclear RNA promoters, such as RNA polymerase III U6 or H1, or RNA polymerase II U1 as described in Brummelkamp et al. (2002) Science 296:550-553 (2002); and Novarino et al. (2004) J. Neurosci. 24:5322-5330.

In vitro enzymatic dsRNA and siRNA synthesis can be performed using an RNA polymerase mediated process to produce individual sense and antisense strands that are annealed in vitro prior to delivery into the cells of choice as described in Fire et al. (1998) Nature 391:806-811; Donze and Picard (2002) Nucl. Acids Res. 30(10):e46; Yu et al. (2002); and Shim et al. (2002) J. Biol. Chem. 277:30413-30416. Several manufacturers (Promega, Ambion, New England Biolabs, and Stragene) produce transcription kits useful in performing the in vitro synthesis.

In vitro synthesis of siRNA can be achieved, for example, by using a pair of short, duplex oligonucleotides that contain T7 RNA polymerase promoters upstream of the sense and antisense RNA sequences as the DNA template. Each oligonucleotide of the duplex is a separate template for the synthesis of one strand of the siRNA. The separate short RNA strands that are synthesized are then annealed to form siRNA as described in Protocols and Applications, Chapter 2: RNA interference, Promega Corporation, (2005).

In vitro synthesis of dsRNA can be achieved, for example, by using a T7 RNA polymerase promoter at the 5'-ends of both DNA target sequence strands. This is accomplished by using separate DNA templates, each containing the target sequence in a different orientation relative to the T7 promoter, transcribed in two separate reactions. The resulting transcripts are mixed and annealed post-transcriptionally. DNA templates used in this reaction can be created by PCR or by using two linearized plasmid templates, each containing the T7 polymerase promoter at a different end of the target sequence. Protocols and Applications, Chapter 2: RNA interference, Promega Corporation (2005).

RNA can be obtained by first inserting a DNA polynucleotide into a suitable prokaryotic or eukaryotic host cell. The DNA can be inserted by any appropriate method, e.g., by the use of an appropriate gene delivery vehicle (e.g., liposome, plasmid or vector) or by electroporation. When the cell replicates and the DNA is transcribed into RNA; the RNA can then be isolated using methods well known to those of skill in the art, for example, as set forth in Sambrook and Russell (2001) supra. For instance, mRNA can be isolated using various lytic enzymes or chemical solutions according to the procedures set forth in Sambrook and Russell (2001) supra or extracted by nucleic-acid-binding resins following the accompanying instructions provided by manufactures.

In order to express the proteins described herein, delivery of nucleic acid sequences encoding the gene of interest can be delivered by several techniques. Examples of which include viral technologies (e.g. retroviral vectors, adenovirus vectors, adeno-associated virus vectors, alphavirus vectors and the like) and non-viral technologies (e.g. DNA/liposome complexes, micelles and targeted viral protein-DNA complexes) as described herein. Once inside the cell of interest, expression of the transgene can be under the control of ubiquitous promoters (e.g. EF-1) or tissue specific promoters (e.g. Calcium Calmodulin kinase 2 (CaMKI) promoter, NSE promoter and human Thy-1 promoter). Alternatively expression levels may controlled by use of an inducible promoter system (e.g. Tet on/off promoter) as described in Wiznerowicz et al. (2005) Stem Cells 77:8957-8961.

Non-limiting examples of promoters include, but are not limited to, the cytomegalovirus (CMV) promoter (Kaplitt et al. (1994) Nat. Genet. 8:148-154), CMV/human ÿ-globin promoter (Mandel et al. (1998) J. Neurosci. 18:4271-4284), NCX1 promoter, ÿMHC promoter, MLC2v promoter, GFAP promoter (Xu et al. (2001) Gene Ther. 8:1323-1332), the 1.8-kb neuron-specific enolase (NSE) promoter (Klein et al. (1998) Exp. Neurol. 150:183-194), chicken beta actin (CBA) promoter (Miyazaki (1989) Gene 79:269-277) and the β-glucuronidase (GUSB) promoter (Shipley et al. (1991) Genetics 10:1009-1018), the human serum albumin promoter, the alpha-1-antitrypsin promoter. To improve expression, other regulatory elements may additionally be operably linked to the transgene, such as, e.g., the Woodchuck Hepatitis Virus Post-Regulatory Element (WPRE) (Donello et al. (1998) J. Virol. 72: 5085-5092) or the bovine growth hormone (BGH) polyadenylation site.

The invention further provides the isolated polynucleotides of this invention operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are well known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)), which contains maps, functional properties, commercial suppliers and a reference to GenEMBL accession numbers for various suitable vectors. Preferable, these vectors are capable of transcribing RNA in vitro or in vivo.

Expression vectors containing these nucleic acids are useful to obtain host vector systems to produce proteins and polypeptides. It is implied that these expression vectors must be replicable in the host organisms either as episomes or as an integral part of the chromosomal DNA. Suitable expression vectors include plasmids, viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells as described above and constructed using well known methods. See Sambrook and Russell (2001), supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; DEAE-dextran; electroporation; or microinjection. See Sambrook and Russell (2001), supra for this methodology.

The present invention also provides delivery vehicles suitable for delivery of a polynucleotide of the invention into cells (whether in vivo, ex vivo, or in vitro). A polynucleotide of the invention can be contained within a gene delivery vehicle, a cloning vector or an expression vector. These vectors (especially expression vectors) can in turn be manipulated to assume any of a number of forms which may, for example, facilitate delivery to and/or entry into a cell.

In one aspect when polynucleotides encoding two or more peptides, at least one of which is an MPS, SEQ ID NO: 1-14 or 21 to 33, or a biological equivalent of each thereof, are intended to be translated and optionally expressed, the polynucleotides encoding the polypeptides may be organized within a recombinant mRNA or cDNA molecule that results in the transcript that expresses on a single mRNA molecule the at least two peptides. This is accomplished by use of a polynucleotide that has the biological activity of an internal ribosome entry site (IRES) located between the polynucleotide encoding the two peptides. IRES elements initiate translation of polynucleotides without the use of a "cap" structure traditionally thought to be necessary for translation of proteins in eukaryotic cells. Initially described in connection with the untranslated regions of individual picornaviruses, e.g. polio virus and encephalomyocarditis virus, IRES elements were later shown to efficiently initiate translation of reading frames in eukaryotic cells and when positioned downstream from a eukaryotic promoter, it will not influence the "cap"-dependent translation of the first cistron. The IRES element typically is at least 450 nucleotides long when in occurs in viruses and possesses, at its 3' end, a conserved "UUUC" sequence followed by a polypyrimidine trace, a G-poor spacer and an AUG triple.

As used herein, the term "IRES" is intended to include any molecule such as a mRNA polynucleotide or its reverse transcript (cDNA) which is able to initiate translation of the gene downstream from the polynucleotide without the benefit of a cap site in a eukaryotic cell. "IRES" elements can be identical to sequences found in nature, such as the picornavirus IRES, or they can be non-naturally or non-native sequences that perform the same function when transfected into a suitable host cell. Bi- and poly-cistronic expression vectors containing naturally occurring IRES elements are known in the art and described for example, in Pestova et al. (1998) Genes Dev. 12:67-83 and International PCT Publication No. WO 01/04306, which in turn on page 17, lines 35 to 38 references several literature references which include, but are not limited to Ramesh et al. (1996) Nucl. Acids Res. 24:2697-2700; Pelletier et al. (1988) Nature 334:320-325; Jan et al. (1989) J. Virol. 63:1651-1660; and Davies et al. (1992) J. Virol. 66:1924-1932. Paragraph [0009] of U.S. Patent Application Publication No. 2005/0014150 A1 discloses several issued U.S. patents wherein a virally-derived IRES element was used to express foreign gene(s) in linear multi-cistronic mRNAs in mammalian cells, plant cells and generally in eukaryotic cells. U.S. Patent Application Publication No. 2004/0082034 A1 discloses an IRES element active in insect cells. Methods to identify new elements also are described in U.S. Pat. No. 6,833,254.

Also within the term "IRES" element are cellular sequences similar to that disclosed in U.S. Pat. No. 6,653,132. The patent discloses a sequence element (designated SP163) composed of sequences derived from the 5'-UTR of VEGF (Vascular Endothelial Growth Factor gene), which, was presumably generated through a previously unknown mode of alternative splicing. The patentees report that an advantages of SP163 is that it is a natural cellular IRES element with a superior performance as a translation stimulator and as a mediator of cap-independent translation relative to known cellular IRES elements and that these functions are maintained under stress conditions.

Further within the term "IRES" element are artificial sequences that function as IRES elements that are described, for example, in U.S. Patent Application Publication No. 2005/0059004 A1.

Operatively linked to the IRES element and separately, are sequences necessary for the translation and proper processing of the peptides. Examples of such include, but are not limited to a eukaryotic promoter, an enhancer, a termination sequence and a polyadenylation sequence. Construction and use of such sequences are known in the art and are combined with IRES elements and protein sequences using recombinant methods. "Operatively linked" shall mean the juxtaposition of two or more components in a manner that allows them to junction for their intended purpose. Promoters are sequences which drive transcription of the marker or target protein. It must be selected for use in the particular host cell, i.e., mammalian, insect or plant. Viral or mammalian promoters will function in mammalian cells. The promoters can be constitutive or inducible, examples of which are known and described in the art.

In one aspect, the peptides are transcribed and translated from a separate recombinant polynucleotide and combined into a functional protein in the host cell. This recombinant polynucleotide does not require the IRES element or marker protein although in one aspect, it may be present.

These isolated host cells containing the polynucleotides of this invention are useful in the methods described herein as well as for the recombinant replication of the polynucleotides and for the recombinant production of peptides and for high throughput screening.

Host Cells

Also provided are host cells comprising one or more of the polypeptides, and/or polynucleotides of this invention. Suitable cells containing the inventive polypeptides and/or polynucleotides include prokaryotic and eukaryotic cells, which include, but are not limited to bacterial cells, yeast cells, insect cells, animal cells, mammalian cells, murine cells, rat cells, sheep cells, simian cells and human cells. Examples of bacterial cells include *Escerichia coli, Salmonella enterica* and *Streptococcus gordonii*. The cells can be purchased from a commercial vendor such as the American Type Culture Collection (ATCC, Rockville Md., USA) or cultured from an isolate using methods known in the art. Examples of suitable eukaryotic cells include, but are not limited to 293T HEK cells, as well as the hamster cell line BHK-21; the murine cell lines designated NIH3T3, NS0, C127, the simian cell lines COS, Vero; and the human cell lines HeLa, PER.C6 (commercially available from Crucell) U-937 and Hep G2. A non-limiting example of insect cells include *Spodoptera frugiperda*. Examples of yeast useful for expression include, but are not limited to *Saccharomyces, Schizosaccharomyces, Hansenula, Candida, Torulopsis, Yarrowia*, or *Pichia*. See e.g., U.S. Pat. Nos. 4,812,405; 4,818,700; 4,929,555; 5,736,383; 5,955,349; 5,888,768 and 6,258,559.

In addition to species specificity, the cells can be of any particular tissue type such as a somatic or embryonic stem cell such as a stem cell that can or cannot differentiate into a terminally differentiated cell. The stem cell can be of human or animal origin, such as mammalian.

Therapeutic Antibody Compositions

This invention also provides an antibody capable of specifically forming a complex with a polypeptide of this invention, which are useful in the therapeutic methods of this invention. In one aspect, the antibody or fragment thereof specifically binds to a phosphoryation site domain (PSD) of MARCKS protein, which can prevent MARCKS from phosphoryation and/or sequester the proteins that naturally interact with MARCKS. In another aspect, the antibody or fragment thereof is conjugated to a peptide or other molecule to facilitate entry into the cell. The term "antibody" is described above and includes polyclonal antibodies and monoclonal antibodies, antibody fragments, as well as derivatives thereof. The antibodies include, but are not limited to cows, rabbits, goats, mice, rats, hamsters, guinea pigs, sheep, dogs, cats, monkeys, chimpanzees, apes, etc. The antibodies are also useful to identify and purify therapeutic and/or diagnostic polypeptides. Also provided are hybridoma cell lines producing monoclonal antibodies of this invention.

Polyclonal antibodies of the invention can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, which induces the B-lymphocytes to produce IgG immunoglobulins specific for the antigen. This IgG is purified from the mammal's serum. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a slow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods described in U.S. Pat. Nos. 7,279,559; 7,119,179; 7,060,800; 6,709,659; 6,656,746; 6,322,788; 5,686,073; and 5,670,153.

The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, e.g., www.atcc.org, www.lifetech.com., last accessed on Nov. 26, 2007, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

In one embodiment, the antibodies described herein can be generated using a Multiple Antigenic Peptide (MAP) system. The MAP system utilizes a peptidyl core of three or seven radially branched lysine residues, on to which the antigen peptides of interest can be built using standard solid-phase chemistry. The lysine core yields the MAP bearing about 4 to 8 copies of the peptide epitope depending on the inner core that generally accounts for less than 10% of total molecular weight. The MAP system does not require a carrier protein for conjugation. The high molar ratio and dense packing of multiple copies of the antigenic epitope in a MAP has been shown to produce strong immunogenic response. This method is described in U.S. Pat. No. 5,229,490.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsried/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134.

Antibody derivatives of the present invention can also be prepared by delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

Antibody derivatives also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured there from. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to known methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies of the present invention can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See, e.g., Russel et al. (2000) Infection and Immunity April 2000: 1820-1826; Gallo et al. (2000) European J. of Immun. 30:534-540; Green (1999) J. of Immun. Methods 231:11-23; Yang et al. (1999) J. of Leukocyte Biology 66:401-410; Yang (1999) Cancer Research 59(6):1236-1243; Jakobovits (1998) Advanced Drug Delivery Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; and U.S. Pat. No. 6,075,181.)

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies of this invention can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological Interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al., (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen.)

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Fd segments ($V_H$-$C_H$1-VH-$C_H$1) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic cells as described above.

If a monoclonal antibody being tested binds with protein or polypeptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding the protein or polypeptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with a protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307.

The isolation of other hybridomas secreting monoclonal antibodies with the specificity of the monoclonal antibodies of the invention can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody produced by the hybridoma of interest.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

Antibodies can be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I), yttrium-90 ($^{90}$Y), bismuth-212 ($^{212}$Bi), (bismuth-213 ($^{213}$Bi), technetium-99m ($^{99m}$Tc), rhenium-186 ($^{186}$Re), and rhenium-188 ($^{188}$Re); antibiotics, such as doxorubicin, adriamycin, daunorubicin, methotrexate, daunomycin, neo-carzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from Chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies of the invention also can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

Compositions for Therapy

One or more of the above antibody, antibody fragment, antibody derivative, polypeptide or polynucleotides encoding these compositions and siRNA can be further combined with another therapeutic such as an anticancer drug, e.g., a TKI, a platinum drug, a drug or agent that targets EGFR, or a MANS polypeptide or fragment thereof, wherein the fragment comprises a polypeptide and a carrier, a pharmaceutically acceptable carrier or medical device which is suitable for use of the compositions in diagnostic or therapeutic methods. Thus, the compositions comprise, or alternatively consist essentially of, or yet further consists of, one or more of the above compositions described above in combination with a carrier, a pharmaceutically acceptable carrier or medical device.

The carrier can be a liquid phase carrier or a solid phase carrier, e.g., bead, gel, microarray, or carrier molecule such as a liposome. The composition can optionally further comprise at least one further compound, protein or composition.

Additional examples of "carriers" includes therapeutically active agents such as another peptide or protein (e.g., an Fab' fragment). For example, an antibody of this invention, derivative or fragment thereof can be functionally linked (e.g., by chemical coupling, genetic fusion, noncovalent association or otherwise) to one or more other molecular entities, such as another antibody (e.g., to produce a bispecific or a multispecific antibody), a cytotoxin, a cellular ligand or an antigen. Accordingly, this invention encompasses a large variety of antibody conjugates, bi- and multispecific molecules, and fusion proteins, whether or not they target the same epitope as the antibodies of this invention.

Yet additional examples of carriers are organic molecules (also termed modifying agents) or activating agents, that can be covalently attached, directly or indirectly, to an antibody of this invention. Attachment of the molecule can improve pharmacokinetic properties (e.g., increased in vivo serum half-life). Examples of organic molecules include, but are not limited to a hydrophilic polymeric group, a fatty acid group or a fatty acid ester group. As used herein, the term "fatty acid" encompasses mono-carboxylic acids and dicarboxylic acids. A "hydrophilic polymeric group," as the term is used herein, refers to an organic polymer that is more soluble in water than in octane.

Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. A suitable hydrophilic polymer that modifies the antibody of the invention has a molecular weight of about 800 to about 150,000 Daltons as a separate molecular entity. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Examples of such include, but are not limited to n-dodecanoate, n-tetradecanoate, n-octadecanoate, n-eicosanoate, n-docosanoate, n-triacontanoate, n-tetracontanoate, cis-Δ9-octadecanoate, all cis-Δ5,8,11, 14-eicosatetraenoate, octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The present invention provides a composition comprising, or alternatively consisting essentially of, or yet further consisting of, at least one antibody of this invention, derivative or fragment thereof, suitable for administration in an effective amount to prevent, reduce, delay, inhibit or suppress solid tumor growth or metastasis (e.g., lung cancer cell, colon cancer, breast cancer, or pancreatic cancer for example), promote apoptosis or inhibit cancer stem cell growth. The compositions include, for example, pharmaceutical and diagnostic compositions/kits, comprising a pharmaceutically acceptable carrier and at least one antibody of this invention, variant, derivative or fragment thereof. As noted above, the composition can further comprise additional antibodies or therapeutic agents which in combination, provide multiple therapies tailored to provide the maximum therapeutic benefit.

Alternatively, a composition of this invention can be co-administered with other therapeutic agents, whether or not linked to them or administered in the same dosing. They can be co-administered simultaneously with such agents (e.g., in a single composition or separately) or can be administered before or after administration of such agents.

Compositions for Diagnosis and Therapy

One or more of the above compositions can be further combined with a carrier, a pharmaceutically acceptable carrier or medical device which is suitable for use of the compositions in diagnostic or therapeutic methods.

The carrier can be a liquid phase carrier or a solid phase carrier, e.g., bead, gel, gene chip, microarray, or carrier molecule such as a liposome. The composition can optionally further comprise at least one further compound, protein or composition, anticancer agent or other small molecule, protein, polypeptide, antibody or antibody fragment, eg., a TKI inhibitor, a drug or agent that targets EGFR, a platinum drug or a MARCKS polypeptide or fragment thereof.

Additional examples of "carriers" includes therapeutically active agents such as another peptide or protein (e.g., an Fab' fragment). For example, an antibody, derivative or fragment thereof can be functionally linked (e.g., by chemical coupling, genetic fusion, noncovalent association or otherwise) to one or more other molecular entities, such as another antibody (e.g., to produce a bispecific or a multispecific antibody), a cytotoxin, a cellular ligand or an antigen. Additionally, the antibodies or fragments thereof can be linked to the polypeptides of this invention to facilitate targeting to a cell or tissue of choice and/or to stabilize the polypeptide. Accordingly, this invention encompasses a large variety of antibody conjugates, bi- and multispecific molecules, and fusion proteins, whether or not they target the same epitope as the antibodies of this invention.

Yet additional examples of carriers are organic molecules (also termed modifying agents) or activating agents, that can be covalently attached, directly or indirectly, to an antibody of this invention. Attachment of the molecule can improve pharmacokinetic properties (e.g., increased in vivo serum half-life). Examples of organic molecules include, but are not limited to a hydrophilic polymeric group, a fatty acid group or a fatty acid ester group. As used herein, the term "fatty acid" encompasses mono-carboxylic acids and dicarboxylic acids. A "hydrophilic polymeric group," as the term is used herein, refers to an organic polymer that is more soluble in water than in octane.

Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. A suitable hydrophilic polymer that modifies the antibody of the invention has a molecular weight of about 800 to about 150,000 Daltons as a separate molecular entity. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Examples of such include, but are not limited to n-dodecanoate, n-tetradecanoate, n-octadecanoate, n-eicosanoate, n-docosanoate, n-triacontanoate, n-tetracontanoate, cis-Δ9-octadecanoate, all cis-Δ5,8,11, 14-eicosatetraenoate, octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

Also provided is a composition containing at least one antibody of this invention. The compositions include, for example, pharmaceutical and diagnostic compositions/kits, comprising a pharmaceutically acceptable carrier and at least one antibody of this invention, variant, derivative or fragment thereof. As noted above, the composition can further comprise additional antibodies or therapeutic agents which in combination, provide multiple therapies tailored to provide the maximum therapeutic benefit.

Alternatively, a composition of this invention can be co-administered with other therapeutic agents, whether or not linked to them or administered in the same dosing. They can be co-administered simultaneously with such agents (e.g., in a single composition or separately) or can be administered before or after administration of such agents. Such agents can include anticancer therapies such as erlotinib, irinotecan, 5-Fluorouracil, Erbitux, Cetuximab, FOLFOX, or radiation therapy or other agents known to those skilled in the art.

Diagnostic Methods Utilizing Recombinant DNA Technology and Bioinformatics

The polynucleotides of this invention can be attached to a solid support such as an array or high density chip for use in high throughput screening assays using methods known in the art. For example, a polynucleotide encoding MPS, e.g. SEQ ID NOs: 1-14 or 21-33, or a biological equivalent of each thereof can be used as a probe to identify expression in a subject sample. The chips can be synthesized on a derivatized glass surface using the methods disclosed in U.S. Pat. Nos. 5,405,783; 5,412,087 and 5,445,934. Photoprotected nucleoside phosphoramidites can be coupled to the glass surface, selectively deprotected by photolysis through a photolithographic mask, and reacted with a second protected nucleoside phosphoramidite. The coupling/deprotection process is repeated until the desired probe is complete.

One can use chemical synthesis to provide the isolated polynucleotides of the present invention. Chemical synthesis of polynucleotides can be accomplished using a number of protocols, including the use of solid support chemistry, where an oligonucleotide is synthesized one nucleoside at a time while anchored to an inorganic polymer. The first nucleotide is attached to an inorganic polymer using a reactive group on the polymer which reacts with a reactive group on the nucleoside to form a covalent linkage. Each subsequent nucleoside is then added to the first nucleoside molecule by: 1) formation of a phosphite linkage between the original nucleoside and a new nucleoside with a protecting group; 2) conversion of the phosphite linkage to a phosphate linkage by oxidation; and 3) removal of one of the protecting groups to form a new reactive site for the next nucleoside as described in U.S. Pat. Nos. 4,458,066; 5,153,319; 5,132,418; and 4,973,679, all of which are incorporated by reference herein. Solid phase synthesis of oligonucleotides eliminates the need to isolate and purify the intermediate products after the addition of every nucleotide base. Following the synthesis of RNA, the oligonucleotides is deprotected (U.S. Pat. No. 5,831,071) and purified to remove by-products, incomplete synthesis products, and the like.

U.S. Pat. No. 5,686,599, describes a method for one pot deprotection of RNA under conditions suitable for the removal of the protecting group from the 2' hydroxyl position. U.S. Pat. No. 5,804,683, describes a method for the removal of exocyclic protecting groups using alkylamines. U.S. Pat. No. 5,831,071, describes a method for the deprotection of RNA using ethylamine, propylamine, or butylamine. U.S. Pat. No. 5,281,701, describes methods and reagents for the synthesis of RNA using 5'-O-protected-2'-O-alkylsilyl-adenosine phosphoramidite and 5'-O-protected-2'-O-alkylsilylguanosine phosphoramidite monomers which are deprotected using ethylthiotetrazole. Usman and Cedergren (1992) Trends in Biochem. Sci. 17:334-339 describe the synthesis of RNA-DNA chimeras for use in studies of the role of 2' hydroxyl groups. Sproat et al. (1995) Nucleosides & Nucleotides 14:255-273, describe the use of 5-ethylthio-1H-tetrazole as an activator to enhance the quality of oligonucleotide synthesis and product yield. Gait et al. (1991) Oligonucleotides and Analogues, ed. F. Eckstein, Oxford University Press 25-48, describe general methods for the synthesis of RNA. U.S. Pat. Nos. 4,923,901; 5,723,599; 5,674,856; 5,141,813; 5,419,966; 4,458,066; 5,252,723; Weetall et al. (1974) Methods in Enzymology 34:59-72; Van Aerschot et al. (1988) Nucleosides and Nucleotides 7:75-90; Maskos and Southern (1992) Nucleic Acids Research 20: 1679-1684; Van Ness et al. (1991) Nucleic Acids Research 19:3345-3350; Katzhendler et al. (1989) Tetrahedron 45:2777-2792; Hovinen et al. (1994) Tetrahedron 50:7203-7218; GB 2,169,605; EP 325,970; International PCT Publication No. WO 94/01446; German Patent No. 280,968; and BaGerman U.S. Pat. No. 4,306,839, all describe specific examples of solid supports for oligonucleotide synthesis and specific methods of use for certain oligonucleotides. Additionally, methods and reagents for oligonucleotide synthesis as known to one of skill in the art as describe by U.S. Pat. No. 7,205,399, incorporated herein by reference in its entirety.

The probes and high density oligonucleotide probe arrays also provide an effective means of monitoring expression of a multiplicity of genes, one of which includes the gene. Thus, the expression monitoring methods can be used in a wide variety of circumstances including detection of disease, identification of differential gene expression between samples isolated from the same patient over a time course, or screening for compositions that upregulate or downregulate the expression of the gene at one time, or alternatively, over a period of time.

Detectable labels suitable for use in the present invention include those identified above as well as any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., $^{3}H$, $^{125}I$, $^{35}S$, $^{14}C$, or $^{32}P$) enzymes (e.g., horseradish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are known to those of skill in the art. Thus, for example, radiolabels may be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

International PCT Publication No. WO 97/10365 describes methods for adding the label to the target (sample) nucleic acid(s) prior to or alternatively, after the hybridization. These are detectable labels that are directly attached to or incorporated into the target (sample) nucleic acid prior to hybridization. In contrast, "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids, see Laboratory Techniques In Biochemistry And Molecular Biology, Vol. 24: Hybridization with Nucleic Acid Probes, P. Tijssen, ed. Elsevier, N.Y. (1993).

The nucleic acid sample also may be modified prior to hybridization to the high density probe array in order to reduce sample complexity thereby decreasing background signal and improving sensitivity of the measurement using the methods disclosed in International PCT Publication No. WO 97/10365.

Results from the chip assay are typically analyzed using a computer software program. See, for example, EP 0717 113 A2 and WO 95/20681. This information is compared against existing data sets of gene expression levels for diseased and healthy individuals. A correlation between the obtained data and that of a set of diseased individuals indicates the onset of a disease in the subject patient.

Methods to Identify Therapeutic Agents

The present invention also provides methods to identify leads and methods for treating cancer. In one aspect, the screen identifies lead compounds or biologics agents that mimic the polypeptides identified above and which are useful to treat these disorders or to treat or ameliorate the symptoms associated with the disorders. Test substances for screening can come from any source. They can be libraries of natural products, combinatorial chemical libraries, biological products made by recombinant libraries, etc. The source of the test substances is not critical to the invention. The present invention provides means for screening compounds and compositions which may previously have been overlooked in other screening schemes.

To practice the screen or assay in vitro, suitable cell cultures or tissue cultures are first provided. The cell can be a cultured cell or a genetically modified cell which differentially expresses the receptor and/or receptor complex. Alternatively, the cells can be from a tissue culture as described below. The cells are cultured under conditions (temperature, growth or culture medium and gas ($CO_2$)) and for an appropriate amount of time to attain exponential proliferation without density dependent constraints. It also is desirable to maintain an additional separate cell culture; one which does not receive the agent being tested as a control.

As is apparent to one of skill in the art, suitable cells may be cultured in microtiter plates and several agents may be assayed at the same time by noting genotypic changes, phenotypic changes and/or cell death.

When the agent is a composition other than a DNA or RNA nucleic acid molecule, the suitable conditions may be by directly added to the cell culture or added to culture medium for addition. As is apparent to those skilled in the art, an "effective" amount must be added which can be empirically determined.

The screen involves contacting the agent with a test cell expressing the complex and then assaying the cell its ability to provide a biological response similar to the polypeptides of this invention. In yet another aspect, the test cell or tissue sample is isolated from the subject to be treated and one or more potential agents are screened to determine the optimal therapeutic and/or course of treatment for that individual patient.

For the purposes of this invention, an "agent" is intended to include, but not be limited to a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies. They can be administered concurrently or sequentially.

Methods of Use of Polypeptides and Their Compositions

Applicants have discovered that the polypeptides of this invention: prevent, reduce, delay, inhibit or suppress solid tumor cell growth or metastasis; promote apoptosis; inhibit cancer stem cell growth (CD133+ cancer stem cell); inhibit the level of PIP3 in the cell; restore sensitivity of a resistant cancer cell to a chemotherapeutic; or suppress tumor cell mobility and/or viability. In one aspect, the cancer is a solid tumor, such as lung cancer (NSCLC), colon cancer, breast cancer, or pancreatic cancer. Thus, methods to achieve such in vitro or in vivo are provided by contacting or administering an effective amount of the polypeptide or other therapeutic composition of this invention (e.g., antibody or siRNA) to a subject in need of such treatment. Administration can be by any suitable method and effective amounts can be empirically determined by a treating physician or one of skill in the art when the contacting is in vitro. In a further aspect, an effective amount of an agent or drug (chemotherapeutic or other) can be combined and contacted or administered as appropriate. In one aspect the chemotherapeutic is a TKI, or an platinum drug, or an agent that targets EGFR or yet further a MARCKS polypeptide or fragment thereof, wherein the fragment is not a N-terminal fragment of MARCKS or a polypeptide that does not have an amino acid sequence having sequence identity to a polypeptide as described above.

Also provided is a method for restoring sensitivity of a chemoresistant cancer cell to a chemotherapeutic drug, the method comprising or alternatively consisting essentially of, or yet further consists of, contacting the cell or administering to a subject in need thereof, an effective amount of an isolated MPS polypeptide or a biological equivalent thereof or an anti-MARCKS siRNA, and optionally, wherein the chemotherapeutic drug or agent is selected from a TKI, a platinum drug, a drug or agent that targets EGFR, cisplatin, paclitaxel, erlotinib or dasatinib; and optionally wherein the chemoresistant cancer cell is a TKI resistant cell. The contacting is in vitro or in vivo and in one aspect, the cell is a mammalian solid tumor cell. In one aspect, the tumor cell comprises or expresses higher levels of phosphorylated MARCKS polypeptide as compared to a normal counterpart cell. Non-limiting examples of such cells include a lung cancer cell, a colon cancer cell, a breast cancer cell or a pancreatic cancer and alternatively or in addition, the patient suffering from advanced cancer (Stage II to IV). In a further aspect, the method further comprises contacting the cell or administering to the patient or subject an effective amount of a chemotherapeutic drug or agent, e.g., a TKI, or a platinum drug or agent that targets EGFR, e.g., cisplatin, paclitaxel, erlotinib or dasatinib.

In therapeutic applications, a pharmaceutical composition containing one or more polypeptide or other therapeutic composition (e.g., antibody or siRNA) described herein is administered to a patient suspected of, or already suffering from cancer, wherein said composition is administered in an amount sufficient to cure, or at least partially arrest, the symptoms of the disease (biochemical, histological and/or behavioral), including its complication and intermediate pathological phenotypes in development of the disease. In one aspect, administration is by intraperitoneal injection or orally.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the polypeptide of this invention to provide the therapeutic benefit in vitro or in vivo by at least 10%, 25%, 40%, 60%, 80%, 90% or 95% as compared to control. Determination of these parameters is well within the skill of the art. These considerations, as well as effective formulations and administration procedures are well known in the art and are described in standard textbooks.

The "therapeutically effective amount" will vary depending on the polypeptide or siRNA, the disease and its severity and the age, weight, etc., of the patient to be treated all of which is within the skill of the attending clinician. It is contemplated that a therapeutically effective amount of a polypeptide or siRNA described herein will provide the therapeutic benefit to the patient as compared to the absence of treatment. As such, tumor growth is suppressed or decreased. A therapeutically effective amount is distinguishable from an amount having a biological effect (a "biologically effective amount"). A biological effect, however, may not result in any clinically measurable therapeutically effect as described above as determined by methods within the skill of the attending clinician.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell, solid tumor or cancer being treated, and the subject being treated. Single or multiple administrations can be carried out with the dose level and pattern being selected by the treating physician. Suitable dosage formulations and methods of administering the agents can be found below.

The pharmaceutical compositions can be administered orally, intranasally, parenterally, injection, orally and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including oral, rectal, nasal, topical (including transdermal, aerosol, buccal and sublingual), vaginal, parenteral (including subcutaneous, intramuscular, intravenous and intradermal) and pulmonary. It will also be appreciated that the preferred route will vary with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient. Desirable blood levels of the agent may be maintained by a continuous infusion to provide a therapeutic amount of the active ingredient within disease tissue. The use of operative combinations is contemplated to provide therapeutic combinations requiring a lower total dosage of each component agent than may be required when each individual therapeutic compound or drug is used alone, thereby reducing adverse effects.

While it is possible for the agent to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier that constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound that enhances absorption or penetration of the agent through the skin or other affected areas. Examples of such dermal penetration enhancers include dimethylsulfoxide and related analogues.

The oily phase of the emulsions of this invention may be constituted from known ingredients in an known manner. While this phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier that acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with a suitable base comprising, for example, cocoa butter or a salicylate. Formulations suitable for vaginal administration may be presented as pessaries, tampons, creams, gels, pastes, foams or spray formulations containing in addition to the agent, such carriers as are known in the art to be appropriate.

Formulations suitable for nasal administration, wherein the carrier is a solid, include a coarse powder having a particle size, for example, in the range of about 20 to about 500 microns which is administered as a dry powder or in an inhaler device by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the agent.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies.

The following examples are intended to illustrate, and not limit, the inventions disclosed herein.

EXPERIMENTAL

Experiment No. 1

MRP does appear to have much weaker corporation between the N-terminus and ED, and also much weaker association with membranes, than that of MARCKS. In contrast to MARCKS, MRP may not cross-link actin filaments as efficiently as MARCKS (Wohnsland, F. et al. (2000) J. Struct. Biol. 131(3):217-224). MARCKS is tethered to the plasma membrane through its myristyl group along with ionic interactions between the membrane phospholipids (PIP2) and the MARCKS effector domain (ED).

Figure 1:
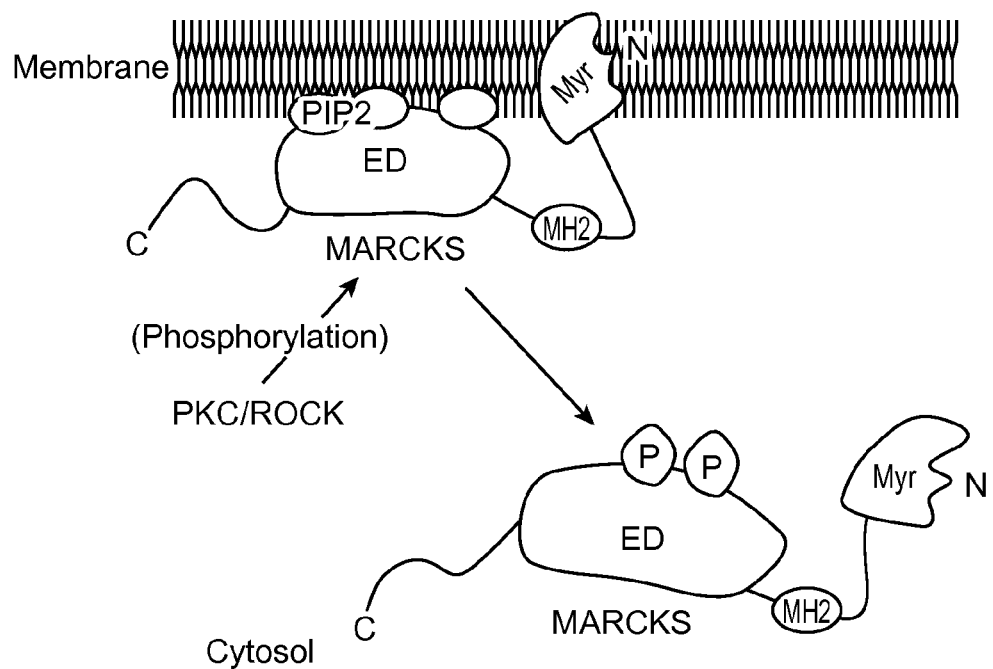
FIG. 1 shows that MARCKS is associated with membrane and its translocated to cytosol compartment after phosphorylation.

Phosphorylation of MARCKS by PKCs leads to its shuttling from the plasma membrane to the cytosol (FIG. 1) where it plays roles in cell migration through actin cytoskeletal remodeling, and regulation of exocytic vesicle release in secretory cells such as neurons and airway goblet cells (Li, Y. (2001) J. Biol. Chem. 276:40982-40990; Green, T. D. et al. (2011) Biochim. Biophys. Acta. 1810:1110-1113). In addition to PKCs, phosphorylation of MARCKS in certain tissues is regulated by other kinases such as Rho or MAP kinases. Particularly, serine 159 in MARCKS may be an important phosphorylation site, because it can be phosphorylated by both PKCs and Rho kinases (ROCK) (Tatsumi, S. et al. (2005) Neuroscience 131:491-498; Tanabe, A. et al. (2006) Biochem. Biophys. Res. Commun. 345:156-161). Activation of Rho kinases have been linked to metastasis and their inhibition by ROCK inhibitors has shown promise in cancer therapy (Chen, Y. et al. (2011) Cancer Res. 71:1721-1729; Liu, S. et al. (2009) Cancer Res. 69:8742-8751; Ying, H. et al. (2006) Mol. Cancer Ther. 5:2158-2164; Rath, N. et al. (2012) EMBO Rep. 13:900-908). Using both protein kinase C inhibitor (Calphostin C) and/or ROCK inhibitor (Y27632), Applicants have observed both PKC and ROCK contributed to an increase of MARCKS phosphorylation in these invasive lung cancer cells. This result suggests that at least Ser159 phosphorylation of MARCKS could be a convergence between PKC and ROCK signaling in lung cancer. The other phosphorylation site at Ser163, which is only phosphorylated by PKC, but not by ROCK (Tatsumi, S. et al. (2005) Neuroscience 131:491-498; Tanabe, A. et al. (2006) Biochem. Biophys. Res. Commun. 345:156-161). Applicants' work with lung cancer specimens from NSCLC patients confirmed the clinical significance of p-MARCKS elevated in cancer tissue section, but not in the adjunct non-tumor site. A similar observation has been found in breast cancer tissues in a tissue array study.

MARCKS Phosphorylation Site (MPS) Peptide is Effective in Suppressing Cancer Growth and Metastasis In Vivo

TABLE 1

Quantitative assessment of lung cancer metastatis inhibition by MPS peptide. Quantification of the average pulmonary metastatis nodules from mice with injected cancer cells and treated with RNS or MANS peptide as described (*P < 0.05 versus Con).

| | | | Lung Implantation | | | |
|---|---|---|---|---|---|---|
| Group | Primary tumor size (mm) Mean ± SE | No. of metastatic lung tumors Mean ± SE (R't) | Heart | Metastases Diaphragm | Liver | Spleen |
| Con (n = 4) | 1.73 ± 0.45 | 3.89 ± 0.51 | 2/4[1] | 3/4[1] | 1/4[1] | 1/4[1] |
| RNS (n = 6) | 1.52 ± 0.31 | 4.12 ± 1.72 | 3/6[1] | 4/6[1] | 2/6[1] | 1/6[1] |
| MPS (n = 6) | 0.68 ± 0.47* | 0* | 0/6[1] | 0/6[1] | 0/6[1] | 0/6[1] |

[1]Incidence: affected mice/total examined mice.
*Significant difference between Con and MANS-treated groups at $P < 0.05$.

Figure 2:
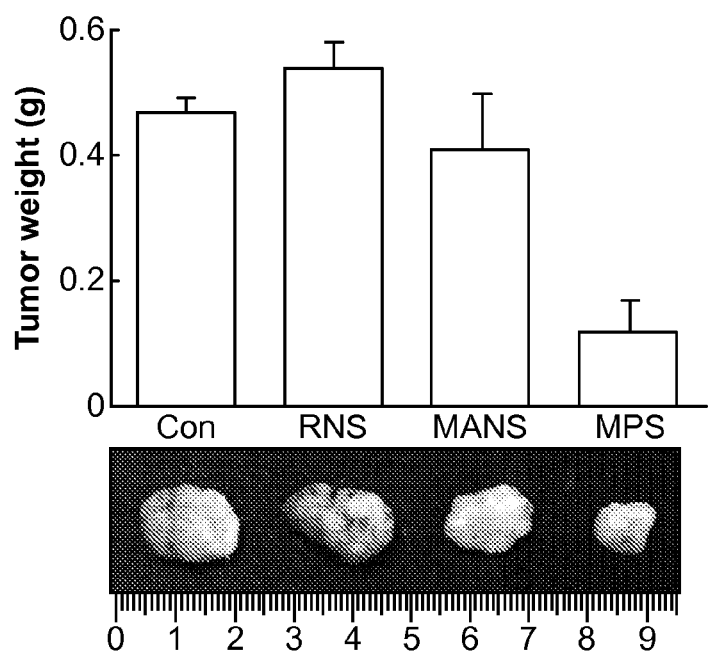
FIG. 2 shows inhibition of tumor growth in vivo by MPS peptide in xenograft nude mice bearing subcutaneous tumors were treated for 21 days with every two days intratumoral injections of PBS (control), RNS (scramble peptide), MANS or MPS peptide at the dosage of 50 nmoles. (Top) The tumour weights are average values from 6 mice per group. Data are Means±SE., * P<0.01 for comparison of control group (PBS). (Bottom) Representative photos of primary tumours from subcutaneous tissue of nude mice.
Figure 3:
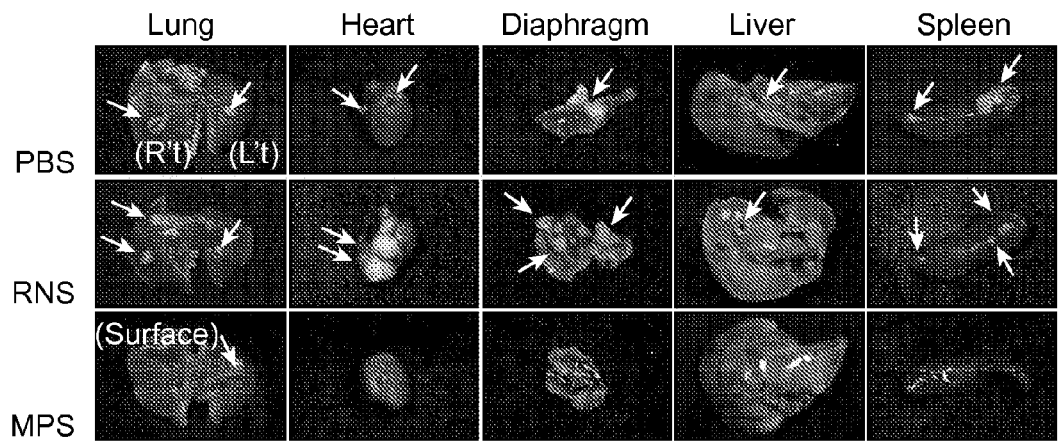
FIG. 3 (multiple panels) shows inhibition of lung cancer cell metastasis in vivo by MPS. Dissociated PC9 lung cancer cells were orthotopically injected to the left lobe lung of the mouse. After 4 days, mice were injected intraperitoneally with 500 μl of PBS or with PBS containing either the RNS (scramble peptide) or MPS peptide (100 nmoles) once every three days thereafter for a total of 10 injections up to day 32. At day 32, mice were sacrificed and organs were removed and examined. Gross pictures of various organs removed from mice. The arrows indicate tumor nodules in the organ.

Applicants designed an oligo peptide whose sequence (KKKKKRFSFKKSFKLSGFSFKKNKK)(SEQ ID NO: 9) corresponds to the ED domain of MARCKS since this is the site specifically for MARCKS phosphorylation. Using this peptide, as compared to a random control peptide (RNS) and MANS peptide, Applicants were able to show that MPS is very effectively in suppressing human lung cancer growth in mouse xenograft model (FIG. 2), while other peptides (RNS and MANS) at the same level of the treatment were not effective. In addition, Applicants have also observed the effectiveness of the MPS peptide treatment in the suppression of human lung cancer cell metastasis in vivo in an orthotopic lung implementation protocol (FIG. 3). Table 1 has summarized the quantitative data of this in vivo metastasis study. Clearly, MPS is very effective in the suppression of lung cancer cell metastasis, while RNS peptide and control vehicle treatments, cancer cell metastasis to different organs occur in most of the animals used in this study. Interestingly, the size of the primary tumor at the injected site is also suppressed by MPS treatment (Table 1). Thus, these data further support the potential usage of MPS in the treatment of lung cancer in terms of the inhibition of tumor growth and their metastasis.

Figure 4:
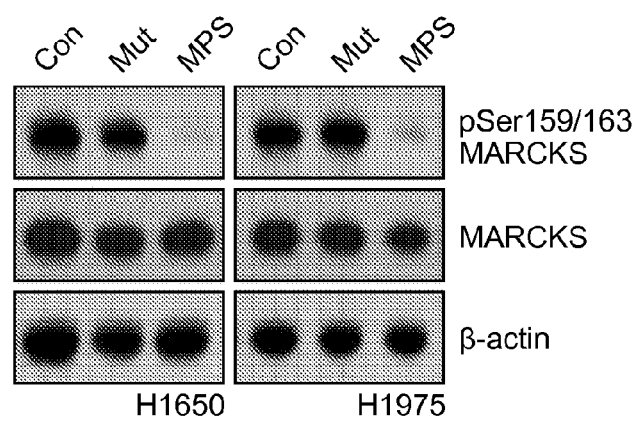
FIG. 4 shows effects of MPS treatment on MARCKS phosphorylation. The levels of MARCKS phosphorylation in chemoresistant cancer cell lines after 24 hours of MPS or mutant (Mut) peptide treatment. Lysates form 100 μM MPS-or Mut peptide-treated H1650 or H1975cells were subjected to immunoblotting. The sequences of MARCKS MPS peptide consisted of amino acids 152 to 176 from the wild-type protein (SEQ ID NO: 9). The sequences of mutated MPS peptide (Mut) (SEQ ID NO: 14) had the replacement of serine residues (S) by aspartate (D) and are unable to be recognized by PKC. The underline represents the PIP2 binding site.

Molecular Mechanisms of MPS Peptide in the Inhibition of Lung Cancer Cell Growth and Metastasis 1. Suppression of MARCKS Phosphorylation MARCKS is cycling on and off membranes by the myristoyl-electrostatic switch through both the interactions of N-terminus myristoylation and ED domain. Phosphorylation on ED domain is one the mechanisms that causes P-MARCKS detached from membrane, and it is then interacted with actin cytoskeleton in mediating cell migration and mucus granule discharge. As shown in FIG. 4, MPS treatment is very effective in suppressing p-MARCKS, while there is no suppression in cells treated with control vehicle and mutant (Mut) MPS. This finding is consistent with the MANS peptide treatment. Interestingly, there is no loss of total MARCKS protein in these cells after these peptide treatments. The molecular basis of the loss of P-MARCKS by MPS is currently under investigation.

2. Suppression of PIP3 Pool and Induction of Cell Death

Figure 5:
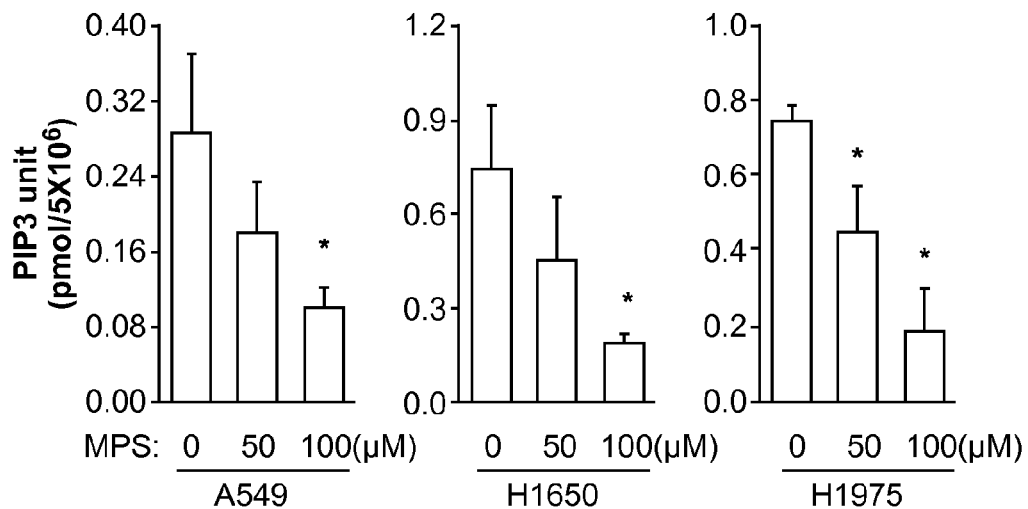
FIG. 5 shows suppression of PIP3 level by MPS. The levels of PIP3 in chemoresistant cancer cell lines after MPS peptide treatment. A549, H1650 and H1975 were treated with 50 or 100 μM MPS peptide. After 24 hours of treatment, PIP3 were extracted from these cells and analyzed by PIP3 ELISA kit. *, P<0.05 compared with untreated cells.
Figure 6:
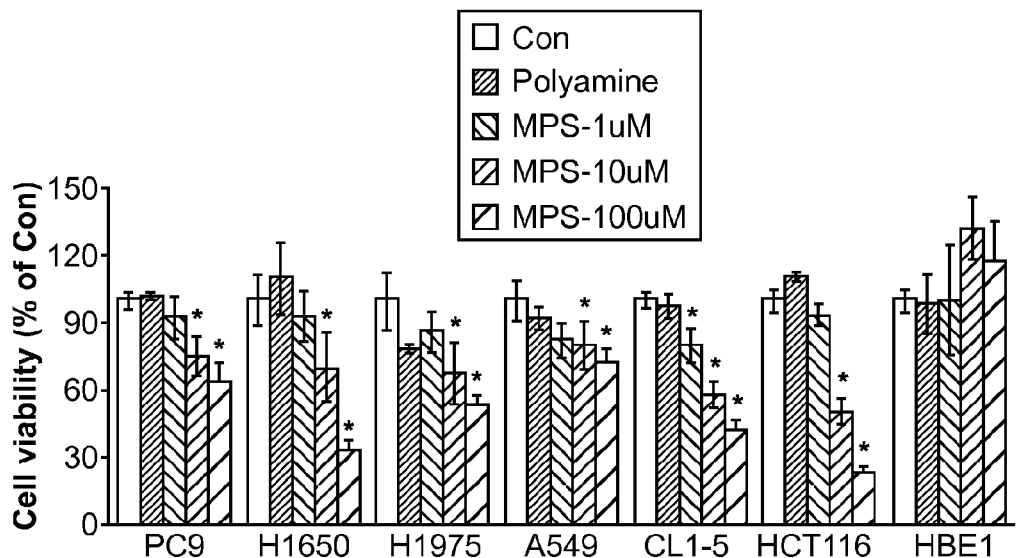
FIG. 6 shows cytotoxic effects of MPS peptide in various cancer cell lines, particularly in the cell lines with upregulation of PI3K/AKT pathway. Top, cells were incubated with various concentrations of MPS peptide for 72 hours and then subjected to a MTS assay for analysis of cell viability. Polyamine served as a peptide control. *, P<0.05 compared with untreated cells. The HBE1 cell line is a normal bronchial epithelial cell line. Bottom, ethnicities of the cancer cell lines used for MTS assay.
Figure 7:
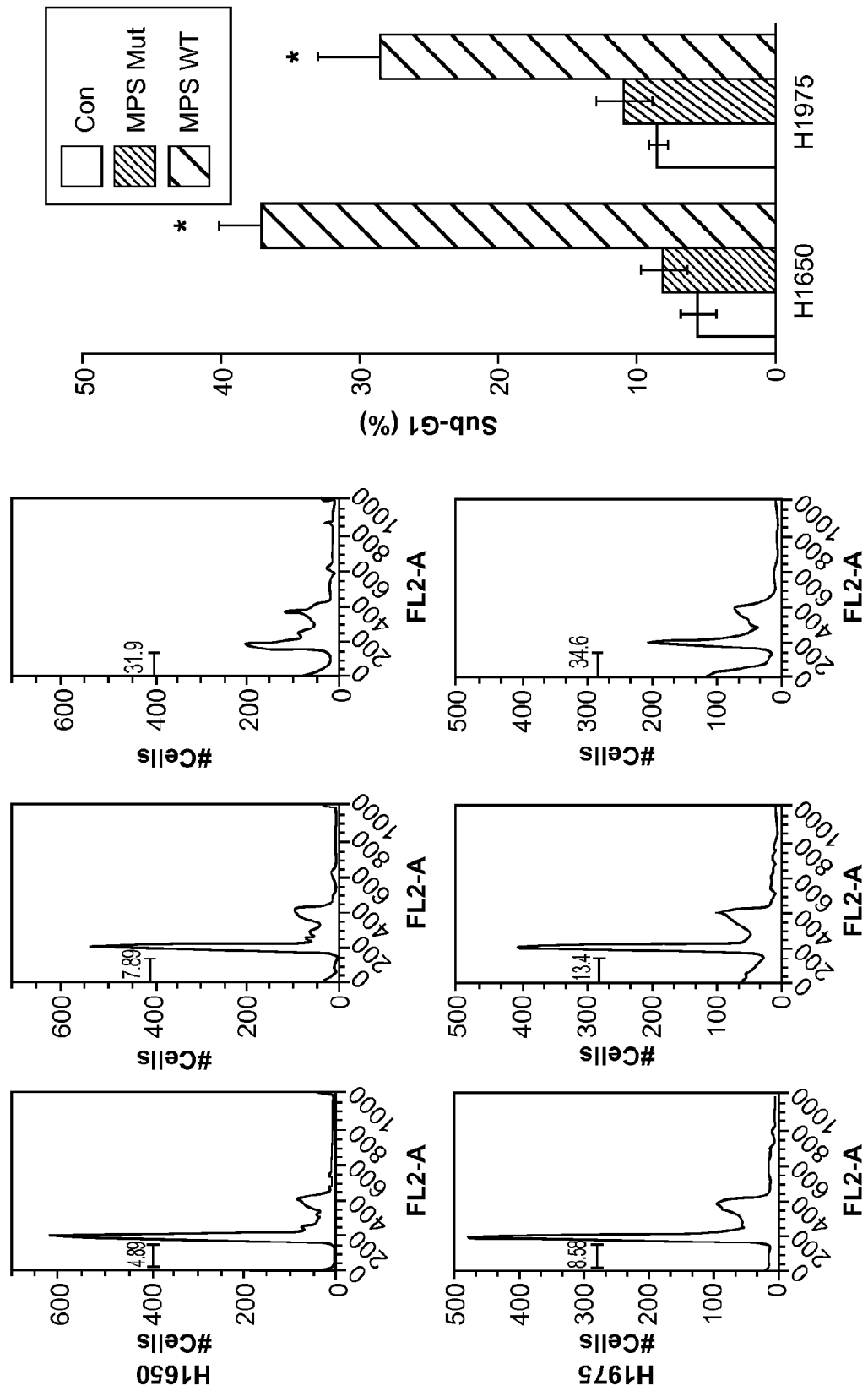
FIG. 7 shows enhanced apoptosis in lung cancer cells after MPS treatment. MPS treatment augments cell death. H1960 and H1975 cells were exposed to MPS or mutant peptide for 48 hours. The percentages of apoptotic cells were quantified by flow cytometry (Left), and presented as mean±S.D. of three experiments (Right). *, P<0.05 compared with untreated cells.

ED domain of MARCKS protein had been reported to directly bind to PIP2 and lead to a sequester of cellular PIP2 levels, which leads to a reduction of PIP3 pool. PIP3 is an essential trigger of AKT activation in most cancer cells. Pep-fold algorithm analysis has provided 5 predictions of MPS peptide and docking simulations with Autodock-Vina has demonstrated 9 best binding poses for the PIP2 head molecules. This model prediction has suggested the efficacy of the sequester of membrane PIP2 binding by MPS peptide. To further confirm this notion, Applicants have carried out PIP3 analysis in cells after MPS treatment. As shown in FIG. 5, MPS treatment is able to suppress the PIP3 level in these TKI-resistant cancer cells including A549, H1650, and H1975 cells. PIP3 play an important role in activation of AKT activation and also has diverse effects on the formation and progress of cancer. Since MPS treatment causes a decrease of cellular PIP3, Applicants first confirm the effect of MPS peptide on cell survival by analysis of cell viability. Six cancer cell lines and one normal bronchial epithelial cell line (HBE1) were treated with various dosage of MPS peptide for 72 hours. The impaired cell viability was found in MPS-treated cancer cells, but not in HBE1 epithelial cells (FIG. 6). Interestingly, the cytotoxicity effect of MPS peptide is obvious in the chemoresistant cancer cells with sustained AKT activation due to loss/mutation of PI3KCA or PTEN including H1975, HCT116, H1650 and CL1-5 cells (FIG. 6). To further confirm whether the reduced cell viability is through apoptosis-mediated cell death, two chemoresistant cell lines (H1650 and H1975) were incubated with a MPS or mutated MPS peptide (Mut). After 48 hours, Applicants performed flow cytometry and analyzed the ratio of sub-G1 population (identified as apoptosis) in these cells. Consistent with cell viability data, MPS peptide cause around 4-fold increase in cell death (FIG. 7). These results suggest the basis of MPS cytotoxicity on various cancer cells through the deprivation of PIP3 level and an enhanced apoptosis.

3. Enhance Drug-Treatment by MPS

Figure 8:
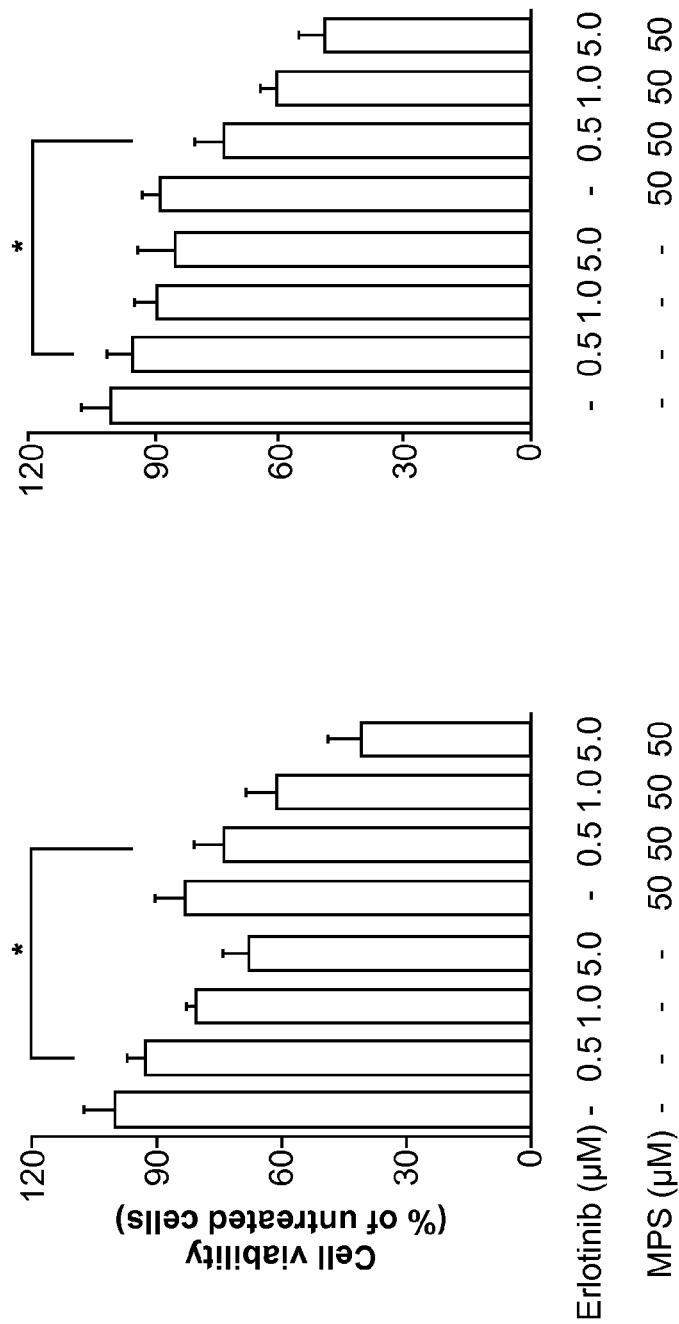
FIG. 8 shows enhancing chemo-sensitivity by MPS treatment. The combinatorial effect of MPS peptide with erlotinib on cancer cell lines. Two chemoresistant lung cancer cells, H1650 (Left) and H1975 (Right) cells were respectively co-treated with various dosages of erlotinib and 50 μM MPS peptide. After 48 hours, cell viability was determinate by MTS assay. *, P<0.05.

Based on above observation, Applicants presumed that co-treatment with MPS peptide may enhance drug sensitivity of these tyrosine kinase inhibitor (TKI) resistant cells. The two erlotinib resistant cell lines such as H1650 and H1975 were respectively co-treated with various dose of erlotinib and 50 µM MPS peptide for 48 hours. 0.5 µM erlotinib alone treatment has no significant decrease in cell viability compared to untreated cells (FIG. 8). However, erlotinib treatment combined with 50 µM MPS peptide resulted in ~20% loss of cell viability in both H1650 and H1975 cells. Particularly, there is an obvious synergetic effect found in H1975 cell line, which is more TKI resistant than H1650 line. These results suggest the potential of MPS peptide in synergism with the epidermal growth factor receptor inhibitor erlotinib in lung cancer treatment.

In summary, MPS is more sensitive than MANS in the treatment of lung cancer cells and tissues. MPS is able to suppress lung cancer growth and metastasis through the following mechanisms: inhibition of MARCKS phosphorylation and F-actin interaction; inhibition of PIP3 level through the sequestration of PIP2; inhibition of AKT activation and enhancing apoptosis and enhancing drug sensitivity.

Through the Pep-fold algorithm analysis and experimental data and without being bound by theory, Applicants believe that the central region of MPS peptide (KK-KRFSFKKSFK) that contains the basic amino acid cluster (KKK . . . KK . . . K), the phenyl alanine (—F—F—F—), and the two serine molecules interact with membrane-associated PIP2 and competing MARCKS' ED domain phosphorylation, can achieve a similar activity as that in MPS.

Experiment 2

A Novel Predictor of Cancer Malignancy: Up-Regulation of Myristoylated Alanine-Rich C Kinase Substrate Phosphorylation in Lung Cancer Lung cancer currently remains the leading cause of cancer-related deaths because of its aggressive nature. The 5-year survival rates for localized and regional disease are 54 and 26%, respectively, but only 4% for patients with late-stage (stage IV) disease (Siegel, R. et al. (2014) CA Cancer J. Clin. 64:9-29). Thus, development of biomarkers to identify patients at high risk for aggressive progression is of urgent need. Recently, Applicants reported myristoylated alanine-rich C kinase substrate (MARCKS), predominantly its phosphorylated state, as a risk factor associated with lung cancer invasiveness and metastasis (Chen, C. H. et al. (2013) Oncogene 33(28):3696-3706). MARCKS is a substrate of protein kinase C, and also a membrane-associated protein. Upon phosphorylation at Ser159 and Ser163 within its phosphorylation site domain, phosphorylated MARCKS (phospho-MARCKS) is detached from the plasma membrane and is able to regulate various cellular processes, including cell migration and exocytic vesicle release (Chen, C. H. et al. (2013) Oncogene 33(28):3696-3706; Li, Y. et al. (2001) J. Biol. Chem. 276:40982-40990; Chen, X. et al. (2010) Cell Signal 22:1097-1103). In the lungs, MARCKS has been extensively studied because of its role in regulating mucus secretion and inflammation. Inhibition of MARCKS activity not only reduces airway mucus hypersecretion both in vitro and in vivo (Li, Y. et al. (2001) J. Biol. Chem. 276:40982-40990; Singer, M. et al. (2004) Nat. Med. 10:193-196), but also represses inflammatory leukocyte migration and degranulation (Takashi, S et al. (2006) Am. J. Respir. Cell Mol. Biol. 34:647-652; Eckert, R. E. et al. (2010) Am. J. Respir. Cell Mol. Biol. 42:586-594). There have been limited studies on MARCKS in cancer metastasis, but the results have been conflicting (Rombouts, K. et al. (2013) Cancer Lett. 333:244-252; Jarboe, J. S. et al. (2012) Clin. Cancer Res. 18:3030-3041; Micallef, J. et al. (2009) Cancer Res. 69:7548-7556; Kim, N. G. et al. (2002) Oncogene 21:5081-5087; Masaki, T. et al. (2005) Int. J. Oncol. 26:661-671; Hanada, S. et al. (2013) Cancer. Biomark. 13:289-298). This is because MARCKS expression is ubiquitous in various normal and tumor tissues. Despite this, there is a consensus that phospho-MARCKS, a post-translational modification, is associated with cell motility, and has a role in the regulation of cancer cell invasiveness and metastasis (Chen, C. H. et al. (2013) Oncogene 33(28):3696-3706; Chen, X. et al. (2010) Cell Signal 22:1097-1103; Techasen, A. et al. (2010) Cancer Sci. 101:658-665; Reddy, M. M. et al. (2011) Leukemia 25:281-289). Of note, Applicants previously reported that inhibition of MARCKS phosphorylation was able to reduce lung cancer metastasis in murine models (Chen, C. H. et al. (2013) Oncogene 33(28): 3696-3706). However, the clinical significance of phospho-MARCKS in different cancers was yet to be determined. In particular, there was limited information regarding its relevance in cancer progression, especially lung cancer.

Figure 9:
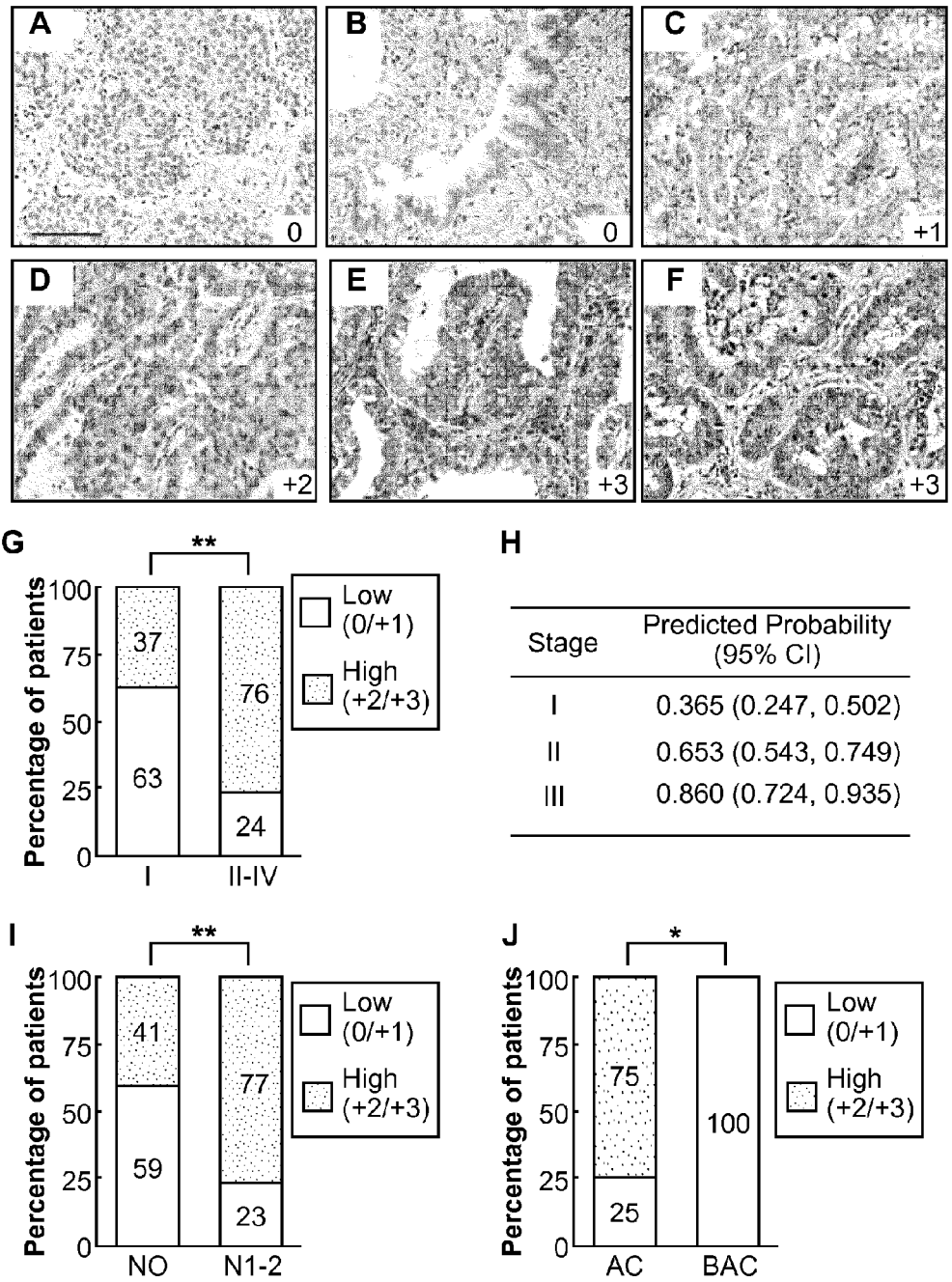
FIGS. 9A-9J show high phosphorylated myristoylated alanine-rich C kinase substrate (phospho-MARCKS) levels correlate with advanced stages, lymph node metastasis, and invasion of lung cancer. (A-F) Representative images of immunohistochemical staining using anti-pSer159/163 MARCKS monoclonal antibody in normal lung tissue and lung cancer specimens with low levels and high levels of phospho-MARCKS. Scale bar=100 μm. (A) Staining with normal mouse IgG as negative control (score=0). (B) Negative staining of phospho-MARCKS in normal lung bronchi. (C) Weak staining of phospho-MARCKS in lung cancer with stage I (score=+1). (D) Moderate staining of phospho-MARCKS in lung cancer with stage II (score=+2). (E and F) Strong staining of phospho-MARCKS in lung cancer with stage III (E) and IV (F) (score=+3). (G) Percentage of patients with high levels (score=12 and 13) and low levels (score=0 and +1) of MARCKS phosphorylation according to tumor stage. (H) Predicted probability of high phospho-MARCKS levels with different stages of lung cancer. (I and J) Percentage of patients with high and low levels of MARCKS phosphorylation according to lymph node status (I) and cancer types (J). Numbers in bars represent the percentage of patients for each condition. AC=invasive adenocarcinoma; BAC=bronchoalveolar carcinoma; CI=confidence interval. *P=0.014, **P<0.001, n=110 (G and I); n=52 (J).

Based on 18 pairs of normal and malignant lung cancer tissue sections, Applicants reported that elevated phospho-MARCKS was seen in malignant lung cancer tissue sections, but not in their adjacent normal counterparts (Chen, C. H. et al. (2013) Oncogene 33(28):3696-3706), suggesting a potential association between MARCKS phosphorylation and more aggressive lung cancer histological grades. To investigate more fully this previous finding, samples Applicants analyzed from a cohort of 110 human patients with lung cancer using immunohistochemical staining with an anti-pSer159/163 MARCKS monoclonal antibody. The clinical characteristics of these patients are summarized in Table 2. Consistent with the previous report (Chen, C. H. et al. (2013) Oncogene 33(28):3696-3706), high levels of MARCKS phosphorylation were found in tumor tissues compared with normal lung tissues (FIGS. 9A-9F). Weak phospho-MARCKS staining was observed in the cytoplasm of lung cancer tissue samples from patients in Stage I (FIG. 9C). In contrast, strong MARCKS phosphorylation occurred in advancedstage lung cancer tissue samples (FIGS. 9D-9F). The levels of MARCKS phosphorylation correlated significantly with advanced stages of disease (FIG. 9G, Pearson's Chi-square test).

TABLE 2

Phosphorylated Myristoylated Alanine-Rich C Kinase Substrate Levels in Relation to Clinicopathologic Characteristics of Patients with Non-Small Cell Lung Cancer[§]

| Characteristic | Total Patients | High [No. of Patients (%)] | Low [No. of Patients (%)] | P Value |
|---|---|---|---|---|
| Number of patients, n | 110 | 65 | 45 | |
| Age, yr (mean ± SD) | 56.3 ± 9.5 | 56.5 ± 9.8 | 56.0 ± 9.1 | 0.768* |
| Sex, n | | | | 0.213[†] |
| Male | 75 | 41 (37.3) | 34 (30.9) | |
| Female | 35 | 24 (21.8) | 11 (10.0) | |
| Stage, n | | | | <0.001[†] |
| I | 48 | 18 (16.4) | 30 (27.3) | |
| II | 29 | 18 (16.4) | 11 (10.0) | |
| III | 32 | 28 (25.5) | 4 (3.6) | |
| IV | 1 | 1 (0.9) | 0 (0.0) | |
| Cell type, n | | | | 0.045[†] |
| Adenocarcinoma | 48 | 33 (30.0) | 15 (13.6) | |
| Squamous cell carcinoma | 41 | 23 (20.9) | 18 (16.4) | |
| Bronchioloalveolar carcinoma | 4 | 0 (0.0) | 4 (3.6) | |
| Other | 17 | 9 (8.2) | 8 (7.3) | |
| Regional lymph node, n | | | | <0.001[†] |
| N0 | 54 | 22 (20.0) | 32 (29.1) | |
| N1 | 44 | 32 (29.1) | 12 (10.9) | |
| N2 | 12 | 11 (10.0) | 1 (0.9) | |

[§]Patients were grouped by high levels (score = +2 and +3) and low level (score = 0 and +1) of MARCKS phosphorylation.
*T test.
[†]Fisher's exact test.

To quantitatively investigate these impressions, bivariate logistic regression models to predict the likelihood of high phospho-MARCKS levels from advanced tumor stages were estimated, and the probabilities of high phospho-MARCKS with Stage I to III are shown in FIG. 9H. The analyses demonstrated that, for a one-unit increase in Stages II and III, the log odds of high expression of phospho-MARCKS levels increased by 1.00 and 2.46 compared with Stage I. There were significant differences in the logistic probabilities of high phospho-MARCKS levels between Stages I and II (P=0.039), as well as Stages I and III (P<0.001), respectively. These results suggest that phospho-MARCKS may be a promising clinical predictor of tumor stages in patients with lung cancer.

Moreover, Applicants also investigated the significance of phospho-MARCKS in lymph node status and found that higher levels of MARCKS phosphorylation correlated with lymph node metastasis (FIG. 9I, N0 versus N1-2). Notably, MARCKS phosphorylation was lower in a subtype of adenocarcinoma, bronchoalveolar carcinoma, which shows a less invasive phenotype than adenocarcinoma (FIG. 9J, AC versus bronchoalveolar carcinoma). Because tumor necrosis is a common event in aggressive cancers, Applicants further checked phospho-MARCKS levels in the 10 tumor tissues with necrosis in this set of tissue arrays. Interestingly, higher staining intensity and increased numbers of cells stained with anti-phospho-MARCKS antibody was found in these tumors. These data raise the possibility that high phospho-MARCKS levels may contribute to cancer progression in non-small cell lung cancers, and the detection of phospho-MARCKS could potentially be used as a prognostic biomarker for the disease.

In summary, Applicants demonstrated that higher MARCKS phosphorylation is correlated with lung cancer in advanced stages (Stage II-IV), lymph node metastatic status, and malignant phenotypes. In addition (Chen, C. H. et al. (2013) Oncogene 33(28):3696-3706), the reported work further confirms the importance of phospho-MARCKS in driving the progression of lung cancer toward more malignancy, suggesting that phospho-MARCKS levels may determine the progression of localized lung cancer toward late stage. Taken together, high phospho-MARCKS levels appear to confer cancer malignancy, and may serve as a novel biomarker. Inhibition of MARCKS phosphorylation, the post-translational step, may be an effective strategy for controlling lung cancer progression.

Experiment 3

Targeting MARCKS Phosphorylation Site Domain in Lung Cancer: Mechanism and a Therapeutic Implication Phosphorylation of myristoylated alanine-rich C-kinase substrate (phospho-MARCKS) at the phosphoryation site domain (PSD) is important for the control of mucus granule secretion and cell motility. However, very little information is available for the function of phospho-MARCKS in lung cancer progression and chemotherapeutic treatment response. Using shRNA silencing and ectopic expression of wild type and PSD-mutated (S159/163A) MARCKS, Applicants report herein that elevated phospho-MARCKS conferred cancer cell resistance to tyrosine kinase inhibitors (TKIs) and also promoted the growth of cancer cells in vitro as well as in vivo. In addition, the phospho-MARCKS level was correlated with grades of primary tumor status (T) from patients. Further studies have demonstrated an interaction of PI3K with MARCKS, but not phospho-MARCKS. Interestingly, the level of phospho-MARCKS was parallel with PIP3 pools and AKT activation in cells. Through treatment with a 25 amino-acid peptide targeting the MARCKS phosphorylation site domain (the MPS peptide), tumor growth and metastasis was suppressed in vivo, and levels of phospho-MARCKS, PIP3, and AKT activity were reduced. The MPS peptide also enhanced the sensitivity of TKIs resistant lung cancer cells to erlotinib treatment, especially with sustained activation of PI3K/AKT signaling, both in vitro and in vivo. These results suggest a key role for MARCKS PSD in cancer disease and provide a unique strategy for inhibiting the activity of MARCKS PSD as a treatment for lung cancer.

Lung cancer remains the leading cause of cancer mortality worldwide, accounting for more than one-quarter of all cancer deaths (Siegel, R. et al. (2014) CA Cancer J. Clin.). Cancer metastasis and drug resistance are the main reasons for the poor survival of patients with non-small cell lung cancers (NSCLCs). Standard treatment approaches, including chemotherapy, radiotherapy and surgery, are often associated with unsatisfying outcomes because most lung cancer patients (70%) are diagnosed at advanced stages (stage II-IV) (Siegel, R. et al. (2014) CA Cancer J. Clin.; Crino, L. et al. (2010) Ann Oncol. 21(Suppl. 5):v103-v115). Alternatives to conventional treatment are in dire need and new molecular-targeted therapies, such as targeting the epidermal growth factor receptor (EGFR), have played a central role in lung cancer treatment in recent years. Two EGFR inhibitors, gefitinib and erlotinib, are currently used as first-line treatment options for patients with the EGFR mutation (Rosell, R. et al. (2012) Lancet Oncol. 13:239-246; Keedy, V. L. et al. (2011) J. Clin. Oncol. 29:2121-2127). Unfortunately, variable rates of responsiveness to this targeted therapy as well as the ability of lung cancer to develop resistance to these inhibitors has brought about new challenges in clinical practice (Stinchcombe, T. E. et al. (2009) Proc Am Thorac Soc. 6:233-241; Wheeler, D. L. (2010) Nat Rev Clin Oncol. 7:493-507). The development of novel biomarkers and effective therapeutic interventions are greatly needed.

Many cancers have activated phosphoinositide 3-kinase (PI3K)/AKT pathway, which is involved in the promotion and the regulation of cell proliferation, survival, motility and metabolism (Vivanco, I. et al. (2002) Nat Rev Cancer 2:489-501; Yamamoto, H. et al (2008) Cancer Res. 68:6913-6921). Of note, PI3K signaling is frequently activated by receptor tyrosine kinases (RTKs), such as EGFR, and eventually an overly activated PI3K/AKT signaling can confer drug resistance (Sos, M. L. et al. (2009) Cancer Res. 69:3256-3261; Buck, E. et al (2006) Mol. Cancer Ther. 5:2676-2684). Recent research has indicated inhibition of PI3K/AKT signaling as a possible therapeutic target, but it remains unknown which cancer types will benefit most from such an intervention (Courtney, K. D. et al. (2010) J. Clin. Oncol. 28:1075-1083; Gadgeel, S. M. et al. (2013) Clin. Lung Cancer 14:322-332). An important function of PI3K is to synthesize phosphatidylinositol (3,4,5)-triphosphate (PIP3), resulting in AKT activation and the subsequent regulation of various biological processes. Once the regulatory subunit (p85) of PI3K binds to phosphotyrosine residues on RTKs and/or adaptors, the catalytic subunit (p110) is free to catalyze the phosphorylation of phosphatidylinositol 4,5-bisphosphate (PIP2) to PIP3. However, it remains unclear on how PIP2 is accessible to PI3K (Zhao, L. et al. (2008) Oncogene 27:5486-5496; Carpenter, C. L. et al. (1993) J. Biol. Chem. 268:9478-9483).

MARCKS is a membrane-associated protein by the cooperative interaction of myristoylated N-terminal region and phosphorylation site domain and it is able to sequester acidic membrane phophoslipids, such as PIP2 in the inner leaflet of the plasma membrane. The MARCKS phosphorylation site domain (PSD), also known as the basic effector domain, is crucial for MARCKS functionality and it is also the major motif to electrostatically bind to PIP2 (Gambhir, A. et al. (2004) Biophys. J. 86:2188-2207; McLaughlin, S. et al. (2005) Nature 438:605-611). Phosphorylation by protein kinase C (PKC) within MARCKS PSD (Ser159, Ser163 and Ser170) enhances phospho-MARCKS detachment from membrane and suppresses PIP2 sequestering effect. Phospho-MARCKS acts as a key regulatory protein controlling cell migration and signaling (Aderem, A. (1992) Trends Biochem. Sci. 17:438-443; Arbuzova, A. et al. (2002) Biochem J. 362:1-12; Kalwa, H. et al. (2011) J. Biol. Chem. 286:2320-2330). There is growing evidence of a functional role for MARCKS expression in numerous cancers (Browne, B. C. et al. (2013) FEBS J.; Rombouts, K. et al. (2013) Cancer Lett. 333:244-252; Jarboe, J. S. et al. (2012) Clin. Cancer Res. 18:3030-3041; Manenti, S. et al. (1998) Cancer Res. 58:1429-1434; Brooks, G. et al. (1996) Carcinogenesis 17:683-689; Michel, S. et al. (2010) Mol. Carcinog. 49:175-182; Micallef, J. et al. (2009) Cancer Res. 69:7548-7556; Kim, N. G. et al. (2002) Oncogene 21:5081-5087; Masaki, T. et al. (2005) Int. J. Oncol. 26:661-671; Hanada S, et al. (2013) Cancer Biomark. 13:289-298), but only a few studies revealed the importance of phospho-MARCKS in cancer motility (Techasen, A. et al. (2010) Cancer Sci. 101:658-665; Reddy, M. M. et al. (2001) Leukemia 25:281-289; Chen, X. et al. (2010) Cell Signal 22:1097-1103; Yokoyama, Y. et al. (1998) Int. J. Cancer 75:774-749; Chen, C. H. et al. (2013) Oncogene). Despite this, understanding of phospho-MARCKS function and the contribution of the MARCKS PSD motif to lung cancer are incomplete. Recently, Applicants' laboratory discovered that the use of a MANS peptide, targeting MARCKS N-terminal myristoylation site, was able to reduce lung cancer metastasis (Chen, C. H. et al. (2013) Oncogene). However, the treatment had no effect on tumor growth in vivo. Thus, there is a need to test if other parts of MARCKS, especially the PSD motif, can be targeted for lung cancer treatment. In this study, Applicants test this potential and elucidate the molecular basis of this potential.

Materials and Methods
Materials, Plasmids, and Transfection
Reagents and Antibodies RPMI-1640 medium, fetal bovine serum and penicillin-streptomycin were purchased from Life Technologies Inc. (Carlsbad, Calif.). Lipofect-AMINE™ was purchased from Invitrogen (Carlsbad, Calif.). VECTASTAIN® Elite ABC Kit (Rabbit IgG), VECTOR® Hematoxylin QS nuclear counterstain and DAB solution were purchased from VECTOR Laboratories Inc. (Burlingame, Calif.). Protein A-Sepharose beads and glutathione Sepharose were purchased from Amersham Biosciences (Piscataway, N.J.). Propidium iodide was purchased from Sigma (St Louis, Mo.). Both anti-pSer159/163 MARCKS (clone EP2113Y) and anti-MARCKS (clone EP1446Y) were purchased from Epitomics (Burlingame, Calif.). Anti-pSer473 AKT, anti-pThr308 AKT, anti-AKT, anti-PI3K, anti-cleaved PARP, anti-cleaved caspase 3, anti-pTyr1068 EGFR, anti-EGFR and anti-β-actin antibodies were purchased from Cell Signaling Technology, Inc. (Danvers, Mass.). MARCKS siRNAs (MARCKS siRNA Smartpool) and DharmaFECT siRNA transfection reagents were purchased from Dharmacon, Inc. (Lafayette, Colo.).

Plasmid Constructs

For identification and cloning of the MARCKS full-length cDNA, total RNA was isolated from CL1-5 cells using Trizol reagent (Life Technologies). First-strand cDNA was reverse-transcribed with SuperScript II reverse transcriptase (Life Technologies) and oligo-dT primer. The MARCKS coding region was amplified by polymerase chain reaction (PCR) using the forward primer: 5'-GATC-CATGGGTGCCCAGTTCTCCAAGACCGCAGC-3' (SEQ ID NO: 34), which introduced a BamHI site, and the reverse primer: 5'-TCTAGACTCTCTGCCGCCT CCGCT GGGGGGGCT-3'(SEQ ID NO: 35), which introduced an XbaI site. The amplified product was cloned into pcDNA3.1 vector (Invitrogen). The cDNA was then fully sequenced to ensure that no mutations were introduced during the PCR amplification. For generation of MARCKS shRNA plasmids, the oligonucleotide of shRNAs (shRNA-a: 5'-GA-GAAGGCGGTGAGGCTGA-3' (SEQ ID NO: 15) and its complementary strand: 5'-TCAGCCTCACCGCCTTCTC-3' (SEQ ID NO: 16); shRNA-b: 5'-GAAGGTAAACGGC-GACGCT-3' (SEQ ID NO: 17) and its complementary strand: 5'-AGCGTCGCCGTTTACCTTC-3' (SEQ ID NO: 18); shRNA-c: 5'-GAGCGCTTCTCCTTCAAGAA-3' (SEQ ID NO: 19) and its complementary strand: 5'-TTCT-TGAAGGAGAAGCGCTC-3' (SEQ ID NO: 20)) were synthesized, annealed and cloned into the pGreenPuro shRNA expression lentivector (System Biosciences, Mountain View, Calif.). The S159/163A V5-tagged MARCKS was generated by site-directed mutagenesis and the mutagenic primers used were as follows: the S159A forward primer 5' GAAGCGCTTTGCCT-TCAAGAAGTCTTTCAAGCTGA-3'(SEQ ID NO: 36), and the reverse primer 5'-TCAGCTTGAAAGACTTCTT-GAAGCAAAGCGCTTC-3' (SEQ ID NO: 37); the S163A forward primer 5'-GAAGCCTTTTCCT-TCAAGAAGGCTTTCAAGCTGA-3' (SEQ ID NO: 38), and the reverse primer 5'-TCAGCTTGAAAGCCTTCTT-GAAGGAAAAGCGCTTC-3' (SEQ ID NO: 39). The desired mutations were confirmed by Sanger sequencing.

Cell Culture and Transfection

The CL1-0, CL1-0/F3 and CL1-5 were established as previously described (Chen, J. J. et al. (2001) Cancer Res. 61:5223-5230; Chen, C. H. et al. (2013) Oncogene). The cell lines, PC9, A549, H1650, H1975 and HCT116, were purchased from the American Type Culture Collection (ATCC) (Manassas, Va.). Cells were cultured in RPMI-1640 medium with 10% fetal bovine serum and 1% penicillin-streptomycin at 37° C. in a humidified atmosphere of 5% CO2. Normal human primary bronchial epithelial cells were grown in Clonetics BEGM medium (Cambrex Lonza, East Rutherford, N.J.) with all hormones/growth factors included in the package, except the retinoic acid. For siRNAs transfection, ON-TARGETplus MARCKS siRNA and scrambled siRNA sequences (Thermo Scientific, Pittsburgh, Pa.) were transfected using DharmaFECT according to the manufacturer's protocol.

For enforced expression of V5-tagged MARCKS in CL1-0, lung cancer cells were transfected with pcDNA3.1-MARCKS, pcDNA3.1-S159/163A MARCKS or pcDNA3.1 vector using lipofectamine reagent (Invitrogen), according to the manufacturer's protocol. After culturing in medium containing with 400 μg/mL of G418 (Invitrogen) for 2-3 weeks, individual clones were isolated. Clones that expressed the MARCKS cDNA coding region were maintained in medium containing 200 µg/mL of G418 and used for further investigation. Applicants also established a MARCKS-mixed knockdown stable A549 transfectant. The utilized lentiviruses were generated by cotransfection of HEK293T cells with the appropriate MARCKS shRNA-containing lentiviral vector and a packing DNA mix, using Lipofectamine 2000 (Invitrogen). Cells were infected at three different Multiplicities of Infection (MOIs) in polybrene (8 µg/mL)-containing medium. Twenty-four hours after infection, the cells were treated with puromycin (final concentration 2 µg/mL) and puromycin-resistant clones were selected and pooled.

Peptide Synthesis

The MPS, S/D mutant MPS (Mut), RNS and MANS peptides were purchased from EZBiolab Inc. (Carmel, Ind.) at a purity of 95%. The MPS peptide consisted of amino acids 151 to 175 from the wild-type protein, KKKK-KRFSFKKSFKLSGFSFKKNKK (SEQ ID NO: 9), and the mutated MPS (Mut) had a sequence KKKKKRFDFKKD-FKLDGFDFKKNKK (SEQ ID NO: 14). Peptides were reconstituted in phosphate-buffered saline, yielding stock concentrations of 10 mM. Stock solutions were stored at −20° C. and diluted to desired concentrations on the day of the experiment.

Cell Culture

The CL1-0, CL1-0/F3 and CL1-5 lung cancer cell lines were established and characterized as previously described (Chen, C. H. et al. (2013) Oncogene). Applicants tested their invasiveness for authentication by matrigel invasion assays in the laboratory every month. The cell lines, PC9, A549, H1650, H1975 and HCT116, were purchased from the American Type Culture Collection (ATCC; Manassas, Va.) that has performed cell line characterizations. These cell lines were passaged in the laboratory for fewer than 6 months after receipt and their characterizations had been periodically checked in the lab, following the method of characterization at ATCC website. The human HBE1 cell line was a gift from JR Yankaskas, University of North Carolina. Normal human primary bronchial epithelial cells were obtained from airway tissues provided from National Disease Research Interchange (NDRI) (Philadelphia, Pa.) and UC Davis Medical Hospital (Sacramento, Calif.) with consents. The protocol for human tissue procurement and usage were periodically reviewed and approved by the University Human Subject Research Review Committee.

Cell Viability and Colony Formation Assays

Cells were seeded onto 96-well plates at a density of $5$-$10 \times 10^3$ cells per well and cultured for the indicated treatment. Cell viability was evaluated using a MTS assay kit (Promega, Madison, Wis.). Twenty microliters of the combined MTS/PMS solution was added into each well, incubated for 3 hours at 37° C., and the absorbance was measured at 490 nm by using an ELISA reader. For the anchorage-dependent growth assay, 200 cells were seeded in each well of six-well plates. CL1-0 or A549 derived stable cells were cultured in complete culture medium for 10 days. H1975 or H1650 cells were treated with peptides at the indicated concentrations for 5 days and then changed to the complete culture medium; these cells were further incubated for 5 days. Colonies were stained using 0.001% crystal violet and the number of colonies with a diameter greater than 0.5 mm was counted under an inverted microscope.

Immunohistochemical Staining

Human lung cancer tissue array was purchased from Biomax Co. (Rockville, Md.; BC041115a). Detailed experimental procedures were modified from the paraffin immunohistochemistry protocol supplied by the manufacturer (Cell Signaling, Danvers, Mass.). Human lung cancer tissue array was purchased from Biomax Co. (Rockville, Md.; BC041115a). The slides were de-paraffinized in xylene and rehydrated in graded alcohol and water. An antigen retrieval step (10 nM sodium citrate (pH 6.0) at a sub-boiling temperature) was used for each primary antibody. Endogenous peroxidase activity was blocked by 3% hydrogen peroxide followed by blocking serum and incubation with appropriate antibodies overnight at 4° C. Detection of immunostaining was carried out by using the VECTASTAIN® ABC system, according to the manufacturer's instructions (Vector Laboratories, Burlingame, Calif.). A four-point staining intensity scoring system was devised to confirm the relative expression of phospho-MARCKS in cancer specimens; scores ranged from zero (no expression) to 3 (highest-intensity staining) as described previously (Lu, J. et al. (2009) Cancer Cell 16:195-207; Kuo, T. C. et al. (2013) J. Clin. Invest. 123:1082-1095). The results were classified into two groups according to the intensity and extent of staining: in the low-expression group, staining was observed in 0-1% of the cells (staining intensity score=0), or in less than 10% of the cells (staining intensity score=1); in the high-expression group, staining was present in 10%-50% of the cells (staining intensity score=2), or more than 50% of the cells (staining intensity score=3). These results were reviewed and scored independently by two pathologists.

PI(3,4,5)P3 Quantitation

Cells were harvested and precipitated by trichloroacetic acid, and the precipitated fraction was used twice for PIP3 lipids extraction by methanol:chloroform (2:1). After acidification, organic-phase lipids were used for PIP3 quantitation, based on the protocol for the PIP3 Mass ELISA kit (Echelon Biosciences, Salt Lake, Utah).

Cells were harvested and precipitated by trichloroacetic acid. PIP3 lipids were extracted twice from the trichloroacetic acid precipitated fraction by methanol:chloroform (2:1). After acidification, organic-phase lipids were used for PIP3 quantitation, based on the protocol for the PIP3 Mass ELISA kit (Echelon Biosciences, Salt Lake, Utah). Briefly, the lipid extract from cultured cells was mixed with the PIP3-specific detector protein, which was then incubated in a PIP3-coated mircroplate for competitive binding. After several washes, the microplate was then incubated with a HRP-linked secondary detector and tetramethylbenzidine substrate for color development. To stop further color development, 2M $H_2SO_4$ solution was then added. Microplates were read at an absorbance wavelength of 450 nm. A series of different dilutions of PIP3 standards were used for establishing a standard curve for each reaction. Cellular PIP3 amounts could be estimated by comparing the absorbance in the wells with the values in the standard curve. Experiments were conducted in triplicate dishes and repeated in two independent cultures with cell density $5 \times 10^6$ cells/100-mm dish.

Immunoblotting and Immunoprecipitation

The preparation of whole-cell lysates and western blot analysis have been described previously (Chen, C. H. et al. (2013) Oncogene). Briefly, cells were lysed in a lysis buffer (50 mM Tris/HCl (pH 7.4), 1% Triton-X 100, 10% glycerol, 150 mM NaCl, 1 mM EDTA, 20 µg/ml leupeptin, 1 mM PMSF, 20 µg/ml aprotinin and 20 µg/ml pepstatin) and cleaned by pre-incubation with protein A-sepharose beads to remove non-specifically bound proteins. After precipitation with appropriate antibodies and protein A-sepharose beads, the immunoprecipitated complexes were washed and separated by SDS-PAGE. Immunoblotting was done with appropriate antibodies using the Amersham Biosciences (Pittsburgh, Pa.) enhanced chemiluminescence system for detection.

Flow Cytometry

Cells were seeded at a density of 2×105 cells/60-mm dish in complete culture medium and treated with or without peptide for 48 hours. Each sample was harvested and stained with 25 µg/mL propidium iodide. These samples were analyzed by flow cytometry using a Cytomics™ FC500 flow cytometer (Beckman Coulter), according to the manufacturer's protocol.

In Vivo Subcutaneous and Orthotopic Implantations

Animal usage protocols were periodically reviewed and approved by Institutional Animal Care and Use Committee at UC Davis. Six-week-old nude mice (supplied by Charles River Laboratories, San Diego, Calif.) were housed four mice per cage and fed autoclaved food ad libitum.

Six-week-old nude mice (supplied by Charles River Laboratories, San Diego, Calif.) were housed four mice per cage and fed autoclaved food ad libitum. For the in vivo tumorigenesis assay, the dorsal region of nude mice was injected subcutaneously with 2×106 MARCKS shRNA-silenced A549 cells or A549 control cells. After 28 days, the xenografted tumors were removed, weighed and fixed in 10% formalin; embedded tissues were sliced into 4 µm sections, which were stained with hematoxylin-eosin and anti-PCNA antibody for histological analysis. For the in vivo treatment of peptide or drug assays, the dorsal regions of nude mice were injected subcutaneously with $5 \times 10^6$ H1975 cells and these mice were examined every 3 days for tumor size. Groups were randomized and treatment started when tumor size reached 60-80 mm$^3$ (the tumor volume was calculated by using the formula V=0.4Xab$^2$, where a and b are the longest and shortest diameters of the tumors, respectively). These nude mice bearing subcutaneous tumors were intraperitoneally (i.p) injected with PBS, Mut peptide (28 mg/kg), MPS peptide (28 mg/kg), erlotinib (14 mg/kg or 28 mg/kg) alone or MPS peptide (28 mg/kg) combined with erlotinib (14 mg/kg) every three days. After 21 days of treatment, these mice were sacrificed and the xenografted tumors were collected for histological analysis. For orthotopic implantation, PC9 cells ($5 \times 10^4$ cells in 40 µl PBS containing 10 ng Matrigel) were inoculated into the left lung of mice by insulin syringe with 29-G needle. After 7 days of implantation, the mice were subjected to systemic treatment with PBS, RNS (14 mg/kg) or MPS peptide (14 mg/kg) by intraperitoneal injections once every three days. The mice were sacrificed after a total of 10 injections of treatment. The numbers of lung tumor colonies from orthotopic implanted mice were evaluated by gross and microscopic examination.

TABLE 3

Phospho-MARCKS levels in relation to clinicopathologic characteristics of the NSCLC patients

| Characteristic | Total patients | High No. of Patients (%) | Low No. of Patients (%) |
|---|---|---|---|
| Number of patients | n = 110 | n = 65 | n = 45 |
| Age (mean ± SD) | 56.3 ± 9.5 | 56.5 ± 9.8 | 56.0 ± 9.1 |
| Gender | | | |
| Male | 75 | 41 (37.3) | 34 (30.9) |
| Female | 35 | 24 (21.8) | 11 (10.0) |
| Tumor status | | | |
| T1 | 11 | 6 (5.5) | 5 (4.5) |
| T2 | 74 | 38 (34.5) | 36 (32.7) |
| T3 | 22 | 19 (17.3) | 3 (2.7) |
| T4 | 3 | 2 (1.8) | 1 (0.9) |

TABLE 3-continued

Phospho-MARCKS levels in relation to clinicopathologic characteristics of the NSCLC patients

| Characteristic | Total patients | High No. of Patients (%) | Low No. of Patients (%) |
|---|---|---|---|
| Cell type | | | |
| Adenocarcinoma | 52 | 33 (30.0) | 19 (17.2) |
| Squamous cell carcinoma | 41 | 23 (20.9) | 18 (16.4) |
| Other | 17 | 9 (8.2) | 8 (7.3) |

Statistical Analysis

Data are presented either as the mean±SD or the mean±SE of at least three independent experiments. The quantitative in vitro and in vivo data were analyzed using the student's t-test. The difference in patient characteristics between the high-level and the low-level groups was analyzed using Fisher's exact test. All analyses were performed using SPSS software (v20.0; SPSS, Inc., Chicago, Ill.). All statistical tests were two-sided and P values <0.05 were considered statistically significant.

Results

Functional Roles of MARCKS Phosphorylation in Lung Cancer Drug Resistance

Figure 10:
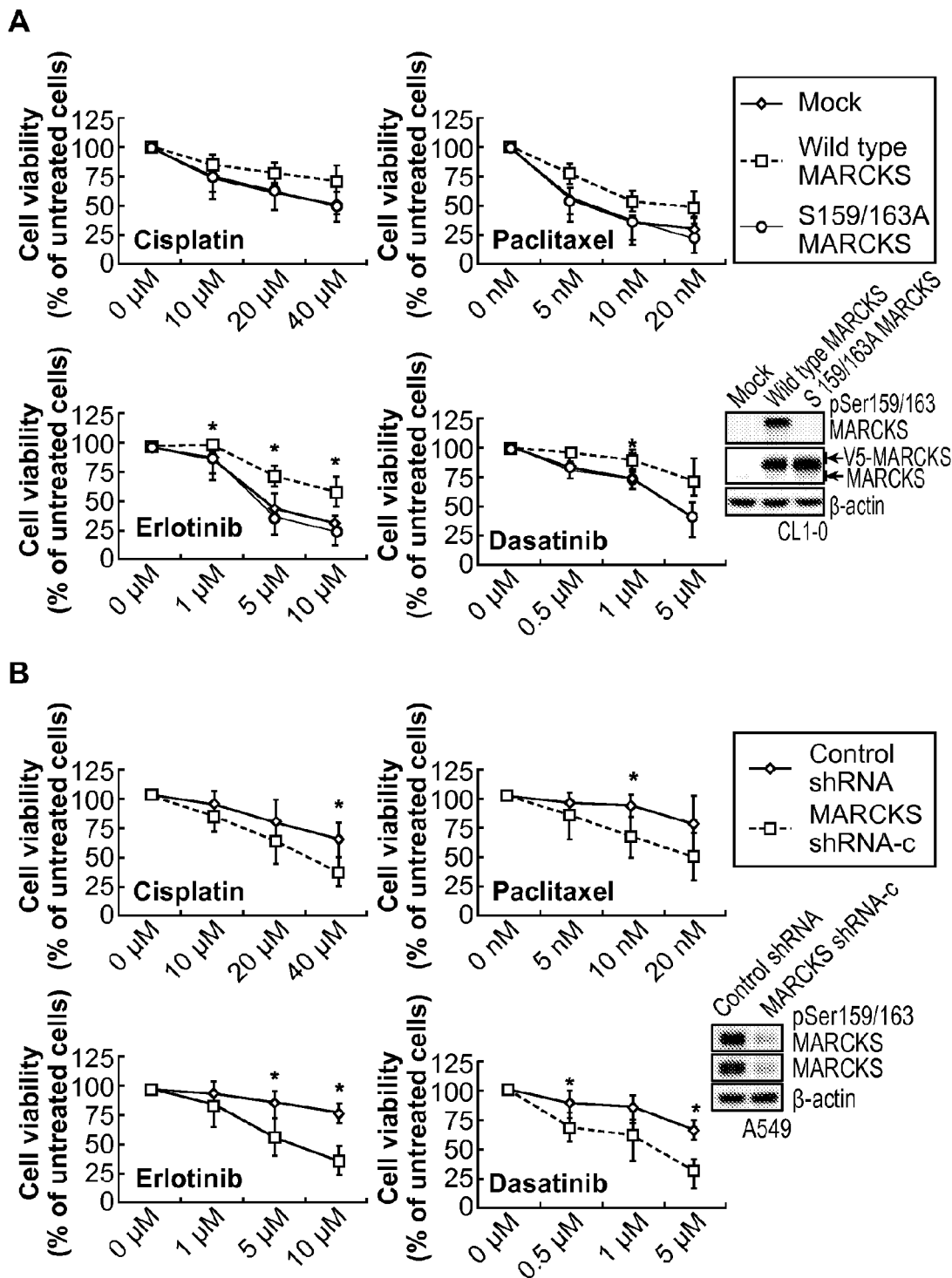
FIGS. 10A and 10B show implication of phospho-MARCKS levels in drug resistance. (A) Effects of ectopic V5-tagged PSD-mutant or wild type MARCKS expression on CL1-0 cells in response to various drug treatments. (B) Effects of MARCKS shRNA silencing on A549 cells in response to various drug treatments. Western blot analyses were carried out to determine phospho-MARCKS and total MARCKS levels in these stable cells with appropriate antibodies. The cells were subjected to various doses of cisplatin, paclitaxel, erlotinib or dasatinib for treatment, as indicated. After 72 hours of treatment, cell viability was determinate by MTS assays. Data shown as mean± SD. *P<0.05 versus mock (A; n=3); *P<0.05 versus control shRNA (B; n=4).

To determine if the MARCKS phosphorylation step can serve as a therapeutic target, Applicants evaluated whether the status of MARCKS PSD phosphorylation could alter the sensitivity of NSCLC cells to chemotherapeutic agents and tyrosine kinase inhibitors (TKIs). The V5-tagged wild-type and PSD-mutated (S159/163A) MARCKS constructs were generated and transfected into low MARCKS-expressing CL1-0 cells (FIG. 16A) (Chen, C. H. et al. (2013) Oncogene) for establishing stable clones. These stable cell lines were exposed to increasing concentrations of cisplatin, paclitaxel, erlotinib or dasatinib for 72 hours. Through the use of a MTS assay, Applicants showed that all these drugs caused a dose-dependent decrease of cell viability in the control mock transfected cells (FIG. 10A). These toxicities were repressed by enforced expression of V5-tagged wild type MARCKS, but not by overexpression of the S159/163A mutant. Notably, an increase of the resistance to erlotinib treatment was the most significant in the study.

In a reciprocal study, Applicants generated the stable MARCKS-knockdown A549 cells by using a common MARCKS-specific short hairpin RNA (MARCKS shRNA-c) (Kalwa, H. et al. (2011) J. Biol. Chem. 286:2320-2330; Rombouts, K. et al. (2013) Cancer Lett. 333:244-252; Jarboe, J. S. et al. (2012) Clin. Cancer Res. 18:3030-3041). MARCKS proteins, along with phospho-MARCKS were silenced in these cells (FIG. 10B, right) and the toxicity effects of these drugs were studied. As shown in FIG. 10B, knockdown of MARCKS expression in A549 cells, which exhibited higher phospho-MARCKS levels than CL1-0 (Chen, C. H. et al. (2013) Oncogene), had an enhanced sensitivity to these drugs. Among the sensitivities to these drugs, the sensitivity to eroltinib was the most dramatic one, as compared to the control-shRNA cells. Taken together, these results reveal a novel function of phospho-MARCKS in conferring drug resistance of lung cancer cells.

Elevated Phospho-MARCKS Levels Promote Lung Cancer Progression

Figure 16:
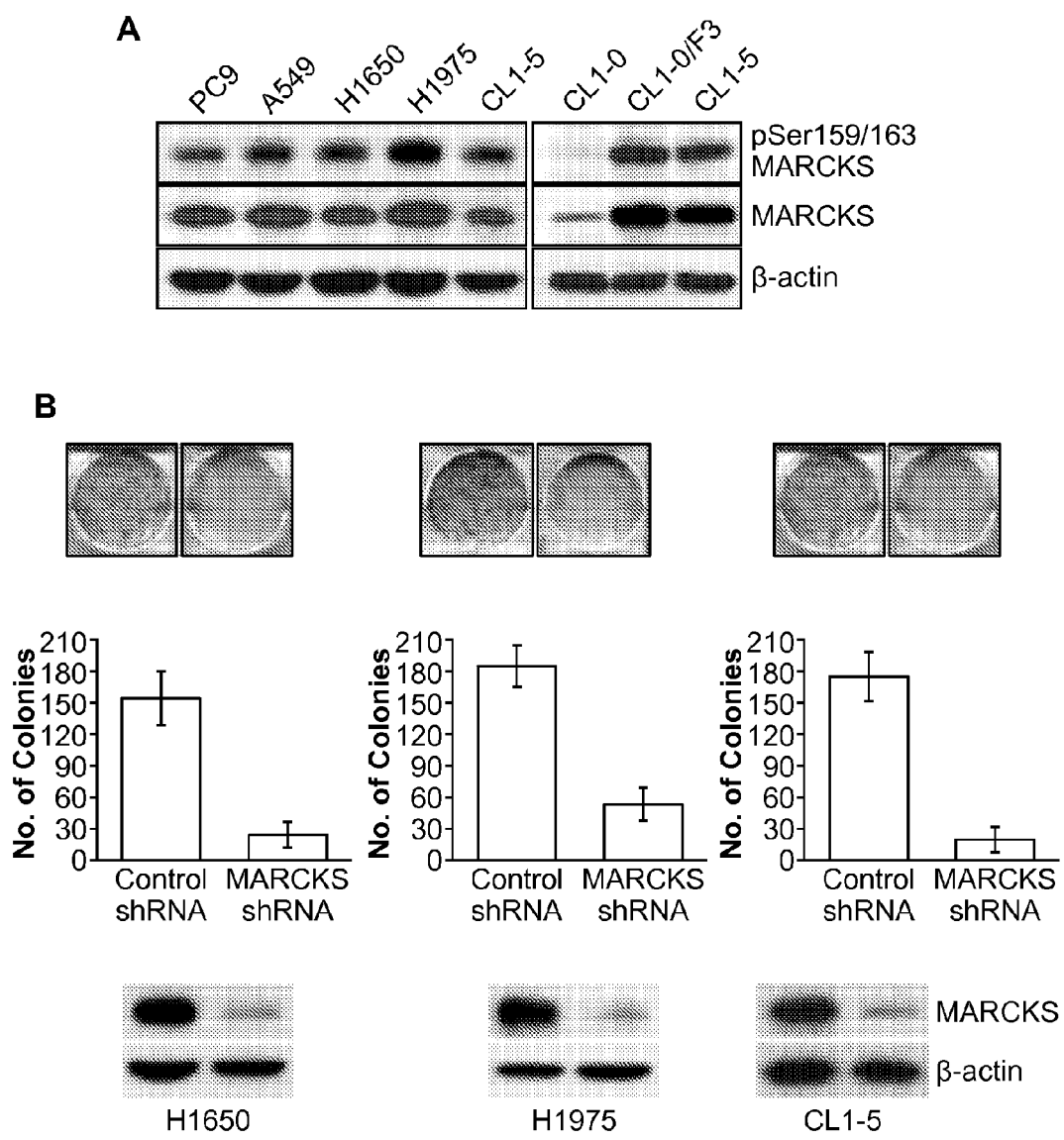
FIG. 16A shows Western blot analyses of MARCKS and its Ser159/163 phosphorylated molecule in various lung cancer cell lines.
FIG. 16B shows H1650, H1975 and CL1-5 cells were infected with MARCKS shRNA-containing lentiviruses. After 24 hours of infection, the cells were selected with 2 μg/mL puromycin and then subjected to anchorage-dependent colony formation assay. Colonies were stained and visualized microscopically. A representative view of each cell line was shown in the upper panel. Middle, colonies were counted in a blinded fashion and quantified (mean±SD, n=3). Bottom, MARCKS expression was determined by Western blot analysis.

Since cell proliferation is a factor to support cancer cells in the development of drug resistance, Applicants investigated whether phospho-MARCKS (Ser159 and Ser163) has a role in tumor growth and tumorigenesis. Stable cell lines with overexpression of V5-tagged wild type or mutant MARCKS, as well as a mock control of unaltered CL1-0 cells, were used to examine the effect of phospho-MARCKS on cell growth. Enforced expression of V5-tagged wild type MARCKS promoted cell proliferation after 48 and 72 hours (FIG. 11A). Using colony forming assay, Applicants observed an approximate 3-fold increase of colony forming ability in cells with ectopic expression of wild type V5-tagged MARCKS and a slight decrease in colony formation in the V5-tagged S159/163A mutant MARCKS-expressing cells, as compared to the mock control cells (FIG. 11B). Conversely, knockdown of endogenous MARCKS expression by using various MARCKS-specific short hairpin RNAs (shRNAs) in A549 cells reduced cell growth in a MARCKS expression-dependent manner (FIG. 11C). The effect of MARCKS phosphorylation on cell proliferation was re-confirmed in various cancer cell lines as knockdown of MARCKS expression (FIG. 16B). To confirm whether phospho-MARCKS promotes cell proliferation in vivo, a subcutaneous xenograft experiment was carried out. As shown in FIG. 11D, the average weight of tumors derived from the MARCKS shRNA-silenced A549 cells was significantly smaller than that of the unaltered control cells. Moreover, immunohistochemistry (IHC) revealed the downregulation of proliferating cell nuclear antigen (PCNA), a proliferation marker, in MARCKS-silenced cells (FIG. 11E). To determine whether the above results have clinical significance, Applicants analyzed phospho-MARCKS levels in lung cancer specimens from 110 patients by using IHC. The clinical characteristics of these patients were summarized in Table 3. There was a significant correlation of phosphorylated MARCKS with the size and/or extent of the primary tumor (T) (FIG. 11G, P=0.017). High levels of MARCKS phosphorylation occurred in higher grade tumor status. These data raise the possibility that elevated phospho-MARCKS drives tumor growth and may contribute to cancer progression.

Activated MARCKS Modulates PIP3 Pools and Contributes to AKT Activation

Figure 11:
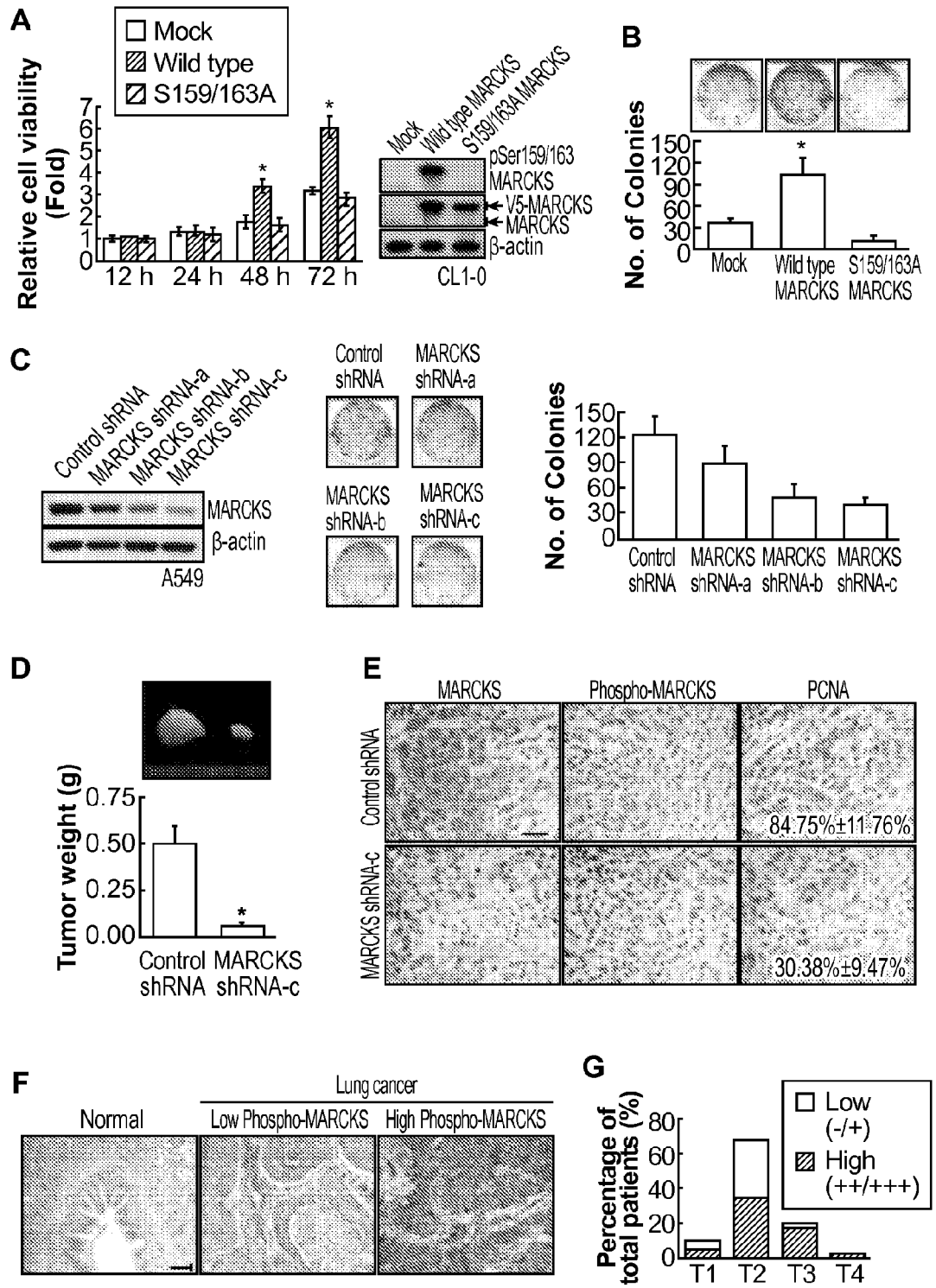
FIGS. 11A-11G show MARCKS activation in promoting lung cancer growth. FIGs. A and B: effects of ectopic V5-tagged mutant or wild-type MARCKS expression on the growth in low MARCKS-expressing cell line, CL1-0 cells as determined by MTS assays (A) and anchorage-dependent colony formation (B). Western blot analyses were carried out to determine phospho-MARCKS and total MARCKS levels in these cells with appropriate antibodies. *P<0.05 versus mock (n=4, mean±SD). (C) Effects of MARCKS shRNA silencing on cell growth as determined by various independent MARCKS-shRNAs in high MARCKS-expressing cell line, A549 cells. PANEL D-E: effects of silencing MARCKS on the growth of xenograft tumor in vivo. (D) A549 cells treated with control or MARCKS-specific shRNA were xenografted subcutaneously to nude mice as described in Material and Methods. After 28 days grafting, tumors were harvested. Top: Representative sizes of tumors. Bottom: tumor weights presented as the mean±SE. *P<0.05 versus control shRNA. (E) Paraffin histology sections were subjected to IHC with various antibodies as indicated. A representative image was shown and positive nuclear staining of PCNA was quantified. *P<0.01 versus control shRNA (n=8; mean±SD). Scale bar: 20 μm. (F) Correlation of high phospho-MARCKS levels with tumor status. Left, representative images of immunohistochemical staining by using anti-pSer 159/163 MARCKS monoclonal antibody in normal lung tissue (n=10) and lung cancer specimens (n=110). Scale bar: 100 μm. (G) percentage of total patients with high and low levels of MARCKS phosphorylation according to primary tumor (T1 to T4).
Figure 12:
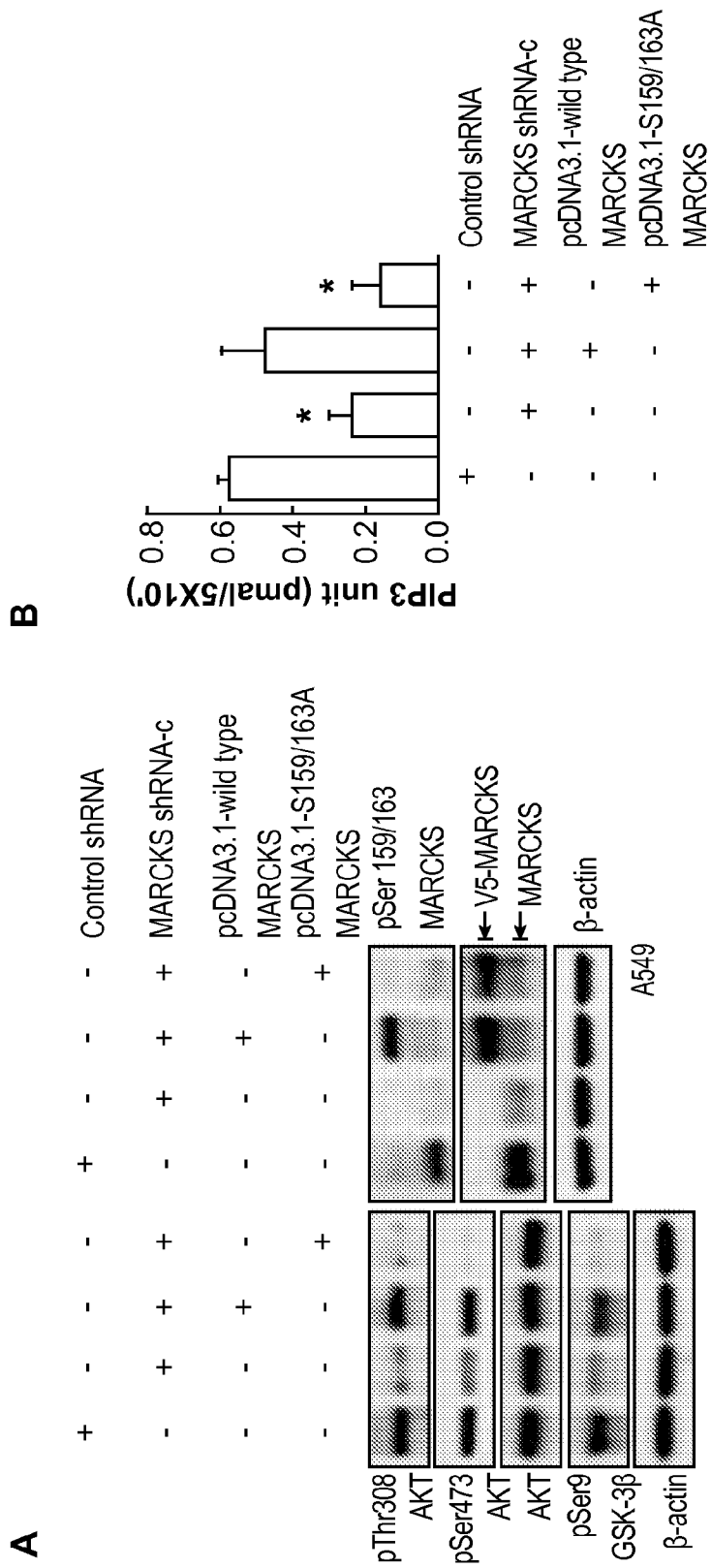
FIGS. 12A-12D MARCKS PSD activity directly regulates PIP3 pools and AKT signalling. (A) Western blot analysis of AKT signaling activation in the MARCKS-knockdown A549 cells with re-expression of wild type and mutant V5-tagged MARCKS. (B) PIP3 levels in these genetically modified A549 cells. PIP3 lipids were extracted from the cells and analyzed by a PIP3 ELISA kit. *$P<0.05$ versus control shRNA (n=4, mean±SD). (C) Determination of the interaction between MARCKS/phospho-MARCKS and PI3K. Cell lysates from A549, H1975 and H1650 cells were respectively analyzed by co-immunoprecipitation followed by immunoblotting with indicated antibodies. (D) Proposed hypothetical model to account for the contribution of MARCKS activity in the enhancement of PIP3 levels: at membrane level, PIP2 lipids in inner membrane domains are concentrated by MARCKS, which is also interacted with PI3K; after phosphorylation by PKC, phospho-MARCKS is detached from membrane and PI3K interaction, and the newly release PIP2 serves as a substrate for PI3K to convert to PIP3 that leads to activating AKT signaling.
Figure 12:
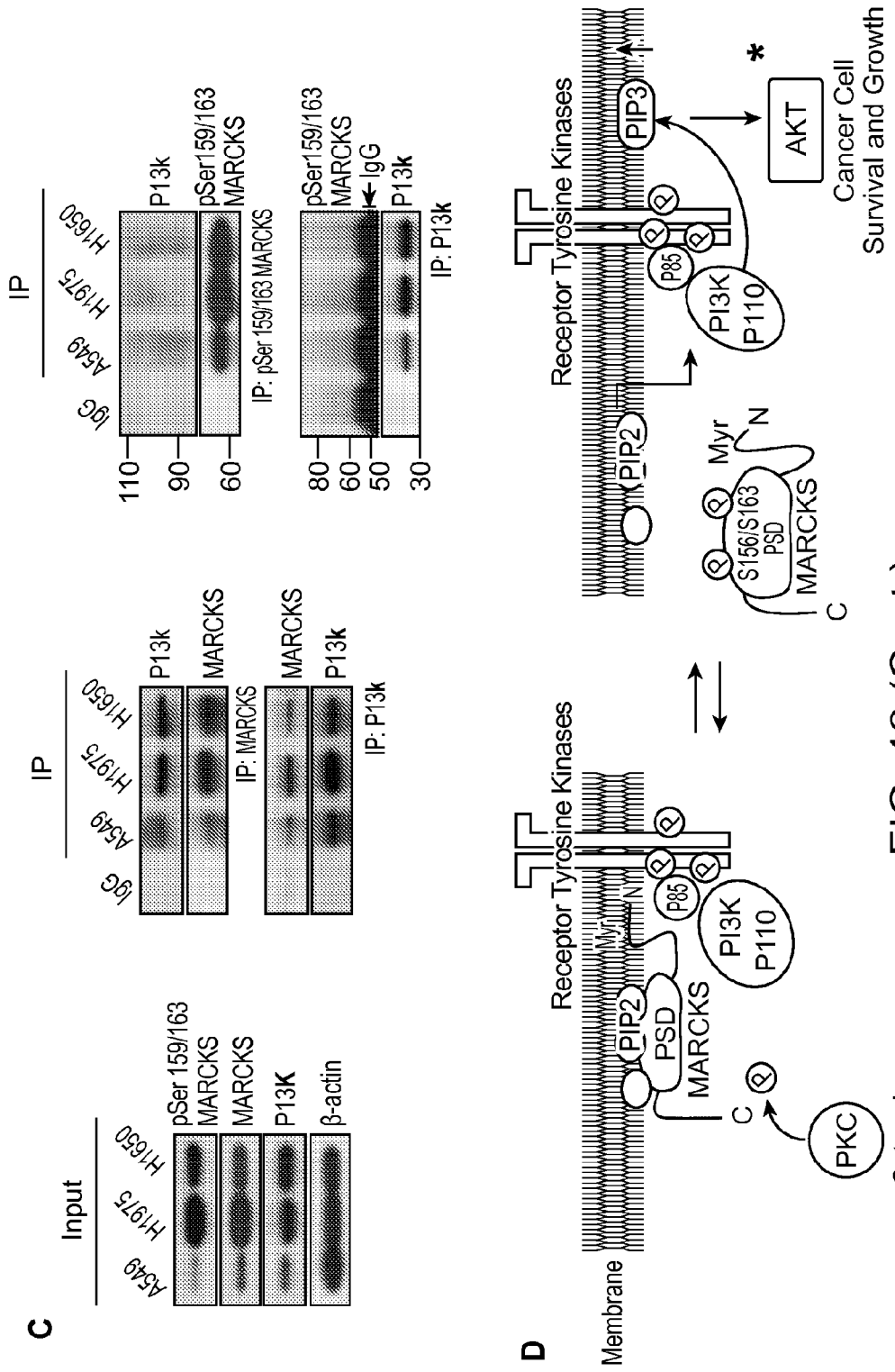
Figure 18:
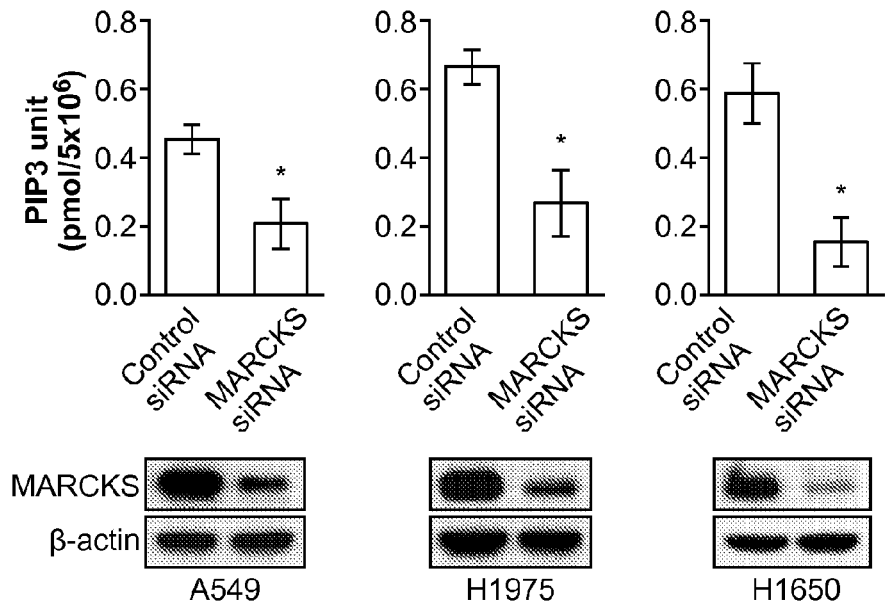
FIG. 18 shows PIP3 levels in drug resistant cancer cell lines after siRNA knockdown of MARCKS. A549, H1975 and H1650 cells were transfected with MARCKS siRNA. 72 hours after transfection, PIP3 lipids were extracted from these cells and analyzed by a PIP3 ELISA kit. *P<0.05 compared with control siRNA cells.

AKT activation is recognized as a key player in cell survival and accounts for erlotinib resistance (Testa, J. R. et al. (2005) Oncogene 24:7391-7393; Sangodkar, J. et al. (2012) J. Clin. Invest. 122:2637-2651; Yamasaki, F. et al. (2007) Cancer Res. 67:5779-5788). Applicants previously reported that phospho-MARCKS was correlated with PI3K/AKT signalling in lung cancer cell lines (Chen, C. H. et al. (2013) Oncogene), thus, there may be existed a mechanism to tie up this correlation. To elucidate such a mechanism, Applicants carried out shRNA silencing approach followed by re-expression of wild type or PSD-mutant (S159/163A) MARCKS to determine if the knockdown activities are reverted by wild type or PSD-mutant MARCKS expression. As shown in FIG. 11, re-expression of wild type MARCKS construct can rescue clonogenic abilities of the silencing cells. Consistently, restorations in AKT phosphorylation both at Ser473 and Thr308 as well as its downstream GSK3-β activity were seen in these silencing cells with overexpression of V5-tagged wild type MARCKS, but not in the cells transfected with PSD-mutated MARCKS (FIG. 12A). Since AKT phosphorylation/activation occurs as a consequence of PIP3 generated on the plasma membrane (Vivanco, I. et al. (2002) Nat Rev Cancer 2:489-501), Applicants examined PIP3 levels in these genetically modified cells. As shown in FIG. 12B, a suppressive effect on PIP3 levels occurred in MARCKS-silenced A549 cells, whereas ectopic expression of V5-tagged wild type MARCKS was able to reverse this suppression and increased PIP3 pools in the cells. A similar MARCKS silencing effect on the suppression of PIP3 levels was also observed in other lung cancer cell lines in addition to A549 cells (FIG. 18).

Figure 19:
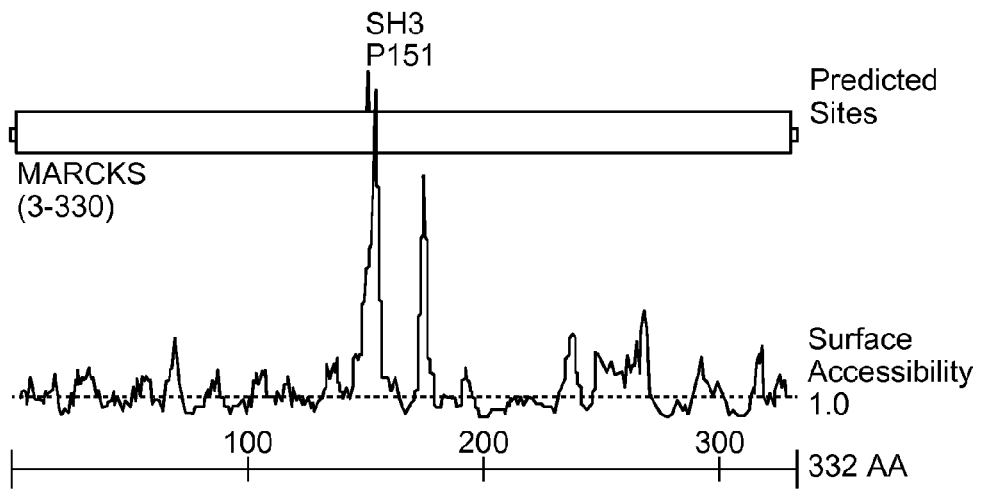
FIG. 19 shows predicted putative p85 (PI3K regulatory subunit) SH3-binding motif on MARCKS protein. The peptide sequence of MARCKS was screened using ScanSite software for p85 SH3 Mode 2 (motifscan.mit.edu). Motif search showed the presence of a putative p85 SH3-binding motif at proline 151 of MARCKS protein (SEQ ID NO: 41).

PI3K is known to catalyze the synthesis of the second messenger PIP3 from PIP2. Unphosphorylated MARCKS has been reported to bind a significant fraction of the PIP2 in cell membrane and then release this lipid in response to local signals, such as PKC activation (McLaughlin, S. et al. (2005) Nature 438:605-611). Therefore, Applicants then asked whether there could be an interaction between MARCKS and PI3K. Sequences analysis of MARCKS protein revealed that MARCKS potentially binds to SH3 domain of p85, a regulatory subunit of PI3K (FIG. 19). Based on this potential, a co-immunoprecipitation assay was performed and demonstrated an association between MARCKS and PI3K in various lung cancer cell lines (FIG. 12C). However, this interaction did not occur between phospho-MARCKS and PI3K, implying that MARCKS is disassociated from PI3K-MARCKS interactive complex after its PSD motif is phosphorylated. These results led to a model for the contribution of MARCKS PSD in regulation of PIP3 levels and AKT activation (FIG. 12D).

Figure 13:
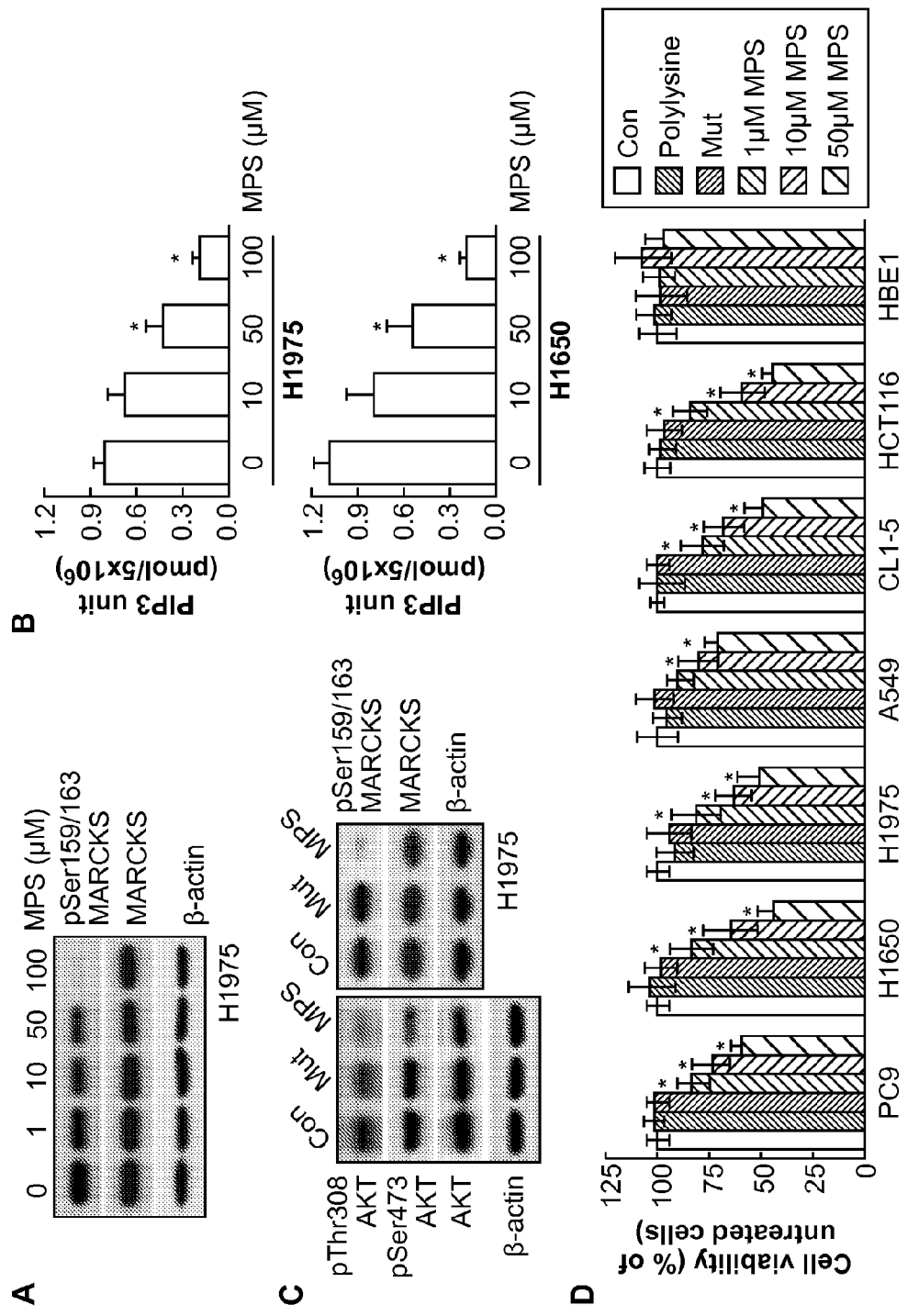
FIGS. 13A-13G show MPS peptide suppresses cancer cell proliferation and also induces apoptosis in these cells through direct downregulation of MARCKS activation. (A) Determination of MARCKS phosphorylation levels after 24 hours of MPS peptide treatment. Lysates from 1-100 μM MPS peptide-treated H1975 cells were subjected to western blot analysis. (B) Levels of PIP3 in drug resistant cancer cell lines after MPS peptide treatment. Cells were treated with 10, 50 or 100 μM MPS peptide. After 24 hours of treatment, PIP3 lipids were extracted from these cells and analyzed by a PIP3 ELISA kit. *$P<0.05$ compared with untreated cells. (C) Downregulation of AKT phosphorylation by MPS peptide treatment, but not by Mut peptide. Cells were treated with 100 μM MPS or Mut peptide for 24 hours. Lysates were immunoblotted with the indicated antibodies. (D) Cell viability analysis of six cancer cell lines and human bronchial epithelial cells (HBE1) upon MPS treatment. Cells were incubated with various concentrations of MPS peptide for 72 hours and then subjected to MTS assays. Polylysine served as a peptide control. n=4, *$P<0.05$ compared with untreated cells (Con). (E) Cells were treated with the indicated concentrations of MPS peptide and colonies were counted after 10 days of treatment using crystal violet staining (F) MPS treatment augments cell death. Cells were exposed to either MPS or mutant (Mut) peptide for 48 hours. The percentages of apoptotic cells were quantified by flow cytometry (top), and presented as mean±SD of three experiments (bottom). *, $P<0.05$ versus untreated cells (Con). (G) Western blot analysis of cleaved caspase-3 and PARP in MPS-treated cells.
Figure 13:
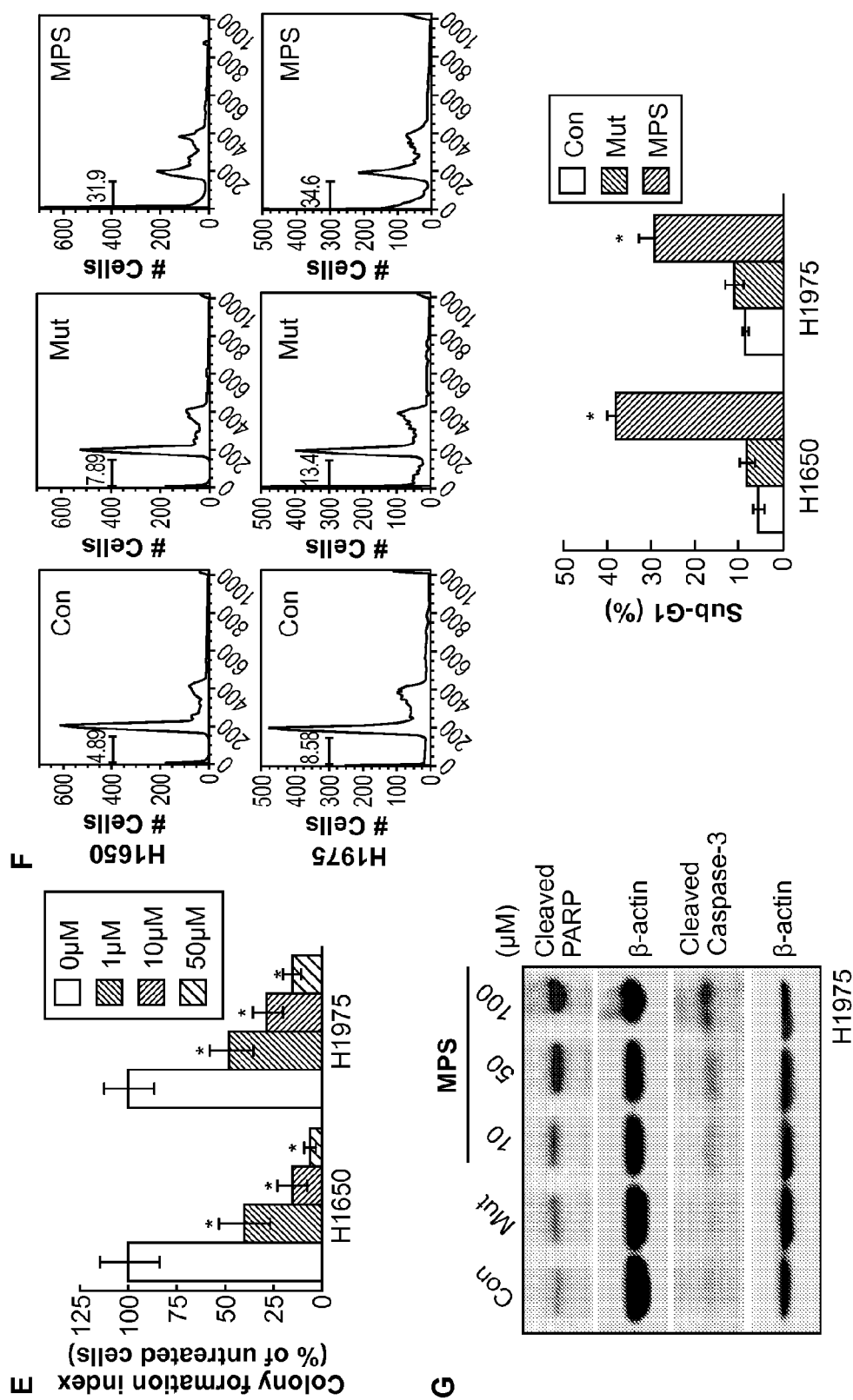

MPS Peptide Treatment has a Cancer-Specific Growth-Inhibitory Effect Through Targeting MARCK PSD According to the sequence of MARCKS PSD, a 25-amino-acid peptide was designed, termed the MPS peptide, in order to inhibit the functions of MARCKS PSD. Applicants first examined whether MPS peptide could have an impact on high levels of phospho-MARCKS seen in lung cancer cells, particularly in TKI resistant cancer cells. Through the use of Western blots, Applicants showed that the MPS peptide reduced MARCKS phosphorylation in a concentration-dependent manner after 24 hours of MPS treatment in TKI resistant cancer cells (FIG. 13A). Moreover, Applicants observed a decrease of PIP3 pools in whole cell lysates of these cells with MPS treatment (FIG. 13B). To confirm the importance of serine residues at MARCKS PSD, an aspartate-substituted MPS peptide (Mut) was used to treat cells. As seen in FIG. 13C, phosphorylated levels of MARCKS and AKT were repressed in MPS-treated cells but not in Mut peptide-treated cells. Based on the molecular results, Applicants examined whether the MPS peptide could serve as a cancer growth inhibitor. Six cancer cell lines and one normal epithelial cell line were treated with various doses of MPS peptide for 72 hours. Impaired cell viability was found in MPS-treated cancer cells but not in lung epithelial cells with MPS treatment (FIG. 13D). Similarly, Applicants did not observe any cytotoxicity in normal human bronchial epithelial cells after Applicants treated these cells with 50 μM MPS peptide (FIG. 20). Of note, an obvious anti-proliferative effect of the MPS peptide was found on various TKIs resistant cancer cells, including H1975, HCT116, H1650 and CL1-5 cells, all of which have either a PI3K CA (constitutively activated) mutation or loss of PTEN function (FIG. 21). Consistent with the above observations, the clonogenic abilities of drug resistant cancer cells were repressed by MPS peptide treatment and this inhibition appeared to be concentration-dependent (FIG. 13E; FIG. 22). Since some MPS-treated cells displayed typical apoptotic morphology, such as cell shrinkage and plasma membrane blebbing, Applicants assessed the sub-G1 fraction by flow cytometry in the H1975 and H1650 cells after 48 hours of MPS treatment. As shown in FIG. 13F, there was a significant increase of the sub-G1 fraction in the treatment groups as compared to untreated and Mut-peptide treated cells; to a level of over 30% higher. In addition, Western blots revealed a MPS dose-dependent occurrence for both cleaved caspase-3 and PARP; two known markers of apoptosis, in these treated cells, as compared to the control untreated and Mut-peptide treated cultures (FIG. 13G). These results show a cancer-specific suppressive activity of the MPS peptide.

MPS Peptide Inhibits Lung Cancer Progression In Vivo

Figure 14:
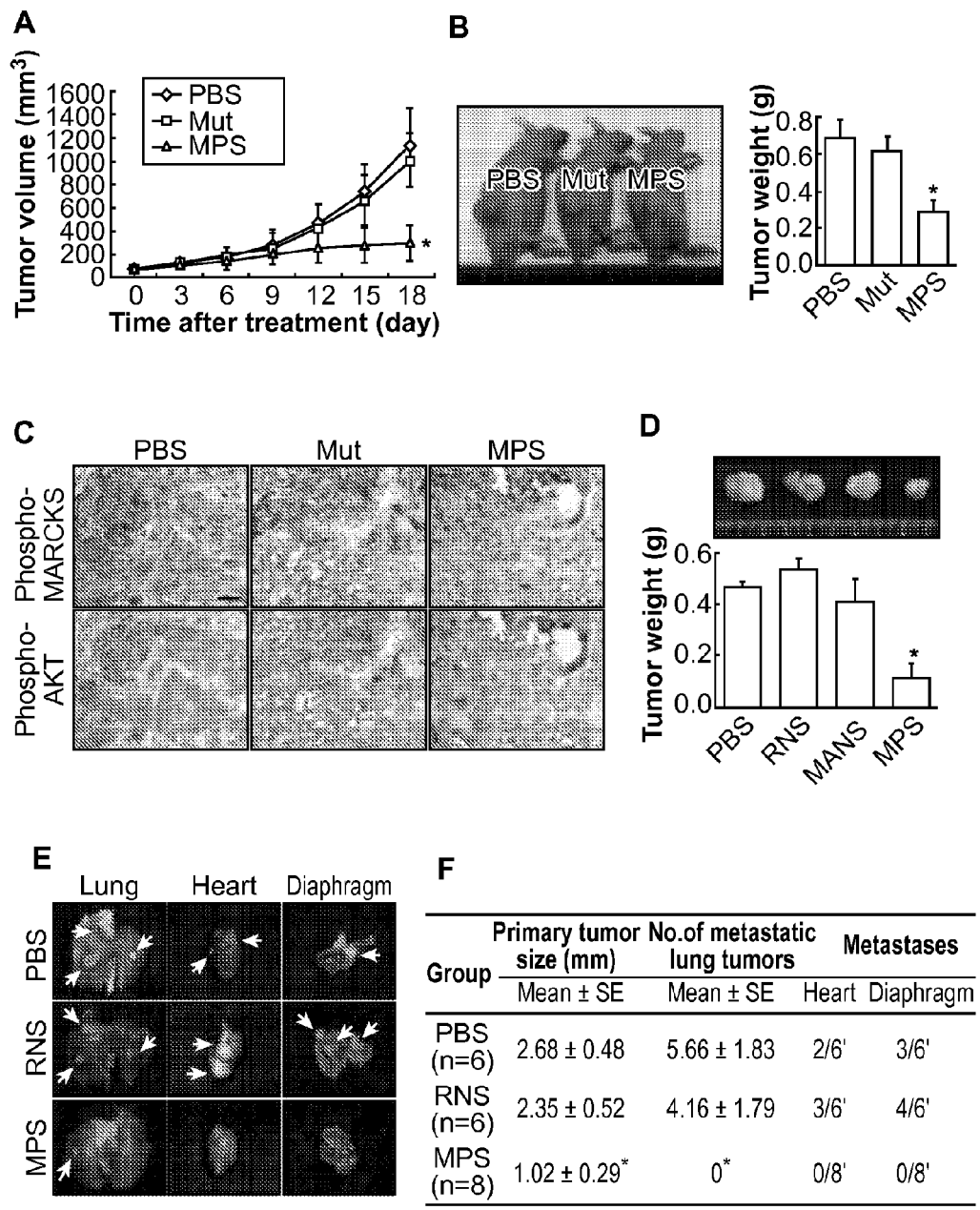
FIGS. 14A-14F show suppressive effects of MPS peptide on cancer growth and metastasis in vivo. (A-C) Suppression of tumorigenesis by MPS peptide. Nude mice bearing subcutaneous tumors were treated for 21 days with intraperitoneal injections of PBS, Mut or MPS peptide at the dosage of 28 mg/kg/3 days. Tumor appearance and volumes were measured and data was presented as mean±SD (n=5, A). A representative photo of primary tumors from subcutaneous tissue of nude mice was shown (B, left). The tumor weights were average values from five mice per group and data were shown as mean±SE (B, right). * $P<0.05$ as compared with PBS group. (C) Immunohistochemical staining of phospho-MARCKS (Ser159/163) and phospho-AKT (Thr308) in xenograft tumor sections as described in B. (D) Nude mice bearing subcutaneous tumors formed from PC9 cells were treated for 21 days with PBS (Con), 50 nmoles RNS, MANS or MPS peptide. Top, a representative photo of primary tumors from subcutaneous tissue of nude mice. Bottom, tumor weights are average values from six mice per group. Data were shown as mean±SE. *$P<0.01$ as compared to PBS-treated group. (E) Inhibition of lung cancer metastasis by MPS peptide. Dissociated PC9 cells were orthotopically injected into the left lobe of the mouse lung. After mice were injected intraperitoneally with PBS, RNS or MPS peptide (14 mg/kg/3 days) for a total of 10 injections, the organs were examined. Left, gross pictures of various organs removed from the mice. The arrows indicate metastatic tumor nodules in each organ and the arrowhead indicates the primary lung tumor at the injected lobe. (F) Quantification of the average pulmonary metastasis nodules from mice with injected cancer cells and treated with RNS or MPS peptide as described (*$P<0.05$ versus PBS).

To determine the anti-cancer effect of the MPS peptide in vivo, H1975 cells were injected subcutaneously into nude mice. Mice were randomly grouped and received either PBS, PBS with Mut peptide (i.p., 28 mg/kg) or PBS with MPS peptide (i.p., 28 mg/kg) every three days for 7 injections. Tumor size was greatly reduced in the MPS-treated group, whereas both the PBS-treated and Mut-treated group showed continuous growth (FIG. 14A). After treatment for 21 days, the animals were sacrificed to evaluated tumor weights. As shown in FIG. 14B, the MPS-treated group showed significantly reduced tumor growths, as compared to either the PBS-treated or Mut-treated group. The average tumor weights were significantly decreased, from 0.69 g in the PBS-treated group to 0.28 g in the MPS-treated group (FIG. 14B, right). Specifically, IHC staining for phospho-MARCKS and phospho-AKT showed that both phospho-MARCKS and phospho-AKT levels were reduced in MPS-treated xenograft tumor sections (FIG. 14C), in agreement with in vitro observations (FIG. 13C).

Figure 23:
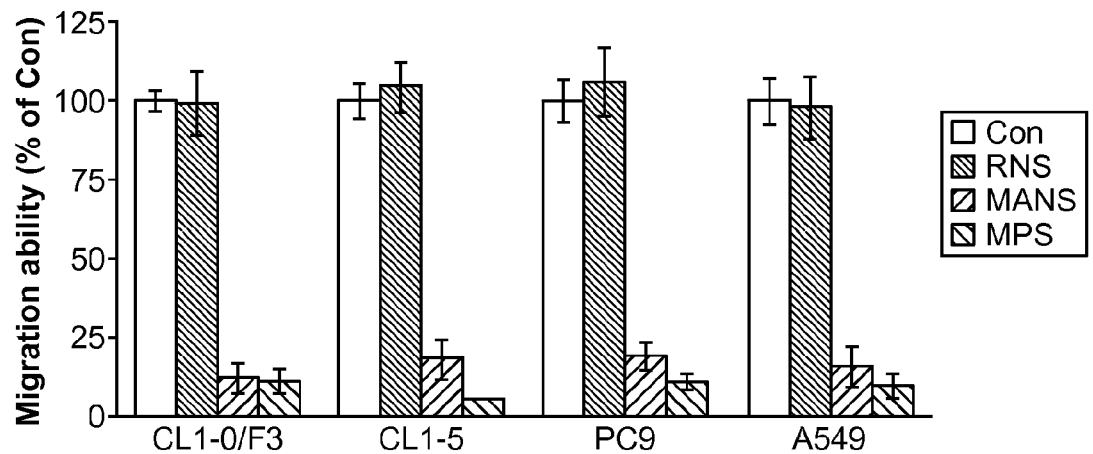
FIG. 23 shows that transwell migration assay demonstrated a higher inhibitory effect of MPS peptide on the invasive cell migration after 12 hours of incubation with RNS (scrambled control peptide), MANS or MPS peptide (100 μM each). The number of migrated cells was normalized to the growth rate at 12 hours by MTS assay for each treatment. Data were expressed as mean±SD (n=2).

Applicants' prior work has shown that the MANS peptide, a 24-amino-acid peptide corresponding to the myristoylated N-terminus of MARCKS, had an effect on reducing lung cancer metastasis but not on tumorigenesis (Chen, C. H. et al. (2013) Oncogene). To further characterize the effect of these two peptides on tumor growth, subcutaneous xenograft tumors were treated with these peptides. As shown in FIG. 14D, MPS peptide was very effective in the inhibition of PC9 tumor growth in xenograft, while MANS and the control scramble RNS peptides were not. In addition, MPS treatment also showed a markedly suppression of cell migration (FIG. 23). To determine whether the MPS peptide inhibits metastatic activities in vivo, Applicants orthotopically inoculated highly metastatic cancer cells into the left lung of mice and examined the metastatic nodules of the right lung of mice that received either PBS, scrambled peptide (RNS) or MPS peptide treatment (i.p., 14 mg/kg/every three days) for 28 days. Similar to MANS peptide (Chen, C. H. et al. (2013) Oncogene), MPS was very effective in suppressing lung cancer metastasis as well as the size of the tumor nodule in the inoculated lung lobe (FIG. 14E). These data indicate that targeting MARCKS PSD with MPS peptide may be more practical than targeting the myristoylation domain in controlling lung cancer progression.

Figure 15:
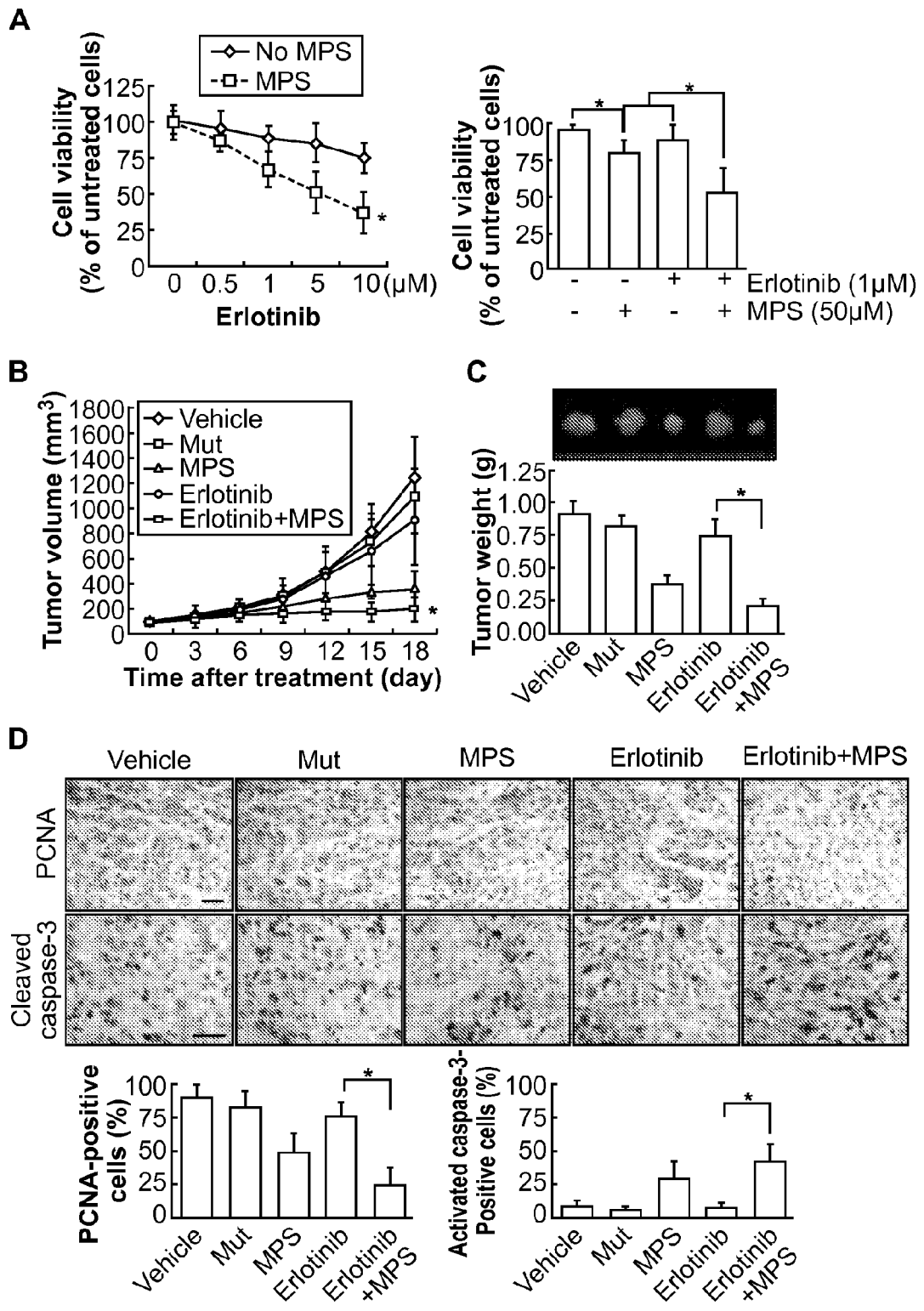
FIGS. 15A-15D show MPS peptide and erlotinib administered in combination decrease lung cancer growth. (A) H1975 cells were co-treated with various dosages of erlotinib and 50 μM MPS peptide. After 48 hours, cell viability was determined by MTS assay (left) and trypan blue dye exclusion assay (right). Left, results are presented as percentage of survival compared with cells grown in the absence of erlotinib (n=5, *$P<0.05$ versus no MPS treatment). Right, cell viability was calculated by the number of viable cells/the number of total cells×100. *, $P<0.05$ (n=4). (B-C) Growth curves and tumor weights of xenograft tumors generated by subcutaneous injection of H1975 cells into the nude mice were shown. Once tumor volume reached averaged 60-80 mm$^3$ at the injected site, mice were randomly grouped for intraperitoneal injection, once for every three days with vehicle, Mut peptide (28 mg/kg), MPS peptide (28 mg/kg), erlotinib (14 mg/kg) alone or together with MPS peptide (28 mg/kg). Tumor measurements were made every three days and data were presented as mean±SD (B, n=5). After 21 days of treatment, the subcutaneous tumors were removed and weighed. Data were expressed as the mean±SE (C, n=7). *$P<0.05$ for erlotinib+MPS as compared to erlotinib alone. (D) Immunohistochemical staining of PCNA and activated caspase-3 in xenograft tumors as described in C. A representative image was shown and positive staining was quantified. *, $P<0.01$ (n=7; mean±SD). Scale bar: 20 μm.
Figure 24:
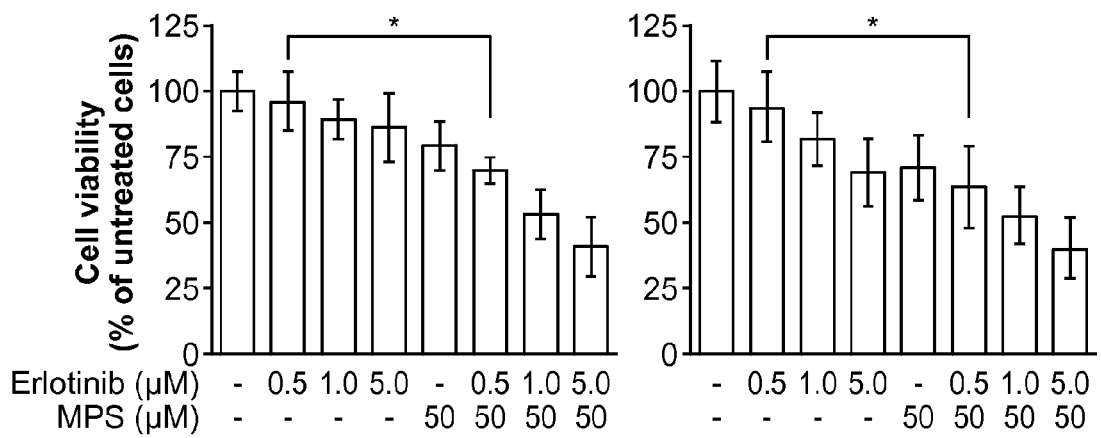
FIG. 24 shows the combinatorial effect of MPS peptide with erlotinib on cancer cell lines. Two erlotinib resistant cell lines, H1975 (left) and H1650 (right), were co-treated with various dosages of erlotinib and 50 μM MPS peptide. After 48 hours, cell viability was determined by MTS assay. *, P<0.05. Lower table, IC50 values of erlotinib for alone and combined treatments with MPS peptide.
Figure 25:
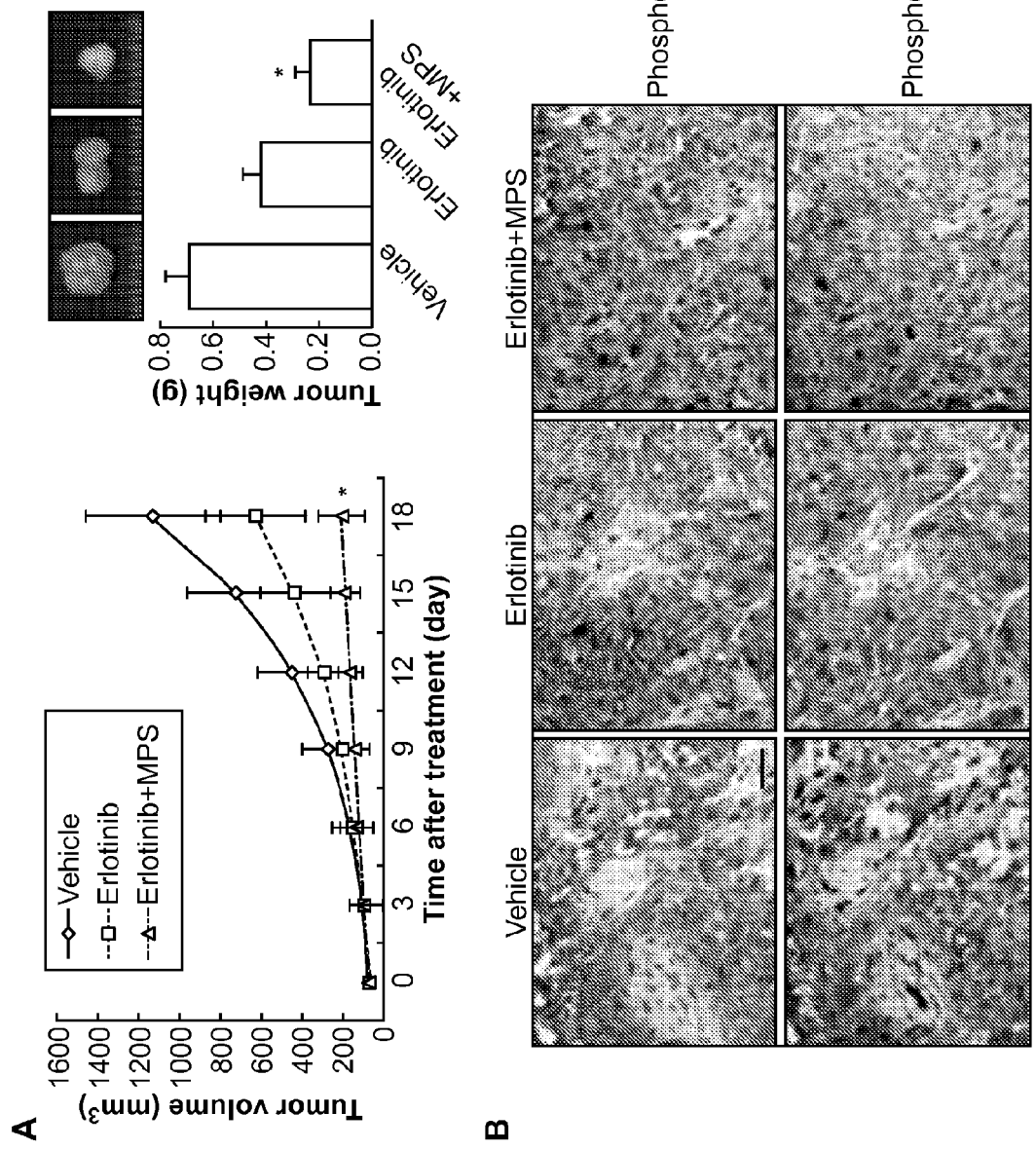
FIG. 25A shows growth curves (left) and tumor weights (right) of xenograft tumors generated by subcutaneous injection of H1975 cells into the nude mice were shown. Once tumor volume reached averaged 60-80 mm$^3$ at the injected site, mice were randomly grouped for intraperitoneal injection, once for every three days with vehicle, erlotinib (28 mg/kg) alone or together with MPS peptide (14 mg/kg). Tumor measurements were made every three days after each drug injection and data were presented as mean±SD (left, n=5). After 21 days of treatment, the subcutaneous tumors of these mice were removed and weighed. Data were expressed as the mean±SE (right). * P<0.05 for erlotinib+MPS as compared to erlotinib alone.
FIG. 25B shows immunohistochemical staining of phospho-MARCKS (Ser159/163) and phospho-AKT (Thr308) in serial sections of xenograft tumor blocks as described in FIG. 25A.

MPS Peptide Acts Synergistically with EGFR Inhibitor Erlotinib in Lung Cancer Treatment Based on the above findings, Applicants presumed that co-treatment with MPS peptide may enhance drug sensitivity of EGFR inhibitor resistant cells. The erlotinib resistant cells were co-treated with various doses of erlotinib and 50 µM MPS peptide for 48 hours. 0.5 µM erlotinib treatment alone had no significant decrease in cell viability as compared to the untreated cells. However, erlotinib treatment combined with 50 µM MPS peptide resulted in over 20% loss of cell viability in both H1975 and H1650 cells (FIG. 24). In particular, there was a stronger synergetic effect found in H1975 cell line (FIG. 15A). To further investigate the synergistic effect of MPS peptide with erlotinib in vivo, Applicants translated these results to animal tumor models by injecting H1975 cells subcutaneously into nude mice. After the tumors reached an average volume of 60-80 mm3, Applicants divided them randomly into several treatment groups. Applicants measured tumor growth in the nude mice every 3 days after treatment for up to 18 days. There was a significant amount of growth inhibition seen in the co-treatment of erlotinib and MPS peptide as compared with erlotinib alone after 12 days of treatment (FIG. 15B and FIG. 25). As indicated by FIG. 15C, the combination of erlotinib and MPS peptide treatment led to the greatest reduction in tumor size (top) and its weight (bottom). Applicants also found an obvious reduction of PCNA expression and increase of activated caspase-3 in these xenograft tumors with combined treatment (FIG. 15D). These results suggest the potential of using MPS peptide alongside erlotinib for the treatment of lung cancer, especially in cancer cells that have developed into TKI resistance.

Discussion

MARCKS phosphorylation is thought to be involved in cell motility and exocytic vesicle release through actin cytoskeletal remodelling. Emerging evidence has suggested that phospho-MARCKS can specifically regulate cancer migration and metastasis (Techasen, A. et al. (2010) Cancer Sci. 101:658-665; Reddy, M. M. et al. (2001) Leukemia 25:281-289; Chen, X. et al. (2010) Cell Signal 22:1097-1103; Yokoyama, Y. et al. (1998) Int. J. Cancer 75:774-749; Chen, C. H. et al. (2013) Oncogene). Here, Applicants showed additional functions of MARCKS phosphorylation in cancer and extend its role beyond cell motility. These results provide the first demonstration of phospho-MARCKS (pSer159/163) promoting cancer growth and conferring drug resistance. In addition, Applicants identified a peptide derived from the MARCKS phosphorylation site domain (PSD), the MPS peptide, as a potential therapeutic agent to block phospho-MARCKS-associated functions in lung cancer.

Lung cancer is the largest cause of death among all cancers types due to both its aggressive progression and high recurrence. Development of biomarkers to identify patients at high risk for aggressive progression is of urgent need. Clinical data demonstrated that higher MARCKS phosphorylation correlated with high-grade tumor status, suggesting that phospho-MARCKS levels may determine the potential of localized lung cancer to progress towards late stage. In clinical practice, the majority of NSCLCs patients with EGFR-activating mutations are treated with EGFR TKIs. Unfortunately, most patients ultimately develop drug resistance and relapse (Crino, L. et al. (2010) Ann Oncol. 21(Suppl. 5):v103-v115; Stinchcombe, T. E. et al. (2009) Proc Am Thorac Soc. 6:233-241; Wheeler, D. L. (2010) Nat Rev Clin Oncol. 7:493-507). Discovery of an alternative targeted therapy in addition to EGFR signaling would be extremely helpful for the treatment of lung cancers with EGFR TKI resistance. In this work, Applicants hypothesized that MARCKS signaling may potentially be an alternative pathway and act as a critical regulator for the crosstalk of signalling between EGFR and PI3K/AKT pathways. It was shown that MARCKS shRNA-silenced cells or V5-tagged S159/163A mutant MARCKS-expressing cells are all more significantly sensitive than control-shRNA or wild type MARCKS elevated cell lines to erlotinib. These manipulations are related to an up- and down-regulation of MARCKS phosphorylation in these cells. These results suggest the importance of phospho-MARCKS status as a good candidate for predicting the response of lung cancer to erlotinib treatment. Both in vitro and in vivo evidence concerning combined treatment of erlotinib with MPS peptide clearly supports the notion further that an inhibition of MARCKS phosphorylation may be able to reduce the occurrence of drug resistance.

PI3K is well known to drive tumor progression through an activation of AKT, triggering a cascade of responses, including cell survival, proliferation, invasiveness and motility (Vivanco, I. et al. (2002) Nat Rev Cancer 2:489-501; Testa, J. R. et al. (2005) Oncogene 24:7391-7393). Although many ATP-binding-site inhibitors have been generated for targeting various kinases (PI3K, AKT and mTOR) (Courtney, K. D. et al. (2010) J. Clin. Oncol. 28:1075-1083), it is important to consider alternative modes for pathway interruption. Reducing the availability of PIP2 to PI3K may represent a powerful approach to alter PI3K/AKT signaling, due to the fact that PIP3 synthesis from PIP2 is a universal upstream step in PI3K signaling. Applicants' studies provide evidence, which is indicative of the fact that the PIP3 required for AKT activation is exclusively supplied after MARCKS phosphorylation. The co-immunoprecipitation assays revealed a unique interaction between MARCKS and PI3K, shown to be dependent on the status of MARCKS phosphorylation. Moreover, siRNA knockdown of MARCKS and MPS-mediated inhibition of MARCKS phosphorylation showed both a reduction in PIP3 pools and AKT phosphorylation. Particularly, MPS peptide is specific against MARCKS PSD and has been reported to not only directly attract PIP2 pools (Glaser, M. et al. (1996) J. Biol. Chem. 271:26187-26193; Ellena, J. F. et al. (2003) Biophys. J. 85:2442-2448) but also responsible for the down-regulation of MARCKS phosphorylation (Elzagallaai, A. et al. (2000) Blood 95:894-902; Graff, J. M. et al. (1991) J. Biol. Chem. 266:14390-14398). Based on the above observations, Applicants speculated that phosphorylation within MARCKS PSD may contribute to the availability of PIP2 to PI3K. MARCKS' unphosphorylated PSD motif can trap PIP2 and facilitate accumulation of PIP2 levels at the plasma membrane (Kalwa, H. et al. (2011) J. Biol. Chem. 286:2320-2330; Glaser, M. et al. (1996) J. Biol. Chem. 271:26187-26193). Due to the binding of PI3K with unphosphorylated MARCKS, PI3K may be able to immediately catalyze PIP2 to PIP3 after MARCKS PSD motif is phosphorylated, which releases PIP2 pools. On the other hand, higher levels of phospho-MARCKS may be an indicator that cellular PIP3 levels are increased, leading to the promotion of AKT activation, especially in cancer cells with PTEN loss or PI3K dysregulation. Overall, inhibition of MARCKS PSD activity, leading to a decrease in PIP2 recruitment and availability of PIP2 to PI3K, may be a promising strategy for drug development.

MARCKS PSD, which has been shown to be crucial for the multi-functions of MARCKS; mediating its membrane binding and release, calcium-calmodulin binding, actin binding and the phosphorylation (Arbuzova, A. et al. (2002) Biochem J. 362:1-12). Many studies used MPS peptide (also termed ED peptide) to elucidate the role of MARCKS PSD (Glaser, M. et al. (1996) J. Biol. Chem. 271:26187-26193; Ellena, J. F. et al. (2003) Biophys. J. 85:2442-2448; Graff, J. M. et al. (1991) J. Biol. Chem. 266:14390-14398; Theis, T. et al. (2013) J. Biol. Chem. 288:6726-6742; Morton, L. A. et al. (2013) ACS Chem. Biol. 8:218-225; Hinrichsen, R. D. et al. (1993) Proc. Natl. Acad. Sci. USA 90:1585-1589). Yet, the pharmacologic function of MPS peptide has been investigated by a few (Elzagallaai, A. et al. (2000) Blood 95:894-902; Gay, E. A. et al. (2008) J. Pharmacol. Exp. Ther. 327:884-890). Applicants' data indicates that MPS specifically inhibits the growth of a broad spectrum of cancer cells while cytotoxicity did not occur in MPS-treated human normal cells, suggesting a cancer-specific suppressive activity. These in vitro activities of the MPS peptide led us to investigate its role in vivo. The MPS peptide was well tolerated upon systemic administration in mice and exhibited a strong role in the inhibition of tumor growth, metastasis and erlotinib resistance. This is, to Applicants' knowledge, the first report showing that this peptide could be used as an effective therapeutic drug for lung cancer treatment. Several possibilities may explain the mechanism(s) of how the MPS peptide can inhibit cancer progression and improve AKT-driven erlotinib resistance. First, the MPS peptide may trap PIP2 pools and compete with membrane-associated MARCKS for PIP2 binding since the MPS peptide has been previously confirmed to be inserted into the membrane and directly interact with PIP2 at the plasma membrane (Glaser, M. et al. (1996) J. Biol. Chem. 271:26187-26193; Ellena, J. F. et al. (2003) Biophys. J. 85:2442-2448; Morton, L. A. et al. (2013) ACS Chem. Biol. 8:218-225). Reduction in MARCKS-mediated PIP2 accumulation may impair the availability of PIP2 to PI3K leading to a decrease in PIP3 synthesis and subsequently resulting in down regulation of AKT activation. Second, it is well documented that both PKC and calmodulin can associate with MARCKS PSD and upon association, result in the detachment of MARCKS from membrane, leading to PIP2 release from MARCKS (Arbuzova, A. et al. (2002) Biochem J. 362:1-12). There is a theoretical possibility that MPS peptide may interfere with the PKC-MARCKS and/or calmodulin-MARCKS interaction in addition to blocking the crosstalk of the above-mentioned signaling pathways, all of which are crucial pathways for cancer progression (Teicher, B. A. (2006) Clin. Cancer Res. 12:5336-5345; Hait, W. N. et al. (1986) J. Clin. Oncol. 4:994-1012). Since MARCKS PSD is mainly phosphorylated by PKC (Chen, C. H. et al. (2013) Oncogene), the possibility of a reduction in the PKC-MARCKS interaction could illustrate why MARCKS phosphorylation was decreased in MPS-treated cells. Lastly, MARCKS is recognized to be a cytoplasmic component of motility signaling, so Applicants considered that MPS-mediated inhibition of cell migration may partly result from a decrease of phospho-MARCKS.

Applicants previously identified a peptide against the N-terminus of MARCKS (the MANS peptide) that can reduce lung cancer metastasis (Chen, C. H. et al. (2013) Oncogene). Compared with MANS peptide, MPS peptide can comprehensively suppress cancer activity, whereas the inhibitory effect of MANS peptide was only on cancer metastasis, suggesting that MPS is more effective than MANS in the treatment of lung cancer. In fact, targeting MARCKS PSD may be more useful than targeting the myristoylation domain since previous studies have determined that myristoylation of MARCKS is not required for many of the in vivo functions of MARCKS through the use of a nonmyristoylatable MARCKS in MARCKS-null mice (Swierczynski, S. L. et al. (1996) Dev. Biol. 179:135-147). MANS peptide could only repress some but not all of MARCKS signaling; in contrast, MPS peptide diminishes both PIP3 pools and phospho-MARCKS levels through specifically suppressing MARCKS PSD activity. Therefore, MPS peptide can trigger a variety of cellular responses, including the inhibition of cell growth, induction of apoptosis, restoration of cellular sensitivity to erlotinib and suppression of cell motility. Importantly, these effects are preferentially induced in PTEN-deficient H1650 or PIK3CA mutant H1795 cells, suggesting that targeting PSD may be an effective therapy against human tumors characterized by elevated PIP3 levels. Importantly, the in vivo data represent a unique step towards the potential application of a peptide-based therapy in cancer treatment and also provides a proof-of-concept basis for identifying additional small molecules that inhibit the activity of MARCKS PSD.

Collectively, Applicants provide evidence that phospho-MARCKS drives lung cancer progression and drug resistance. It is practical to believe that phospho-MARCKS may serve as a biomarker for predicting clinical behavior and treatment response in lung cancer. Specifically, Applicants' studies establish the feasibility of developing anticancer agents through targeting MARCKS PSD activity.

Experiment 4

Targeting the MARCKS Phosphorylation Site Domain in Lung Cancer: Mechanisms and Therapeutic Implications In further work following that reported in Experiment 3, the following was conducted.
Materials and Methods
Materials, Plasmids, and Transfection All reagents, antibodies, and plasmid constructs used in this study are as same as described above.
Cell Culture The CL1-0, CL1-0/F3 and CL1-5 lung cancer cell lines were established and characterized as previously described (Chen, C. H. et al. (2013) Oncogene). Applicants tested their invasiveness for authentication by matrigel invasion assays in the laboratory every month. The cell lines, A549, H1650, H1975, H358 and HCT116, were purchased from the American Type Culture Collection (ATCC; Manassas, Va.) that has performed cell line characterizations. The cell line PC9 was a gift from Dr. Pan-Chyr Yang (National Taiwan University, Taipei, Taiwan). The human bronchial epithelial cell line, HBE1, was a gift from JR Yankaskas, University of North Carolina. These cell lines had been passaged in our laboratory for fewer than 6 months after receipt and their characterizations had been periodically checked in our lab, following the method of characterization at ATCC website. The culture and transfection conditions are as described above.
Immunohistochemical Staining Human lung cancer tissue array was purchased from Biomax Co. (Rockville, Md.). The slides were de-paraffinized in xylene and rehydrated in graded alcohol and water. An antigen retrieval step (10 nM sodium citrate (pH 6.0) at a sub-boiling temperature) was used for each primary antibody. Endogenous peroxidase activity was blocked by 3% hydrogen peroxide followed by blocking serum and incubation with appropriate antibodies overnight at 4° C. Detection of immunostaining was carried out by using the VECTASTAIN® ABC system, according to the manufacturer's instructions (Vector Laboratories, Burlingame, Calif.). A four-point staining intensity scoring system was devised to confirm the relative expression of phospho-MARCKS in cancer specimens; scores ranged from zero (no expression) to 3 (highest-intensity staining) as described previously. The results were classified into two groups according to the intensity and extent of staining: in the low-expression group, staining was observed in 0-1% of the cells (staining intensity score=0), or in less than 10% of the cells (staining intensity score=1); in the high-expression group, staining was present in 10%-50% of the cells (staining intensity score=2), or more than 50% of the cells (staining intensity score=3). These results were reviewed and scored independently by two pathologists.
PI(3,4,5)P3 Quantitation Cells were harvested and precipitated by trichloroacetic acid. PIP3 lipids were extracted twice from the trichloroacetic acid precipitated fraction by methanol:chloroform (2:1). After acidification, organic-phase lipids were used for PIP3 quantitation, based on the protocol for the PIP3 Mass ELISA kit (Echelon Biosciences, Salt Lake, Utah). Briefly, the lipid extract from cultured cells was mixed with the PIP3-specific detector protein, which was then incubated in a PIP3-coated mircroplate for competitive binding. After several washes, the microplate was then incubated with a HRP-linked secondary detector and tetramethylbenzidine substrate for color development. To stop further color development, 2M H2SO4 solution was then added. Microplates were read at an absorbance wavelength of 450 nm. A series of different dilutions of PIP3 standards were used for establishing a standard curve for each reaction. Cellular PIP3 amounts could be estimated by comparing the absorbance in the wells with the values in the standard curve. Experiments were conducted in triplicate dishes and repeated in two independent cultures with cell density $5 \times 10^6$ cells/100-mm dish.
Flow Cytometry Cells were seeded at a density of $2 \times 10^5$ cells/60-mm dish in complete culture medium and treated with or without peptide for 48 hours. Each sample was harvested and stained with 25 μg/mL propidium iodide. These samples were analyzed by flow cytometry using a Cytomics™ FC500 flow cytometer (Beckman Coulter), according to the manufacturer's protocol.
In Vivo Subcutaneous and Orthotopic Implantations Animal usage protocols were periodically reviewed and approved by Institutional Animal Care and Use Committee at UC Davis. Six-week-old nude mice (supplied by Charles River Laboratories, San Diego, Calif.) were housed four mice per cage and fed autoclaved food ad libitum. For the in vivo tumorigenesis assay, the dorsal region of nude mice was injected subcutaneously with $2 \times 10^6$ MARCKS shRNA-silenced A549 cells or A549 control cells. After 28 days, the xenografted tumors were removed, weighed and fixed in 10% formalin; embedded tissues were sliced into 4 μm sections, which were stained with hematoxylin-eosin and anti-PCNA antibody for histological analysis. For the in vivo treatment of peptide or drug assays, the dorsal regions of nude mice were injected subcutaneously with $5 \times 10^6$ H1975 cells and these mice were examined every 3 days for tumor size. Groups were randomized and treatment started when tumor size reached 60-80 mm3 (the tumor volume was calculated by using the formula $V=0.4 \times ab^2$, where a and b are the longest and shortest diameters of the tumors, respectively). These nude mice bearing subcutaneous tumors were intraperitoneally (i.p) injected with PBS, Mut peptide (28 mg/kg), MPS peptide (28 mg/kg), erlotinib (14 mg/kg or 28 mg/kg) alone or MPS peptide (28 mg/kg) combined with erlotinib (14 mg/kg) every three days. After 21 days of treatment, these mice were sacrificed and the xenografted tumors were collected for histological analysis. For orthotopic implantation, PC9 cells ($5 \times 10^4$ cells in 40 μl PBS containing 10 ng Matrigel) were inoculated into the left lung of mice by insulin syringe with 29-G needle. After 7 days of implantation, the mice were subjected to systemic treatment with PBS, RNS (14 mg/kg) or MPS peptide (14 mg/kg) by intraperitoneal injections once every three days. The mice were sacrificed after a total of 10 injections of treatment. The numbers of lung tumor colonies from orthotopic implanted mice were evaluated by gross and microscopic examination.

Statistical Analysis

Data are presented either as the mean±SD or the mean±SE of at least three independent experiments. The quantitative in vitro and in vivo data were analyzed using the student's t-test. The difference in patient characteristics between the high-level and the low-level groups was analyzed using Fisher's exact test. All analyses were performed using SPSS software (v20.0; SPSS, Inc., Chicago, Ill.). All statistical tests were two-sided and P values <0.05 were considered statistically significant.

Results

Functional Roles of MARCKS Phosphorylation in Lung Cancer Drug Resistance

To determine if the MARCKS phosphorylation site can serve as a therapeutic target, Applicants evaluated whether the status of MARCKS PSD phosphorylation could alter the sensitivity of NSCLC cells to chemotherapeutic agents and tyrosine kinase inhibitors (TKIs). The V5-tagged wild-type and PSD-mutated (S159/163A) MARCKS constructs were generated and transfected into low MARCKS-expressing CL1-0 cells (FIG. 16A) (Chen, C. H. et al. (2013) Oncogene), known as a chemosensitive cancer cell line (Lay, J. D. et al. (2007) Cancer Res. 67:3878-3887), for establishing stable clones. These stable cell lines were exposed to increasing concentrations of cisplatin, paclitaxel, erlotinib or dasatinib for 72 hours. Through the use of a MTS assay, Applicants showed that all these drugs caused a dose-dependent decrease of cell viability in the control mock transfected cells (FIG. 10A). These toxicities were repressed by enforced expression of V5-tagged wild type MARCKS, but not by overexpression of the S159/163A mutant. Notably, an increase of the resistance to erlotinib treatment was the most significant in the study.

In a reciprocal study, Applicants generated the stable MARCKS-knockdown A549 cells by using a common MARCKS-specific short hairpin RNA (MARCKS shRNA-c) (Kalwa, H. et al. (2011) J. Biol. Chem. 286:2320-2330; Rombouts, K. et al. (2013) Cancer Lett. 333:244-252; Jarboe, J. S. et al. (2012) Clin. Cancer Res. 18:3030-3041). MARCKS proteins, along with phospho-MARCKS were silenced in these cells (FIG. 10B, right) and the toxicity effects of these drugs were studied. As shown in FIG. 10B, knockdown of MARCKS expression in A549 cells, which exhibited higher phospho-MARCKS levels (Chen, C. H. et al. (2013) Oncogene), had an enhanced sensitivity to these drugs. Among the sensitivities to these drugs, the sensitivity to eroltinib was the most dramatic one, as compared to the control-shRNA cells. Taken together, these results reveal a novel function of phospho-MARCKS in conferring drug resistance of lung cancer cells.

Elevated Phospho-MARCKS Levels Promote Lung Cancer Progression

Since cell proliferation is a factor to support cancer cells in the development of drug resistance, we investigated whether phospho-MARCKS (Ser159 and Ser163) has a role in tumor growth and tumorigenesis. Applicants observed that enforced expression of V5-tagged wild type MARCKS promoted cell proliferation and colony forming ability (FIGS. 11A and 11B), as compared to the mock control of CL1-0 cells. Conversely, knockdown of endogenous MARCKS expression by using various MARCKS-specific short hairpin RNAs (shRNAs) in A549 cells reduced cell growth in a MARCKS expression-dependent manner (FIG. 11C). The effect of MARCKS phosphorylation on cell proliferation was re-confirmed in various cancer cell lines as knockdown of MARCKS expression (FIG. 16B). To confirm whether phospho-MARCKS promotes cell proliferation in vivo, a subcutaneous xenograft experiment was carried out. As shown in FIG. 11D, the average weight of tumors derived from the MARCKS shRNA-silenced A549 cells was significantly smaller than that of the unaltered control cells. Moreover, immunohistochemistry (IHC) revealed the down-regulation of proliferating cell nuclear antigen (PCNA), a proliferation marker, in MARCKS-silenced cells (FIG. 11E). To determine whether the above results have clinical significance, Applicants analyzed phospho-MARCKS levels in lung cancer specimens from 110 patients by using IHC. The clinical characteristics of these patients were summarized in Table 3. There was a significant correlation of phosphorylated MARCKS with the size and/or extent of the primary tumor (T) (FIG. 11F, P=0.017). High levels of MARCKS phosphorylation occurred in higher grade tumor status. These data raise the possibility that elevated phospho-MARCKS drives tumor growth and may contribute to cancer progression.

Activated MARCKS Modulates PIP3 Pools and Contributes to AKT Activation

Figure 17:
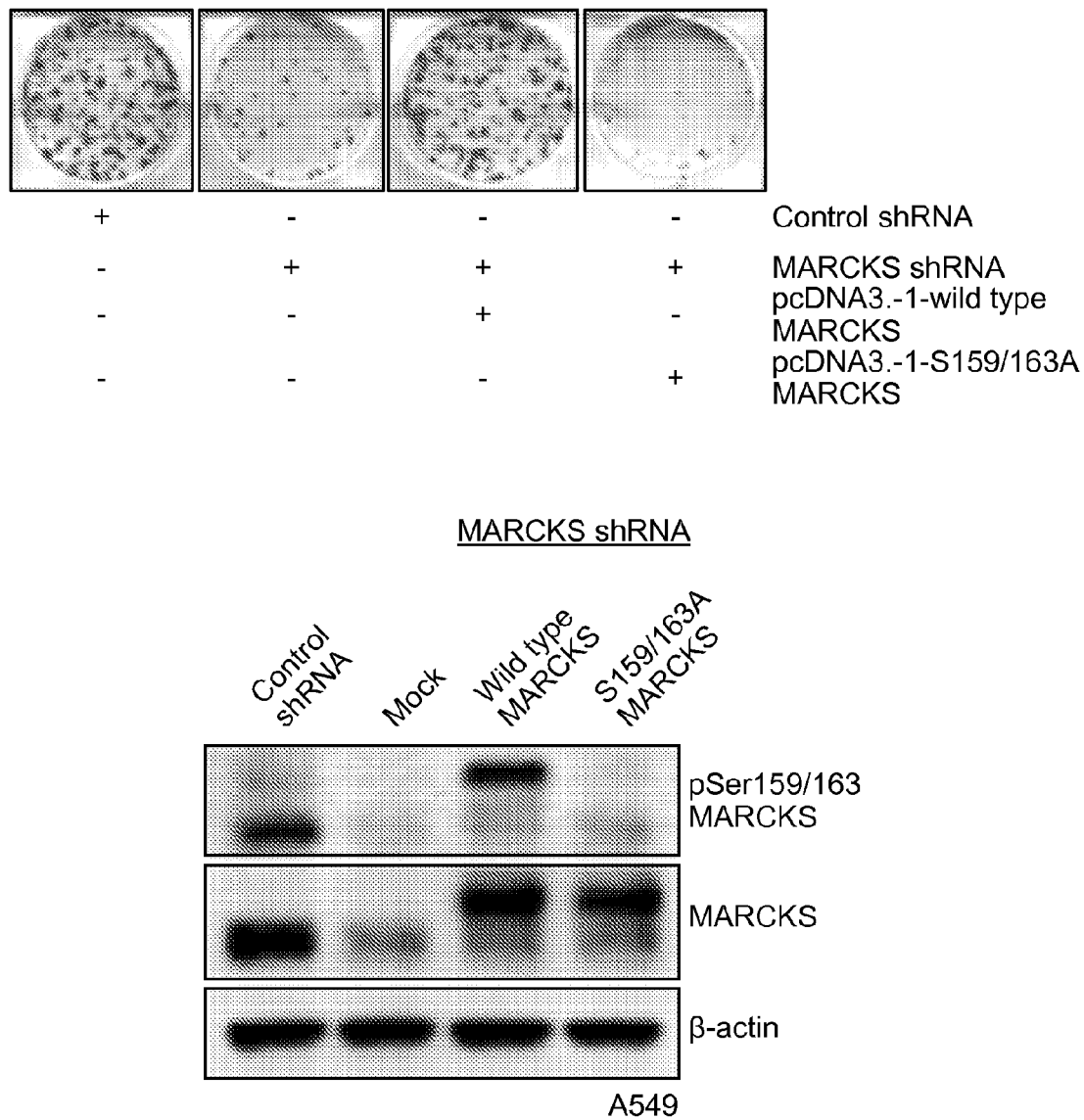
FIG. 17 shows MARCKS-knockdown A549 stable cells were transfected with pcDNA3.1-MARCKS, pcDNA3.1-S159/163A MARCKS or pcDNA3.1 vector respectively for selection of stable cell lines. After that, these cells were subjected to colony forming assays. A representative view of each cell line was shown in the upper panel. Bottom, MARCKS expression was determined by Western blot analysis.

AKT activation is recognized as a key player in cell survival and accounts for erlotinib resistance (Testa, J. R. et al. (2005) Oncogene 24:7391-7393; Sangodkar, J. et al. (2012) J. Clin. Invest. 122:2637-2651; Yamasaki, F. et al. (2007) Cancer Res. 67:5779-5788). Applicants previously reported that phospho-MARCKS was correlated with PI3K/AKT signalling in lung cancer cell lines (Chen, C. H. et al. (2013) Oncogene), thus, there may be existed a mechanism to tie up this correlation. To elucidate such a mechanism, Applicants carried out shRNA silencing approach followed by re-expression of wild type or PSD-mutant (S159/163A) MARCKS to determine if the knockdown activities are reverted by wild type or PSD-mutant MARCKS expression. As shown in FIG. 17, re-expression of wild type MARCKS construct can rescue clonogenic abilities of the silencing cells. Consistently, restorations in AKT phosphorylation both at Ser473 and Thr308 as well as its downstream GSK3-β activity were seen in these silencing cells with overexpression of V5-tagged wild type MARCKS, but not in the cells transfected with PSD-mutated MARCKS (FIG. 12A). Since AKT phosphorylation/activation occurs as a consequence of PIP3 generated on the plasma membrane (Vivanco, I. et al. (2002) Nat. Rev. Cancer 2:489-501), Applicants examined PIP3 levels in these genetically modified cells. As shown in FIG. 12B, a suppressive effect on PIP3 levels occurred in MARCKS-silenced A549 cells, whereas ectopic expression of V5-tagged wild type MARCKS was able to reverse this suppression and increased PIP3 pools in the cells. A similar MARCKS silencing effect on the suppression of PIP3 levels was also observed in other lung cancer cell lines in addition to A549 cells (FIG. 18).

PI3K is known to catalyze the synthesis of the second messenger PIP3 from PIP2. Unphosphorylated MARCKS has been reported to bind a significant fraction of the PIP2 in cell membrane and then release this lipid in response to local signals, such as PKC activation (McLaughlin, S. et al. (2005) Nature 438:605-611). Therefore, Applicants then asked whether there could be an interaction between MARCKS and PI3K. Sequences analysis of MARCKS protein revealed that MARCKS potentially binds to SH3 domain of p85, a regulatory subunit of PI3K (FIG. 19). Based on this potential, Applicants carried out co-immuno-precipitation assay and demonstrated an association between MARCKS and PI3K in various lung cancer cell lines (FIG. 12C). However, this interaction did not occur between phospho-MARCKS and PI3K, implying that MARCKS is disassociated from PI3K-MARCKS interactive complex after its PSD motif is phosphorylated. These results led Applicants to propose a model for the contribution of MARCKS PSD in regulation of PIP3 levels and AKT activation (FIG. 12D).

Figure 26:
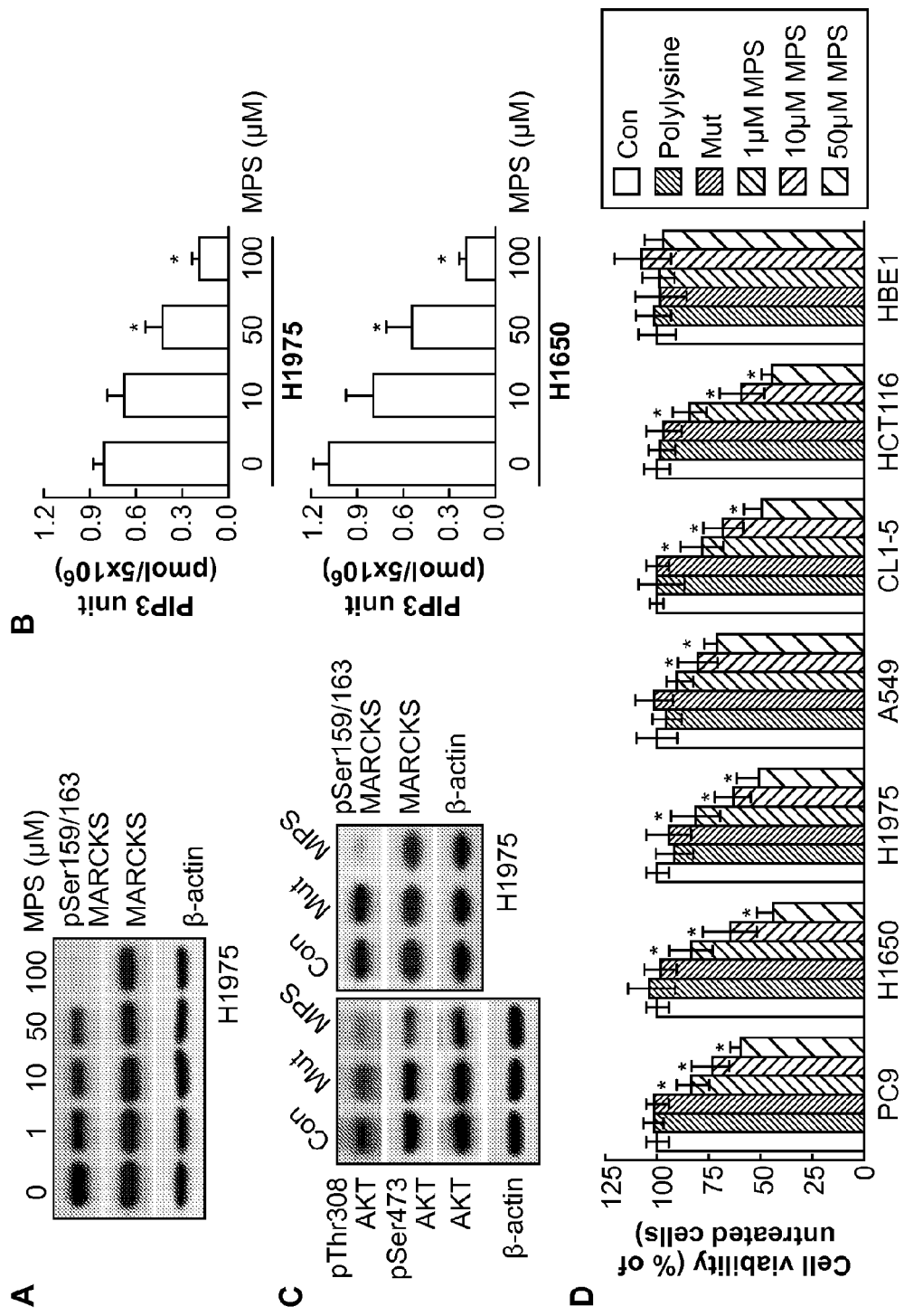
FIGS. 26A-26G show MPS peptide has a cancer-inhibitory effect. (A) Western blot analysis of phospho-MARCKS levels in MPS peptide-treated cells (B) Levels of PIP3 in EGFR-TKI-resistant NSCLC cells after MPS peptide treatment. *P<0.05 compared with untreated cells. (C) Cells were treated with 100 μM MPS or Mut peptide and lysates were immunoblotted with the indicated antibodies. (D) Cell viability analysis of six cancer cell lines and human bronchial epithelial cells (HBE1) upon MPS treatment. Cells were incubated with various concentrations of MPS peptide for 72 hours and then subjected to MTS assays. 50 μM polylysine and Mut (aspartates-substituted mutant) peptide served as peptide controls. n=4, *P<0.05 compared with untreated cells (Con). (E) Cells were treated with the indicated concentrations of MPS peptide and colonies were counted after 10 days of treatment using crystal violet staining (F) Cells were exposed to either MPS or Mut (aspartates-substituted mutant) peptide for 48 hours. The percentages of apoptotic cells were quantified by flow cytometry (top), and presented as mean±SD of three experiments (bottom). *, P<0.05 versus untreated cells (Con). (G) Western blot analysis of cleaved caspase-3 and PARP in MPS-treated cells. Mut peptide (aspartates-substituted mutant; 100 μM) used as a control peptide.
Figure 26:
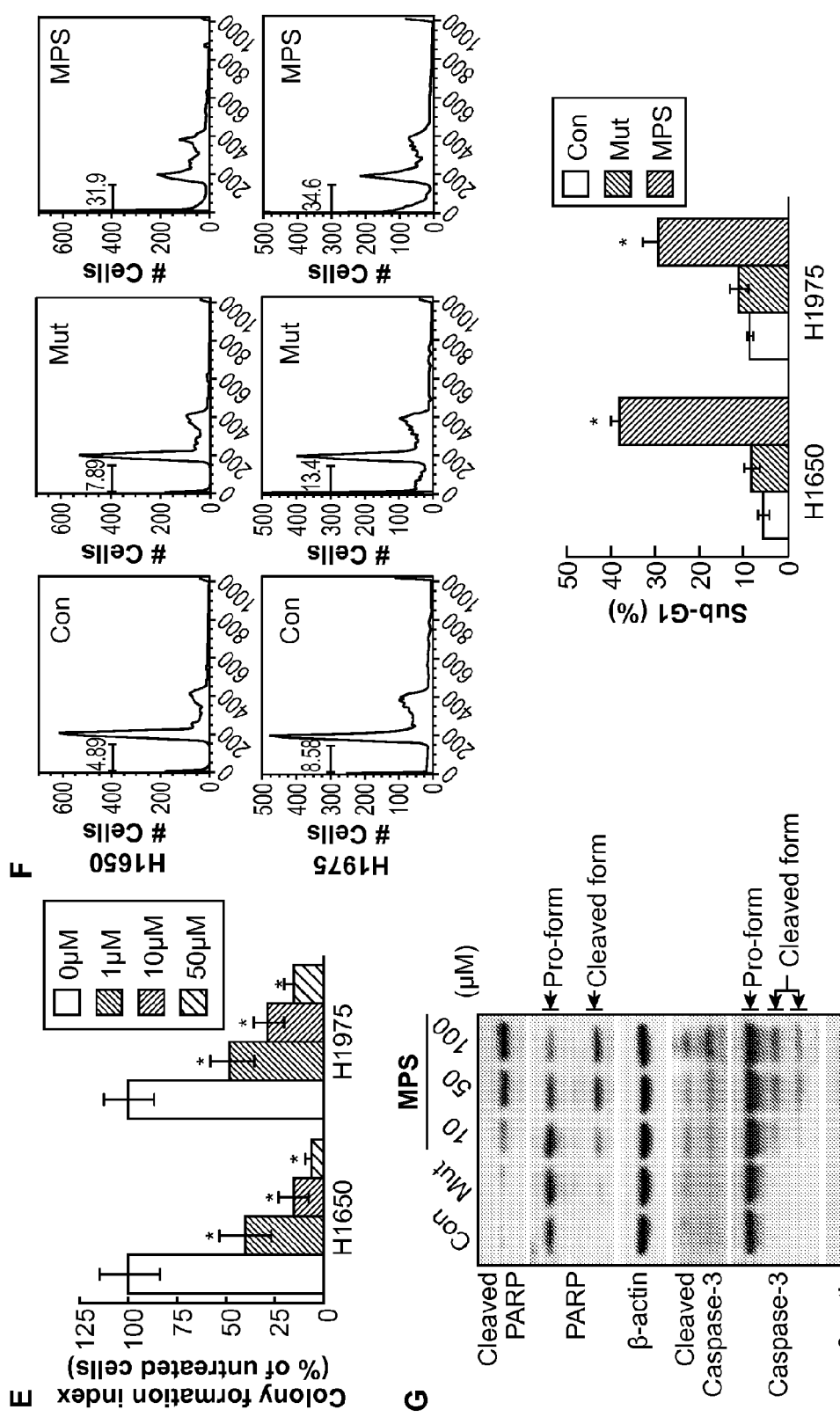
Figure 28:
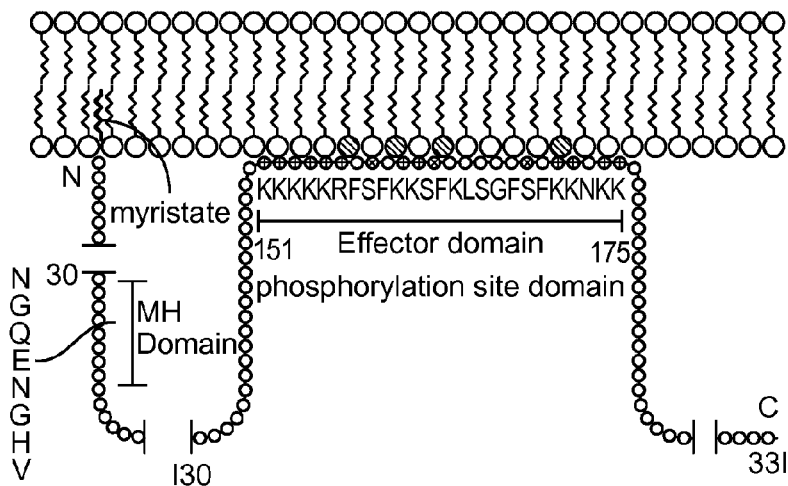
FIGS. 28A-28C show MPS peptide binding to live cells. (A) Peptide sequences showing substitution of serine residues in MPS peptide (SEQ ID NO: 9). The serine residues of MPS peptide were replaced either by adding 4 aspartic acids (SEQ ID NO: 14), which are negatively charged and result in making the final peptide less positive, or by adding 4 alanines (SEQ ID NO: 10), which increased membrane affinity. Both the MPS and alanines-substituted (A-Mut) MPS peptides are highly positive charged and interact electrostatically with PIP2 on the phospholipid membrane. In contrast, electrostatic interaction with cell membrane is decreased in aspartates-substituted (D-Mut) MPS peptide (Gambhir, A. et al. (2004) Biophys. J. 86:2188-2207; Rusu, L. et al. (2004) Biophys J. 87:1044-1053; Glaser, M. et al. (1996) J. Biol. Chem. 271:26187-26193; Ellena, J.F. et al.
Figure 28:
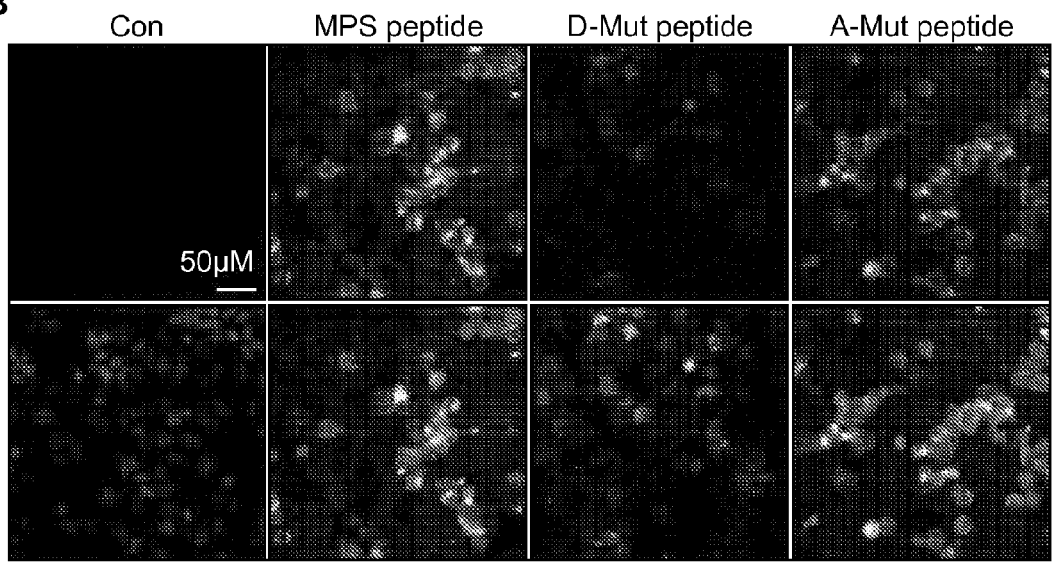
Figure 28:
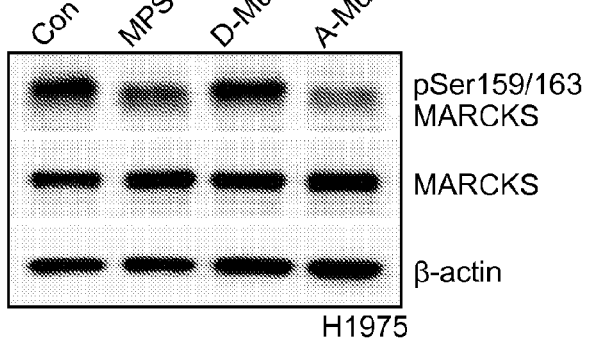

MPS Peptide Treatment has a Cancer-Specific Growth-Inhibitory Effect Through Targeting MARCK PSD According to the sequence of MARCKS PSD, we designed a 25-amino-acid peptide, termed the MPS peptide, in order to inhibit the functions of MARCKS PSD. Applicants first examined whether MPS peptide could have an impact on high levels of phospho-MARCKS seen in lung cancer cells, particularly in TKIs resistant cancer cells. Through the use of Western blots, Applicants showed that MPS peptide reduced MARCKS phosphorylation in a concentration-dependent manner in TKI resistant cancer cells (FIG. FIG. 26A); concurrently, a decrease of PIP3 pools in whole cell lysates of MPS treated cells was also observed (FIG. 26B). Next, applicants confirmed the importance of serine residues present in the MPS peptide for its binding to the cell membrane by using peptides with substitutions at these serine residue sites (FIGS. 28A and 28B). As seen in FIG. 26C and FIG. 28C, phosphorylation levels of MARCKS and AKT were repressed in MPS-treated cells but not in aspartates-substituted MPS (Mut) peptide-treated cells. Based on the molecular results, Applicants examined whether the MPS peptide could serve as a cancer growth inhibitor. Six cancer cell lines and one normal epithelial cell line were treated with various doses of MPS peptide for 72 hours. Impaired cell viability was found in MPS-treated cancer cells but not in lung epithelial cells with MPS treatment (FIG. 26D). Similarly, Applicants did not observe any cytotoxicity in normal human bronchial epithelial cells and lung cancer cells with low phospho-MARCKS levels after treatment with various concentrations of MPS peptide (FIG. 29A and FIG. 29B). Of note, Applicants found an obvious anti-proliferative effect of the MPS peptide on various TKIs resistant cancer cells, including H1975, HCT116, H1650 and CL1-5 cells, all of which have either a PI3K CA (constitutively activated) mutation or loss of PTEN function (FIG. 21). Consistent with the above observations, the clonogenic abilities of drug resistant cancer cells were repressed by MPS peptide treatment and this inhibition appeared to be concentration-dependent (FIG. 26E; FIG. 22). Since Applicants noticed some MPS-treated cells displayed typical apoptotic morphology, such as cell shrinkage and plasma membrane blebbing, Applicants assessed the sub-G1 fraction by flow cytometry in the H1975 and H1650 cells after 48 hours of MPS treatment. As shown in FIG. 26F, there was a significant increase of the sub-G1 fraction in the treatment groups as compared to untreated and Mut-peptide treated cells; to a level of over 30% higher. In addition, Western blots revealed a MPS dose-dependent occurrence for both cleaved caspase-3 and PARP; two known markers of apoptosis, in these treated cells, as compared to the control untreated and Mut-peptide treated cultures (FIG. 26G. Applicants' results suggest a strong cancer-specific suppressive activity of MPS peptide.

MPS Peptide Inhibits Lung Cancer Progression In Vivo

To determine the anti-cancer effect of the MPS peptide in vivo, H1975 cells were injected subcutaneously into nude mice. Mice were randomly grouped and received either PBS, PBS with Mut peptide (i.p., 28 mg/kg) or PBS with MPS peptide (i.p., 28 mg/kg) every three days for 7 injections. Tumor size was greatly reduced in the MPS-treated group, whereas both the PBS-treated and Mut-treated group showed continuous growth (FIG. 14A). After treatment for 21 days, the animals were sacrificed to evaluated tumor weights. As shown in FIG. 14B, the MPS-treated group showed significantly reduced tumor growths, as compared to either the PBS-treated or Mut-treated group. The average tumor weights were significantly decreased, from 0.69 g in the PBS-treated group to 0.28 g in the MPS-treated group (FIG. 14B, right). Specifically, IHC staining for phospho-MARCKS and phospho-AKT showed that both phospho-MARCKS and phospho-AKT levels were reduced in MPS-treated xenograft tumor sections (FIG. 14C), in agreement with in vitro observations (FIG. 26C).

Applicants' recent publication has shown the MANS peptide, a 24-amino-acid peptide corresponding to the myristoylated N-terminus of MARCKS, had an effect on reducing lung cancer metastasis but not on tumorigenesis (Chen, C. H. et al. (2013) Oncogene). To further characterize the effect of these two peptides on tumor growth, Applicants carried out the treatment on subcutaneous xenograft tumors with these peptides. As shown in FIG. 14D, MPS peptide was very effective in the inhibition of PC9 tumor growth in xenograft, while MANS and the control scramble RNS peptides were not. In addition, MPS treatment also showed a markedly suppression of cell migration (FIG. 23). To determine whether the MPS peptide inhibits metastatic activities in vivo, Applicants orthotopically inoculated highly metastatic cancer cells into the left lung of mice and examined the metastatic nodules of the right lung of mice that received either PBS, scrambled peptide (RNS) or MPS peptide treatment (i.p., 14 mg/kg/every three days) for 28 days. Similar to MANS peptide (Chen, C. H. et al. (2013) Oncogene), MPS was very effective in suppressing lung cancer metastasis as well as the size of the tumor nodule in the inoculated lung lobe (FIG. 14E). These data indicate that targeting MARCKS PSD with MPS peptide may be more practical than targeting the myristoylation domain in controlling lung cancer progression.

Figure 27:
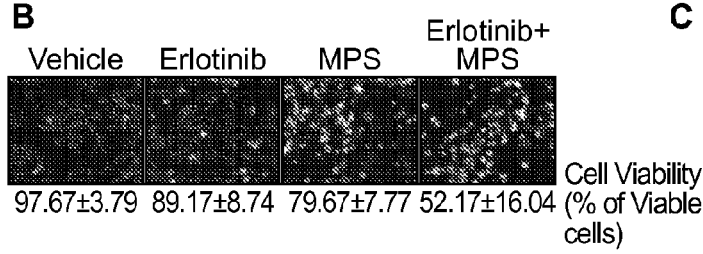
FIGS. 27A-27F show MPS peptide and erlotinib administered in combination decrease lung cancer growth. (A) Combination indices of EGFR inhibitor erlotinib with MPS peptide in EGFR-TKI-resistant NSCLC cells. Cells were treated with combinations of erlotinib plus MPS peptide at various concentrations and combination indices were determined by using CalcuSyn software. The experimental values of the fixed dose ratios of erlotinib/MPS combinations showed a synergistic effect (CI<1) at various effective dose (ED). (B) H1975 cells were individually treated with 5 μM erlotinib, 50 μM MPS peptide or combinations of 5 μM erlotinib and 50 μM MPS peptide. After 48 hours, cell morphology (top) was photographed and cell viability (bottom) was determined by trypan blue exclusion assay (n=4). Cell viability was calculated by the number of viable cells/ the number of total cells×100. (C) Down-regulation of phospho-EGFR, phospho-AKT and phospho-MARCKS in combination treatment. H1975 cells were pretreated with 50 μM MPS peptide for 24 hours and then co-treated with erlotinib as indicated. These cells were harvested 16 hours later and subjected to immunoblotting analysis. PANEL D-E: growth curves and tumor weights of xenograft tumors generated by subcutaneous injection of H1975 cells into the nude mice were described in Material and Methods. Tumor measurements were made every three days and data were presented as mean±SD (D, n=5). After 21 days of treatment, the subcutaneous tumors were removed and weighed. Data were expressed as the mean±SE (E, n=7). * P<0.05 for erlotinib+MPS as compared to erlotinib alone. (F) Immunohistochemical staining of PCNA and activated caspase-3 in xenograft tumors as described in D. A representative image was shown and positive staining was quantified as mean±SD (n=7). Scale bar: 50 μm.
Figure 27:
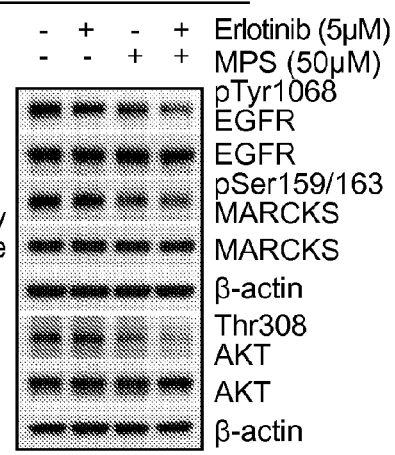
Figure 27:
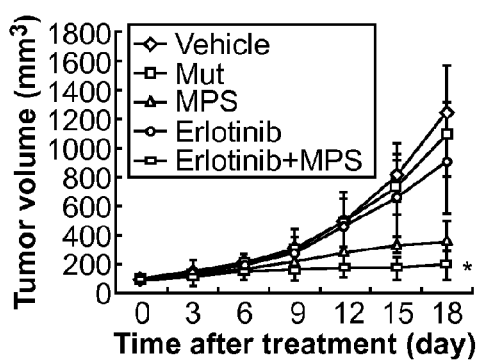
Figure 27:
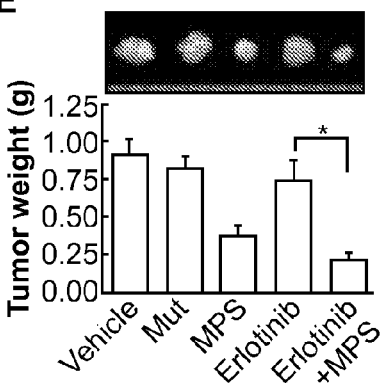
Figure 27:
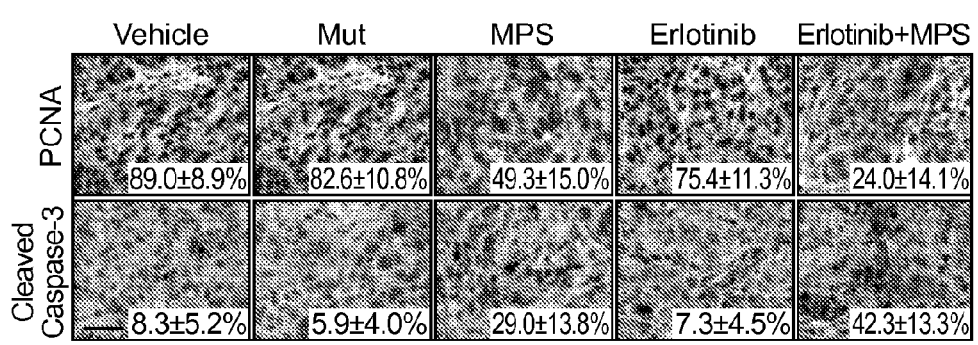

MPS Peptide Acts Synergistically with EGFR Inhibitor Erlotinib in Lung Cancer Treatment Based on the above findings, Applicants presumed that co-treatment with MPS peptide may enhance drug sensitivity of EGFR inhibitor resistant cells. Four erlotinib resistant cell lines were co-treated with various doses of erlotinib (0.625-10 µM) and MPS peptide (12.5-200 µM) for 72 hours. Using the Chou-Talalay method (Chou, T. C. et al. (1984) Adv. Enzyme Regul. 22:27-55) to evaluate the therapeutic interactions, combination indices (CI) indicated a synergistic interaction between erlotinib and MPS peptide treatment in H1975, H1650, H358 and A549 cells (FIG. 27A and FIG. 30). In particular, data from MTS assays showed that the combination of erlotinib (0.5-5 µM) with 50 µM MPS peptide resulted in a decrease of erlotinib IC50 (half maximal inhibitory concentration) (FIG. 24). Likewise, Applicants noticed an increase of floating/dead cells in lung cancer cells receiving both erlotinib and MPS peptide concomitantly, compared to cells receiving erlotinib alone (FIG. 27B). Furthermore, Western blot analyses displayed repression of EGFR-AKT signaling after MPS peptide treatment (FIG. 31) and combination treatment of erlotinib with MPS peptide can remarkably diminish EGFR activity, AKT activation and MARCKS phosphorylation in H1975 cells (FIG. 27E). To further investigate the synergistic effect of MPS peptide with erlotinib in vivo, Applicants translated these results to animal tumor models by injecting H1975 cells subcutaneously into nude mice. After the tumors reached an average volume of 60-80 mm3, Applicants divided them randomly into several treatment groups. Applicants measured tumor growth in the nude mice every 3 days after treatment for up to 18 days. There was a significant amount of growth inhibition seen in the co-treatment of erlotinib and MPS peptide as compared with erlotinib alone after 12 days of treatment (FIG. 27D and FIG. 25). As indicated by FIG. 27E, the combination of erlotinib and MPS peptide treatment led to the greatest reduction in tumor size (top) and its weight (bottom). Applicants also found an obvious reduction of PCNA expression and increase of activated caspase-3 in these xenograft tumors with combination treatment (FIG. 27F TOP). These results suggest the potential of using MPS peptide alongside erlotinib for the treatment of lung cancer, especially in cancer cells that have developed into TKIs resistance.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for one or more of: reducing, delaying, inhibiting or suppressing solid tumor cell growth or metastasis; promoting apoptosis; inhibiting cancer stem cell growth; inhibiting the PIP3 level in a tumor cell; or suppressing tumor cell mobility, the method comprising contacting the cell or tissue to be treated in vivo with an effective amount of an isolated polypeptide comprising no more than 51 amino acids, wherein the amino acid sequence comprises:

XXXRYSYXXSYX (SEQ ID NO: 1) and optionally, wherein one or more serines has been substituted with a neutral or positively charged amino acid, wherein each X is a lysine and wherein each Y is a phenylalanine; or XXXXXRYSYXXSYXLSGYSYXXNXX (SEQ ID NO: 5), and optionally a polypeptide comprising any contiguous 12 amino acid fragment thereof, and/or optionally, wherein one or more serines has been substituted with a neutral or positively charged amino acid and wherein each X is a lysine and wherein each Y is a phenylalanine.

2. A method for restoring sensitivity of a chemoresistant cancer cell to a chemotherapeutic drug or agent in a subject having received the chemotherapeutic drug or agent, the method comprising contacting the cell in vivo with an effective amount of an isolated polypeptide comprising no more than 51 amino acids, wherein the amino acid sequence comprises:

XXXRYSYXXSYX (SEQ ID NO: 1) and optionally, wherein one or more serines has been substituted with a neutral or positively charged amino acid, wherein each X is a lysine and wherein each Y is a phenylalanine; or XXXXXRYSYXXSYXLSGYSYXXNXX (SEQ ID NO: 5), and optionally a polypeptide comprising any contiguous 12 amino acid fragment thereof, and/or optionally, wherein one or more serines has been substituted with a neutral or positively charged amino acid and wherein each X is a lysine and wherein each Y is a phenylalanine; and optionally, wherein the chemotherapeutic drug or agent is a TKI drug or agent optionally selected from cisplatin, paclitaxel, erlotinib or dasatinib; and optionally wherein the chemoresistant cancer cell is a TKI resistant cell.

3. A method for one or more of: reducing, delaying, inhibiting or suppressing solid tumor cell growth or metastasis; promoting apoptosis; inhibiting cancer stem cell growth; inhibiting the PIP3 level in a tumor cell; or suppressing tumor cell mobility, the method comprising contacting the cell or tissue to be treated in vivo with an effective amount of an isolated polypeptide comprising no more than 51 amino acids, wherein the amino acid sequence comprises:

XXXRYAYXXAYX (SEQ ID NO: 11) wherein each X is a lysine and wherein each Y is a phenylalanine; or XXXXXRYAYXXAYXLAGYAYXXNXX (SEQ ID NO: 12) and optionally a polypeptide comprising any contiguous 12 amino acid fragment thereof, wherein each X is a lysine and wherein each Y is a phenylalanine.

4. A method for restoring sensitivity of a chemoresistant cancer cell to a chemotherapeutic drug or agent in a subject having received the chemotherapeutic drug or agent, the method comprising contacting the cell in vivo with an effective amount of an isolated polypeptide comprising no more than 51 amino acids, wherein the amino acid sequence comprises:

XXXRYAYXXAYX (SEQ ID NO: 11) wherein each X is a lysine and wherein each Y is a phenylalanine; or XXXXXRYAYXXAYXLAGYAYXXNXX (SEQ ID NO: 12) and optionally a polypeptide comprising any contiguous 12 amino acid fragment thereof, wherein each X is a lysine and wherein each Y is a phenylalanine;

optionally, wherein the chemotherapeutic drug or agent is a TKI drug or agent optionally selected from cisplatin, paclitaxel, erlotinib or dasatinib; and optionally wherein the chemoresistant cancer cell is a TKI resistant cell.

5. The method of any of claims 1, 2, 3 or 4, wherein the cell is a mammalian cell.

6. The method of any of claims 1, 2, 3 or 4, wherein the tumor cell comprises elevated or higher levels of phosphorylated MARCKS polypeptide as compared to a normal counterpart cell.

7. The method of any of claims 1, 2, 3 or 4, wherein the tumor cell is selected from the group of a lung cancer cell, a colon cancer cell, a breast cancer cell or a pancreatic cancer.

8. The method of any of claims 1, 2, 3 or 4, wherein the tumor cell is isolated from a patient suffering from advanced cancer (Stage II to IV).

9. The method of any of claims 1, 2, 3 or 4, further comprising contacting the cell with an effective amount of a chemotherapeutic drug or agent.

10. A method for one or more of: reducing, delaying, inhibiting or suppressing solid tumor cell growth or metastasis; promoting apoptosis; inhibiting cancer stem cell growth; suppressing tumor cell mobility; inhibiting the PIP3 level in a tumor cell in a subject in need thereof, the method comprising administering to the subject an effective amount of an isolated polypeptide comprising no more than 51 amino acids, wherein the amino acid sequence comprises:

XXXRYSYXXSYX (SEQ ID NO: 1) and optionally, wherein one or more serines has been substituted with a neutral or positively charged amino acid, wherein each X is a lysine and wherein each Y is a phenylalanine; or XXXXXRYSYXXSYXLSGYSYXXNXX (SEQ ID NO: 5), and optionally a polypeptide comprising any contiguous 12 amino acid fragment thereof, and/or optionally, wherein one or more serines has been substituted with a neutral or positively charged amino acid and wherein each X is a lysine and wherein each Y is a phenylalanine.

11. A method for restoring sensitivity of a chemoresistant tumor cell to a chemotherapeutic drug or agent in subject in need thereof, comprising administering to the subject an effective amount of an isolated polypeptide comprising no more than 51 amino acids, wherein the amino acid sequence comprises:

XXXRYSYXXSYX (SEQ ID NO: 1) and optionally, wherein one or more serines has been substituted with a neutral or positively charged amino acid, wherein each X is a lysine and wherein each Y is a phenylalanine; or XXXXXRYSYXXSYXLSGYSYXXNXX (SEQ ID NO: 5), and optionally a polypeptide comprising any contiguous 12 amino acid fragment thereof, and/or optionally, wherein one or more serines has been substituted with a neutral or positively charged amino acid and wherein each X is a lysine and wherein each Y is a phenylalanine; and optionally, wherein the chemotherapeutic drug or agent is selected from a TKI, a drug or agent that targets EGFR, a platinum drug, cisplatin, paclitaxel, erlotinib or dasatinib; and optionally wherein the chemoresistant cancer cell is a TKI resistant cell.

12. A method for one or more of: reducing, delaying, inhibiting or suppressing solid tumor cell growth or metastasis; promoting apoptosis; inhibiting cancer stem cell growth; suppressing tumor cell mobility; inhibiting the PIP3 level in a tumor cell in a subject in need thereof, the method comprising administering to the subject an effective amount of an isolated polypeptide comprising no more than 51 amino acids, wherein the amino acid sequence comprises:

XXXRYAYXXAYX (SEQ ID NO: 11) wherein each X is a lysine and wherein each Y is a phenylalanine; or XXXXXRYAYXXAYXLAGYAYXXNXX (SEQ ID NO: 12) and optionally a polypeptide comprising any contiguous 12 amino acid fragment thereof, wherein each X is the same or different and is a basic amino acid and wherein each Y is the same or different and is a hydrophobic amino acid.

13. A method for restoring sensitivity of a chemoresistant tumor cell to a chemotherapeutic drug or agent in subject in need thereof, comprising administering to the subject an effective amount of an isolated polypeptide comprising no more than 51 amino acids, wherein the amino acid sequence comprises:

XXXRYAYXXAYX (SEQ ID NO: 11) wherein each X is a lysine and wherein each Y is a phenylalanine; or XXXXXRYAYXXAYXLAGYAYXXNXX (SEQ ID NO: 12) and optionally a polypeptide comprising any contiguous 12 amino acid fragment thereof, wherein each X is a lysine and wherein each Y is a phenylalanine;

optionally, wherein the chemotherapeutic drug or agent is selected from a TKI, a drug or agent that targets EGFR, a platinum drug, cisplatin, paclitaxel, erlotinib or dasatinib; and optionally wherein the chemoresistant cancer cell is a TKI resistant cell.

14. The method of any one of claims 10, 11, 12 or 13, wherein the subject is a mammal.

15. The method of any one of claims 10, 11, 12 or 13, wherein the tumor cell or tumor comprises elevated or higher levels of phosphorylated MARCKS polypeptide as compared to a normal counterpart cell.

16. The method of any one of claims 10, 11, 12 or 13, wherein the tumor cell is selected from the group of a lung cancer cell, a colon cancer cell, a breast cancer cell or a pancreatic cancer.

17. The method of any one of claims 10, 11, 12 or 13, wherein the subject is suffering from advanced cancer (Stage II to IV).

18. The method of any one of claims 10, 11, 12 or 13, further comprising contacting the cell with an effective amount of a chemotherapeutic drug or agent.

19. A method for inhibiting the PIP3 level in a cell, the method comprising contacting the cell or tissue to be treated in vitro with an effective amount of an isolated polypeptide comprising no more than 51 amino acids, wherein the amino acid sequence comprises:

XXXRYSYXXSYX (SEQ ID NO: 1) and optionally, wherein one or more serines has been substituted with a neutral or positively charged amino acid, wherein each X is a lysine and wherein each Y is a phenylalanine;

XXXXXRYSYXXSYXLSGYSYXXNXX (SEQ ID NO: 5), and optionally a polypeptide comprising any contiguous 12 amino acid fragment thereof, and/or optionally, wherein one or more serines has been substituted with a neutral or positively charged amino acid and wherein each X is a lysine and wherein each Y is a phenylalanine;

and optionally, wherein one or more serines has been substituted with a neutral or positively charged amino acid.

20. A method for inhibiting the PIP3 level in a cell, the method comprising contacting the cell or tissue to be treated in vitro with an effective amount of an isolated polypeptide comprising no more than 51 amino acids, wherein the amino acid sequence comprises:

XXXRYAYXXAYX (SEQ ID NO: 11) wherein each X is a lysine and wherein each Y is a phenylalanine; or XXXXXRYAYXXAYXLAGYAYXXNXX (SEQ ID NO: 12) and optionally a polypeptide comprising any contiguous 12 amino acid fragment thereof, wherein each X is a lysine and wherein each Y is a phenylalanine.

21. The method of any one of claims 1, 2, 19, 3 or 4, wherein the isolated polypeptide comprises one or more D-amino acids.

22. The method of any one of claims 10, 11, 12, 13 or 20 wherein the isolated polypeptide comprises one or more D-amino acids.

23. The method of any one of claims 1, 2, or 19, wherein the amino acid sequence comprises SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, or SEQ ID NO: 33, wherein each X is a lysine and wherein each Y is a phenylalanine, and optionally, wherein one or more serines has been substituted with a neutral or positively charged amino acid.

24. The method of claim 10 or 11, wherein the amino acid sequence comprises SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, or SEQ ID NO: 33, wherein each X is a lysine and wherein each Y is a phenylalanine, and optionally, wherein one or more serines has been substituted with a neutral or positively charged amino acid.

\* \* \* \* \*